(12) United States Patent
Biggs et al.

(10) Patent No.: US 7,828,840 B2
(45) Date of Patent: Nov. 9, 2010

(54) MEDICAL DEVICES AND METHODS FOR LOCAL DELIVERY OF ANGIOTENSIN II TYPE 2 RECEPTOR ANTAGONISTS

(75) Inventors: David Paul Biggs, Bloomington, IN (US); David D. Grewe, West Lafayette, IN (US); Anthony O. Ragheb, West Lafayette, IN (US); Patrick H. Ruane, San Mateo, CA (US)

(73) Assignees: Med Institute, Inc., West Lafayette, IN (US); Cook Incorporated, Bloomington, IN (US)

( * ) Notice: Subject to any disclaimer, the term of this patent is extended or adjusted under 35 U.S.C. 154(b) by 52 days.

(21) Appl. No.: 12/291,593

(22) Filed: Nov. 12, 2008

(65) Prior Publication Data
US 2009/0177267 A1    Jul. 9, 2009

Related U.S. Application Data

(60) Provisional application No. 61/003,192, filed on Nov. 15, 2007.

(51) Int. Cl.
*A61F 2/06* (2006.01)
*A61F 13/00* (2006.01)
(52) U.S. Cl. ..................... 623/1.44; 424/423
(58) Field of Classification Search ....... 623/1.42–1.48; 424/423–424; 427/2.1
See application file for complete search history.

(56) References Cited

U.S. PATENT DOCUMENTS

| | | | |
|---|---|---|---|
| 4,105,776 A | 8/1978 | Ondetti et al. |
| 4,168,267 A | 9/1979 | Petrillo, Jr. |
| 4,316,906 A | 2/1982 | Ondetti et al. |
| 4,337,201 A | 6/1982 | Petrillo, Jr. |
| 4,344,949 A | 8/1982 | Hoefle et al. |
| 4,374,829 A | 2/1983 | Harris et al. |
| 4,389,330 A | 6/1983 | Tice et al. |
| 4,410,520 A | 10/1983 | Watthey |
| 4,432,971 A | 2/1984 | Karanewsky et al. |
| 4,452,790 A | 6/1984 | Karanewsky et al. |
| 4,464,317 A | 8/1984 | Thies et al. |
| 4,473,575 A | 9/1984 | Watthey |

(Continued)

FOREIGN PATENT DOCUMENTS

EP    0 503 162    4/1998

(Continued)

OTHER PUBLICATIONS

Sambrook et al., *Molecular Cloning. A Laboratory Manual*, Cold Spring Harbor Press, Table of Contents, (1989).

(Continued)

*Primary Examiner*—Suzette J Gherbi
(74) *Attorney, Agent, or Firm*—Brinks Hofer Gilson & Lione

(57) ABSTRACT

This invention relates to medical devices and an angiotensin II type 2 ($AT_2$) receptor antagonist compound, the medical device being adapted to release the $AT_2$ receptor antagonist compound within a body of a patient. This invention also relates to medical devices and methods of treatment of disease, such as aneurysms and aortic dissection. Medical devices may include coated stents, grafts, stent grafts, balloons and catheters.

18 Claims, 6 Drawing Sheets

U.S. PATENT DOCUMENTS

| | | | |
|---|---|---|---|
| 4,508,729 A | 4/1985 | Vincent et al. | |
| 4,512,924 A | 4/1985 | Attwood et al. | |
| 4,530,840 A | 7/1985 | Tice et al. | |
| 4,542,025 A | 9/1985 | Tice et al. | |
| 4,587,256 A | 5/1986 | Hasler et al. | |
| 4,622,244 A | 11/1986 | Lapka et al. | |
| 4,675,189 A | 6/1987 | Kent et al. | |
| 4,739,762 A | 4/1988 | Palmaz | |
| 4,780,401 A | 10/1988 | Heusser et al. | |
| 4,845,079 A | 7/1989 | Luly et al. | |
| 4,885,292 A | 12/1989 | Ryono et al. | |
| 4,894,437 A | 1/1990 | TenBrink | |
| 4,897,268 A | 1/1990 | Tice et al. | |
| 4,943,449 A | 7/1990 | Aishima et al. | |
| 4,980,283 A | 12/1990 | Huang et al. | |
| 5,034,512 A | 7/1991 | Hudspeth et al. | |
| 5,036,053 A | 7/1991 | Himmelsbach et al. | |
| 5,036,054 A | 7/1991 | Kaltenbronn et al. | |
| 5,045,553 A | 9/1991 | Ueda et al. | |
| 5,055,466 A | 10/1991 | Weller, III et al. | |
| 5,063,207 A | 11/1991 | Doherty et al. | |
| 5,063,208 A | 11/1991 | Rosenberg et al. | |
| 5,064,965 A | 11/1991 | Ocain et al. | |
| 5,066,643 A | 11/1991 | Abeles et al. | |
| 5,071,837 A | 12/1991 | Doherty et al. | |
| 5,075,451 A | 12/1991 | Ocain et al. | |
| 5,087,634 A | 2/1992 | Reitz et al. | |
| 5,089,471 A | 2/1992 | Hanson et al. | |
| 5,091,205 A | 2/1992 | Fan | |
| 5,095,119 A | 3/1992 | Ocain et al. | |
| 5,098,924 A | 3/1992 | Poss | |
| 5,104,869 A | 4/1992 | Albright et al. | |
| 5,106,835 A | 4/1992 | Albright et al. | |
| 5,114,937 A | 5/1992 | Hamby et al. | |
| 5,116,835 A | 5/1992 | Ruger et al. | |
| 5,133,732 A | 7/1992 | Wiktor | |
| 5,138,069 A | 8/1992 | Carini et al. | |
| 5,169,395 A | 12/1992 | Narciso, Jr. | |
| 5,256,687 A | 10/1993 | Becker et al. | |
| 5,264,581 A | 11/1993 | Carini | |
| 5,292,331 A | 3/1994 | Boneau | |
| 5,298,018 A | 3/1994 | Narcisco, Jr. | |
| 5,338,740 A | 8/1994 | Carpino et al. | |
| 5,385,894 A | 1/1995 | deLaszlo et al. | |
| 5,421,955 A | 6/1995 | Lau et al. | |
| 5,441,959 A | 8/1995 | Chakravarty et al. | |
| 5,545,651 A | 8/1996 | Duncia et al. | |
| 5,556,780 A | 9/1996 | Dzau et al. | |
| 5,589,499 A | 12/1996 | Weth | |
| 5,608,075 A | 3/1997 | Campbell, Jr. et al. | |
| 5,627,158 A | 5/1997 | Cho-Chung | |
| 5,693,762 A | 12/1997 | Queen et al. | |
| 5,709,653 A | 1/1998 | Leone | |
| 5,728,068 A | 3/1998 | Leone et al. | |
| 5,734,033 A | 3/1998 | Reed | |
| 5,789,415 A | 8/1998 | Carpino et al. | |
| 5,797,868 A | 8/1998 | Leone | |
| 5,834,449 A | 11/1998 | Thompson et al. | |
| 5,873,904 A * | 2/1999 | Ragheb et al. | 623/1.13 |
| 5,889,020 A | 3/1999 | Huxley et al. | |
| 5,958,884 A | 9/1999 | Kifor et al. | |
| 6,001,881 A | 12/1999 | Weichert et al. | |
| 6,004,989 A | 12/1999 | Naka et al. | |
| 6,090,127 A | 7/2000 | Globerman | |
| 6,129,705 A | 10/2000 | Grantz | |
| 6,143,022 A * | 11/2000 | Shull et al. | 623/1.13 |
| 6,206,931 B1 | 3/2001 | Cook et al. | |
| 6,355,055 B1 * | 3/2002 | Waksman et al. | 623/1.13 |
| 6,372,228 B1 | 4/2002 | Gregory | |
| 6,444,646 B1 | 9/2002 | Rodgers et al. | |
| 6,451,050 B1 * | 9/2002 | Rudakov et al. | 623/1.15 |
| 6,641,811 B1 | 11/2003 | Suthanthiran et al. | |
| 2002/0086356 A1 | 7/2002 | Tuschl et al. | |
| 2002/0168393 A1 * | 11/2002 | Sugimoto | 424/423 |
| 2003/0083339 A1 | 5/2003 | Tamura | |
| 2004/0073190 A1 | 4/2004 | Deem | |
| 2004/0176832 A1 | 9/2004 | Harley | |
| 2005/0266043 A1 | 12/2005 | Tseng | |
| 2005/0278021 A1 | 12/2005 | Bates | |
| 2006/0004441 A1 | 1/2006 | Tijsma et al. | |
| 2006/0088572 A1 | 4/2006 | Tijsma et al. | |
| 2006/0135422 A1 | 6/2006 | Moskowitz | |
| 2006/0223741 A1 | 10/2006 | Smith | |
| 2007/0207186 A1 * | 9/2007 | Scanlon et al. | 424/424 |

FOREIGN PATENT DOCUMENTS

| | | |
|---|---|---|
| EP | 465368 | 5/1998 |
| EP | 1 258 258 A1 | 11/2002 |
| GB | 2103614 | 2/1983 |
| WO | WO 98/53761 | 12/1998 |
| WO | WO 2006/066361 | 6/2006 |
| WO | WO 2006/107336 | 10/2006 |

OTHER PUBLICATIONS

Sandhu, J., "Protein Engineering of Antibodies," *Crit. Rev. Biotech.*, 12(5/6):437-462 (1992).

Singer, I., et al., "Optimal Humanization of 1B4, an Anti-CD18 Murine Monoclonal Antibody, Is Achieved by Correct Choice of Human V-Region Framework Sequences," *J. Immun.*, 150(7):2844-2857 (1993).

Sudhir, P., *Methods in Molecular Biology*, vol. 51, Antibody Engineering Protocols, Humana Press, Inc., Table of Contents (1995).

Timmermans, P., et al., "Angiotensin II Receptors and Angiotensin II Receptor Antagonists," *Pharmacol Rev*, 25(2):205-251 (1993).

Vincent, J.M., et al., "Constrictor and Dilator Effects of Angiotensin II on Cerebral Arterioles," *Stroke*, 36:2691-2695 (2005).

Wang, Z., et al., "Immunolocalization of Subtype 2 Angiotensin II (AT2) Receptor Protein in Rat," *Hypertension*, 32(I):78-83 (1998).

Whitebread, S., et al., "Preliminary Biochemical Characterization of Two Angiotensin II Receptor Subtypes," *Biochemical and Biophysical Research Communications*, 163(1):284-291 (1989).

Wiest S., et al., "Characterization of Distinct Angiotensin II Binding Sites in Rat Adrenal Gland and Bovine Cerebellum Using Selective Nonpeptide Antagonists," *J Cardiovasc Pharmacol*, 17(2):177-184 (1991).

Yiu, A., et al., "Ammunohistochemical Localization of Type-II ($AT_2$) Angiotensin Receptors with a Polyclonal Antibody Against a Peptide from the C-Terminal Tail," *Regul Pept.*, 70(1):15-21 (1997).

Kelley, R., "Engineering Therapeutic Antibodies," *Protein Engineering: Principles and Practice*, Cleland et al. (eds.), Chapter 15; pp. 399-434, John Wiley & Sons, Inc. (1996).

Kim, W. and Kang, K., "Recent Developments of Cathepsin Inhibitors and Their Selectivity," *Expert Opin. Ther. Patents*, 12(3):419-432 (2002).

Köhler, G. and Milstein, C., "Continuous Cultures of Fused Cells Secreting Antibody of Predefined Specificity," *Nature*, 256:495-497 (Aug. 1975).

LeNoble et al., "Angiotensin-II induced angiogenesis is not mediated through $AT_1$, receptor," *The FASEB Journal*, 6(4):A937 (1992).

Li, J., et al., "Effects of $AT_1$, and $AT_2$ Angiotensin Receptor Antagonists in Angiotensin II-Infused Rats," *Hypertension*, 31:487-492 (1998).

Muller, C., et al., "$AT_2$-Antagonist Sensitive Potentiation of Angiotensin II-Induced Vasoconstrictions by Blockade of Nitric Oxide Synthesis in Rate Renal Vasculature," *British J. of Pharmacology*, 122:1495-1501 (1997).

Murata, K., et al., "Collagen Types in Various Layers of the Human Aorta and Their Changes with the Atherosclerotic Process," *Atherosclerosis*, 60(3):251-262 (1986).

Nagashima, H., et al., "Angiotensin II Type 2 Receptor Mediates Vascular Smooth Muscle Cell Apoptosis in Cystic Medial Degeneration Associated with Marfan's Syndrome," *Circulation*, 104[suppl I]:1-282-I-287 (Sep. 2001).

Nagashima, H., et al., "An Angiotensin-Converting Enzyme Inhibitor, Not an Angiotensin II Type-1 Receptor Blocker, Prevents β-aminopropionitrile Monofumarate-Induced Aortic Dissection in Rats," *J. of Vascular Surgery*, 36(4):818-823 (Oct. 2002).

Noguchi, K., et al., "Comparison of Acute Hemodynamic Effects of MC-838, a New Angiotensin-Converting Enzyme Inhibitor, with Captopril in Anesthetized Dogs," *Jap. J. Pharmacol.*, 40:373 (1986).

Nora, E., et al., "Localization of the ANG II Type 2 Receptor in the Microciruclation of Skeletal Muscle," *Am J Physiol.*, 275(4 Pt 2):H1395-1403 (1998).

Orlandi, R., et al., Cloning Immunoglobulin Variable Domains for Expression by the Polymerase Chain Reaction, *Proc. Natl. Acad. Sci. USA.*, 86:3833-3837 (1989).

Plasterk, R. and Ketting, R., "The Silence of the Genes," *Current Opinion in Genetics& Development*, 10:562-567 (2000).

Rakugi, H., et al., "Recognition of Tissue- and Subtype-Specific Modulation of Angiotensin II Receptors Using Antibodies against $AT_1$ and $AT_2$ Receptors," *Hypertens Res.*, 20(1):51-55 (1997).

Reagan, L., et al., "Development of Polyclonal Antibodies Against Angiotensin Type 2 Receptors," *Proc Natl Acad Sci USA*, 90(17):7956-7960 (1993).

*Remington's Pharmaceutical Sciences*, Chapter 76, 17th Edition, p. 1418 (1985).

Ausubel F., et al., "Current Protocols in Molecular Biology", John Wiley & Sons mc, Table of Contents (1994-1998).

Beresford, M. and Fitzsimons, J., "Intracerebroventricular Angiotensin II-Induced Thirst and Sodium Appetite in Rat are Blocked by the $AT_1$ Receptor Antagonists, Losartan (DuP 753), But Not by the $AT_2$ Antagonists, CGP 42112B," *Experimental Physiology*, 77:761-764 (1992).

Brooke, B.S., et al., "Angiotensin II Blockade and Aortic-Root Dilation in Marfan's Syndrome," *N. Eng. J. Med*, 358:2787-2795 (2008).

Carter, P., et al., "Humanization of an Anti-p185$^{HER2}$ Antibody for Human Cancer Therapy," *Proc. Natl. Acad. Sci. USA*, 89:4285-4289 (1992).

Chiu, A., et al., "Identification of Angiotensin II Receptor Subtypes," *Biochem. Biophys. Res. Commun.*, 165:196-203 (Nov. 1989).

Coligan, J., et al., "Current Protocols in Immunology", John Wiley & Sons, Inc., Table of Contents (1991).

Curci, J., et al., "Pharmacologic Supression of Experimental Abdominal Aortic Aneurysms: A Comparison of Doxycycline and Four Chemically Modified Tetracyclines," *J. Vasc Surg*, 28(6):1082-1093 (Dec. 1998).

Deasy, P., "Microencapsulation and Related Drug Processes," Marel Dekker, Inc., New York, Table of Contents (1984).

Daugherty, A., et al., "Antagonism of AT2 Receptors Augments Angiotensin II-induced Abdominal Aortic Aneurysms and Atherosclerosis," *British J. of Phar.*, 134:865-870 (2001).

Eagleton, M., et al., "Early Increased MT1-MMP Expression and Late MMP-2 and MMP-9 Activity During Angiotensin II Induced Aneurysm Formation," *Section of Vascular Surgery*, Dept. of Surgery, U. of Mich. Med. School, Ann Arbor, MI (2006).

Ford, W., et al., "Opposite Effects of Angiotensin $AT_1$ and $AT_2$ Receptor Antagonists on Recovery of Mechanical Function After Ischemia-Reperfusion in Isolated Working Rat Hearts," *Circulation*, 94:3087-3089 (1996).

Heeschen, C., et al., "Nicotine Stimulates Angiogenesis and Promotes Tumor Growth and Atherosclerosis," *Nature Medicine*, 7(7):833-839 (Jul. 2001).

Inagami, T., "Recent Progress in Molecular and Cell Biological Studies of Angiotensin Receptors," *Curr Opin Nephrol Hypertens* 4:47-54 (1995).

Jones, P., et al., "Replacing the Complementarity-Determining Regions in a Human Antibody with Those From a Mouse," *Nature*, 321:522-525 (May 1986).

Johnson, C., et al., "Matrix Metalloproteinase-9 Is Required for Adequate Angiogenic Revascularization of Ischemic Tissues Potential Role in Capillary Branching," *Circulation Research*, 94(2):262-268 (2004).

\* cited by examiner

US 7,828,840 B2

MEDICAL DEVICES AND METHODS FOR LOCAL DELIVERY OF ANGIOTENSIN II TYPE 2 RECEPTOR ANTAGONISTS

RELATED APPLICATIONS

The present patent document claims the benefit of the filing date under 35 U.S.C. §119(e) of Provisional U.S. Patent Application Ser. No. 61/003,192, filed Nov. 15, 2007, which is hereby incorporated by reference.

TECHNICAL FIELD

This invention relates generally to human and veterinary medical devices and, more particularly, to implantable medical devices incorporating angiotensin (Ang) II receptor antagonist compounds and especially angiotensin II type 2 ($AT_2$) receptor antagonist compounds. The invention also relates to methods of treatment and kits and to treating an aorta wall adjacent to an aortic aneurysm as a preventative measure.

BACKGROUND

Diseases of aorta are common in the general population and may include endovascular disease, including aneurysms and aortic dissections.

Endovascular disease may be characterized by weakened vessels due to elastin breakdown, which results in dilation of vessels and aneurysm. An aneurysm is a sac formed by localized dilatation of the wall of an artery, a vein, or the heart. Common areas where aneurysms occur and cause adverse medical conditions include the coronary arteries, the carotid arteries, various cerebral arteries, and the thoracic and abdominal aorta as well as iliac and femoral arteries. When a local dilatation of a vessel occurs, irregular blood flow patterns result in the lumen of the vessel, sometimes leading to clot formation. Typically, the wall of the vessel also progressively dilates and weakens, often resulting in vessel rupture. Vessel rupture, in turn, often causes dramatic negative consequences such as a stroke, when a cerebral vessel ruptures, or even death, when an abdominal aortic aneurysm ("AAA") ruptures. Continued degeneration can result in an increase in aneurysm size due to thinning of the medial connective tissue of the aorta and loss of elastin.

Aortic dissections occur when the inner layer of the aorta's artery wall splits open (dissects). The normal aorta contains collagen, elastin, and smooth muscle cells that contribute to the intima, media, and adventitia, which are the layers of the aorta. Hypertension with aging is believed to contribute to degenerative changes that may lead to breakdown of the collagen, elastin, and smooth muscle cells and ultimately dissection of the aorta. Aortic dissection is more likely to occur where pressure on the artery wall from blood flow is high, such as the proximal aorta or the ascending aorta (the first segment of the aorta). When the aortic wall splits, the pulses of blood can penetrate the artery wall and its inner layer, causing the aorta to tear or split further. This tear usually continues distally (away from the heart) down the descending aorta and into its major branches. Less often, the tear may run proximally (back toward the heart). Aortic dissection can also start in the descending (distal) segment of the aorta.

In light of these consequences, improved devices and methods of treating and/or preventing aneurysms and aortic dissections are constantly being sought. Although the following discussion focuses on AAA treatment and prevention, it is equally applicable to endovascular disease in other locations, and aortic dissections.

Various implantable medical devices are advantageously inserted within various portions of the body. Minimally invasive techniques and instruments for placement of intraluminal medical devices have been developed to treat and repair undesirable conditions within body vessels including treatment of conditions that affect blood flow such as abdominal aortic aneurysm. Various percutaneous methods of implanting medical devices within the body using intralumenal transcatheter delivery systems can be used to treat a variety of such conditions. One or more intralumenal medical devices, such as tubular stent grafts, can be introduced to a point of treatment within a body vessel using a delivery catheter device passed through the vasculature communicating between a remote introductory location and the implantation site, and released from the delivery catheter device at the point of treatment within the body vessel. Intralumenal medical devices can be deployed in a body vessel at a point of treatment and the delivery device subsequently withdrawn from the vessel, while the medical device is retained within the vessel to provide sustained improvement in valve function or to increase vessel patency. For example, an implanted stent graft can improve vessel function by permitting relatively less turbulent fluid flow through the stent graft conduit bridging the site of an aneurysm.

SUMMARY

In one embodiment, the invention provides a medical device and an angiotensin 1 type 2 ($AT_2$) receptor antagonist compound(s), the medical device being adapted to release the $AT_2$ receptor antagonist compound within a body of a patient.

The implantable medical device may be an endolumenal medical device such as a stent, the $AT_2$ receptor antagonist compound releasably associated with the stent. The stent may comprise a plurality of interconnected struts and bends, the $AT_2$ receptor antagonist compound releasably associated with the struts, bends, or a combination thereof. Alternatively, the stent may comprise a plurality of Z-STENTS®. The implantable medical device may be a stent graft comprising a support frame attached to a flexible tubular covering, the $AT_2$ receptor antagonist compound releasably associated with at least a portion of the stent graft. The medical device may also include at least one surface adapted for contact with a body vessel wall and comprising the $AT_2$ receptor antagonist compound coated on at least a portion of the at least one surface. The medical device may further include an elongated member having an ablumenal surface and a lumenal surface defining a cylindrical lumen extending longitudinally along the length of the elongated member. The $AT_2$ receptor antagonist compound may be releasably associated with at least a portion of at least one surface of the elongated member. For example, the implantable medical device may be configured as a stent graft having an elongated member configured as a flexible tubular covering forming at least a portion of the ablumenal surface that also includes a radially expandable support frame comprising a plurality of hoops attached to the elongated member. The cylindrical lumen may form a fluid conduit defined by the lumenal surface. The $AT_2$ receptor antagonist compound may be releasably associated with at least a portion of the ablumenal surface of the elongated member. The implantable medical device may also be a coated stent comprising a plurality of interconnected struts and bends, with a coating comprising the $AT_2$ receptor antagonist compound releasably associated with at least one strut, bend, or a combination thereof. The coating may comprise one or more layers containing the $AT_2$ receptor antagonist compound and a bioabsorbable polymer. The layers may include varying amounts of the $AT_2$ receptor antagonist compound(s). The implantable medical device may also be a graft comprising an $AT_2$ receptor antagonist compound. The $AT_2$ receptor antagonist compound may be contained within a reservoir, a well or a groove. Alternatively, the $AT_2$ receptor antagonist compound may be in or disposed on a separate carrier layer.

In another embodiment, the invention provides a method of treating an aneurysm or an aortic dissection including providing the medical device of this invention.

In yet another embodiment, the invention provides a method for preventing an aortic dissection including providing the medical device of this invention.

In yet another embodiment, the invention provides a method of treating an aneurysm or an aortic dissection comprising radially expanding a medical device in a lumen with a balloon catheter, wherein the balloon catheter releases an $AT_2$ receptor antagonist compound.

In a further embodiment, the invention provides a kit including a medical device and a balloon catheter comprising $AT_2$ receptor antagonist compound.

DETAILED DESCRIPTION

Figure 1A:
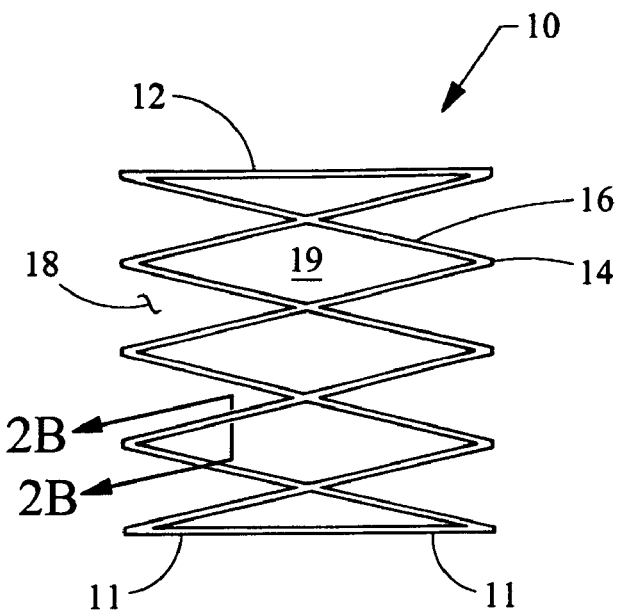
FIG. 1A is a side view of a coated expandable vascular stent endolumenal medical device.

The present disclosure describes medical devices, which comprise angiotensin (Ang) II receptor antagonist compounds and specifically angiotensin II type 2 ($AT_2$) receptor antagonist compounds and methods of using these medical devices to prevent and treat variety of diseases and conditions, including endovascular disease including aneurysms, such as aortic aneurysms; and aortic dissections. The medical device can be configured to provide a disease treatment by providing an effective amount of an $AT_2$ receptor antagonist compound proximate to a disease site within a body vessel. For example, the medical device can release or retain an $AT_2$ receptor antagonist at a desired rate within a blood vessel upon placement proximate to an aneurysm or aortic dissection. By providing $AT_2$ receptor antagonist with the device, the progression of local endovascular disease or aortic dissection may be mitigated, stopped and/or reversed, preventing further weakening and dilation of the vessel wall or splitting of the layers of aorta. These types of devices may be used for treatment or prevention of aneurysms, especially aortic abdominal aneurysms and for treatment or prevention of aortic dissections.

It is believed that the development, expansion and rupture of AAAs and aortic dissections are related to connective tissue destruction. For a discussion of this hypothesis, see for example, "Pharmacologic suppression of experimental abdominal aortic aneurysms: A comparison of doxycycline and four chemically modified tetracyclines," Curci, John A., Petrinec, Drazen, et al., *Journal of Vascular Surgery*, 28(6): 1082-1093 (December 1998). Connective tissue destruction, in turn, has been linked to the presence of a number of enzymes which break down components of blood vessel wall connective tissues, such as elastin. Examples of such "elastolytic" enzymes include serine proteinases and metalloproteinases (MMPs), which are derived from activated vascular cells and infiltrating inflammatory cells. It has been found that increased levels of some elastolytic enzymes are typically present in AAAs.

It is also believed that vascular remodeling depends in part on a balance between apoptosis and cell proliferation. For example, vascular remodeling in the process of development or in pathological states, such as aortic aneurysm, is thought to involve vascular smooth muscle cell (VSMC) apoptosis as a basic mechanism. Much of the recent emphasis in this field has focused on the renin-angiotensin system (RAS). Ang II is the principal vasoactive substance of the RAS, which has a variety of physiologic actions including vasoconstriction, aldosterone release, and cell growth. Ang II may also play a role in the regulation of cell growth and death via type 1 Ang II ($AT_1$) receptors and type 2 Ang II ($AT_2$) receptors. Specifically, most of the known physiologic actions of Ang II are thought to be mediated through the stimulation of $AT_1$ receptors. However, $AT_2$ receptors may also play a crucial role in vascular remodeling. $AT_2$ is expressed widely in fetal tissues, but its expression is diminished after birth. Interestingly, $AT_2$ is also induced in certain pathological conditions, such as inflammation and vascular injury.

Pharmacological inhibition of $AT_2$ may be desirable to stop and/or prevent further progression and/or development of a vascular disease, such as an aneurysm, and especially AAA, and aortic dissections and/or restore architecture of aortic tissues. By inhibiting $AT_2$ receptor signaling, VSMC apoptosis may be inhibited.

The following detailed description and appended drawings describe and illustrate various exemplary embodiments of the invention. The description and drawings serve to enable one skilled in the art to make and use the invention.

I. DEFINITIONS

The term "a" and "an" are used herein to refer to one or more than one (i.e., to at least one) of the grammatical object of the article. By way of example, "an element" means one element or more than one element.

The recitation of "about" or "substantially" used with reference to a quantity, such as an angle; level; value; dimension; size; or amount and includes variations in the recited quantity, level, value, dimension, size, or amount that are equivalent to the quantity, level, value, dimension, size, or amount recited, for instance an amount that is insubstantially different from a recited quantity, level, value, dimension, size for an intended purpose or function.

Unless otherwise indicated, the term "acyl" denotes a group containing the moiety C=O (and not being a carboxylic acid, ester or amide). Acyl includes C(O)—R, wherein R is hydrogen or an alkyl, alkenyl, alkynyl, aryl, heteroaryl or heterocyclyl residue, preferably a $C_{1-20}$ residue. Examples of acyl include formyl; straight chain or branched alkanoyl such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl, such as cyclopropylcarbonyl cyclobutylcarbonyl, cyclopentylcarbonyl and cyclohexylcarbonyl; aroyl, such as benzoyl, toluoyl and naphthoyl; aralkanoyl, such as phenylalkanoyl (e.g. phenylacetyl, phenylpropanoyl, phenylbutanoyl, phenylisobutarioyl, phenylpentanoyl and phenylhexanoyl) and naphthylalkanoyl (e.g. naphthylacetyl, naphthylpropanoyl and naphthylbutanoyl; aralkenoyl, such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl, such as phenoxyacetyl and phenoxypropionyl; aryithiocarbamoyl, such as phenylthiocarbamoyl; aryiglyoxyloyl, such as phenylglyoxyloyl and naphthylglyoxyloyl; arylsulfonyl, such as phenylsulfonyl and napthylsulfonyl; heterocycliccarbonyl; heterocyclicalkanoyl, such as thienylacetyl, thienylpropanoyl, thienylbutanoyl, thienylpentanoyl, thienyihexanoyl, thiazolylacetyl, thiadiazolylacetyl and tetrazolylacetyl; heterocyclicalkenoyl, such as heterocyclicpropenoyl, heterocyclicbutenoyl, heterocyclicpentenoyl and heterocyclichexenoyl; and heterocyclicglyoxyloyl, such as thiazolyglyoxyloyl and thienyiglyoxyloyl.

The term "adapted" refers to the ability of the medical device or any element(s) of the medical device to be changed or modified to allow the device to function is a specified manner. For example, the device may be adapted to release a therapeutic agent by coating the device with a coating layer comprising the therapeutic agent.

If a number of carbon atoms is not specified, the term "alkenyl," unless otherwise indicated, refers to a non-aromatic hydrocarbon radical, straight, branched or cyclic, containing from 2 to 10 carbon atoms and at least one carbon to carbon double bond. Preferably, one carbon to carbon double bond is present, and up to four non-aromatic carbon-carbon double bonds may be present. Thus, "$C_2$-$C_6$alkenyl" means an alkenyl radical having from 2 to 6 carbon atoms. Alkenyl groups include, but are not limited to, ethenyl, propenyl, butenyl, 2-methylbutenyl and cyclohexenyl. The straight, branched or cyclic portion of the alkenyl group may contain double bonds and may be substituted if a substituted alkenyl group is indicated.

As used herein, "alkenylene" refers to a straight, branched or cyclic, preferably straight or branched, bivalent aliphatic hydrocarbon group, preferably having from 2 to about 20 carbon atoms and at least one double bond, more preferably 2 to 12 carbons, even more preferably lower alkenylene. The alkenylene group is optionally substituted with one or more "alkyl group substituents." There may be optionally inserted along the alkenylene group one or more oxygen, sulfur or substituted or unsubstituted nitrogen atoms, where the nitrogen substituent is alkyl as previously described. Exemplary alkenylene groups include —CH=CH—CH=CH— and —CH=CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

The terms "alkoxy," "alkenoxy," "alkynoxy," "aryloxy," "heteroaryloxy," "heterocyclyloxy" and "acyloxy" respectively denote alkyl, alkenyl, alkynyl aryl, heteroaryl, heterocyclyl and acyl groups as herein defined when linked by oxygen.

"Alkoxy," unless otherwise indicated, represents either a cyclic or non-cyclic alkyl group attached through an oxygen bridge. "Alkoxy" therefore encompasses the definitions of alkyl and cycloalkyl below. For example, alkoxy groups include but are not limited to methoxy, oxy ethoxy, n-propyloxy, i-propyloxy, cyclopentyloxy and cyclohexyloxy.

As used herein, "alkyl" is intended to include both branched and straight-chain saturated aliphatic hydrocarbon group and may have a specified number of carbon atoms. For example, $C_1$-$C_{10}$, as in "$C_1$-$C_{10}$alkyl" is defined to include groups having 1, 2, 3, 4, 5, 6, 7, 8, 9 or 10 carbons in linear or branched arrangement. For example, "$C_1$-$C_{10}$alkyl" specifically includes, but is not limited to, methyl, ethyl, n-propyl, i-propyl, n-butyl, t-butyl, i-butyl, pentyl, hexyl, heptyl, octyl, nonyl, decyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulfur or substituted or unsubstituted nitrogen atoms, where the nitrogen substituent is alkyl as previously described. Exemplary alkylene groups include methylene (—CH$_2$—), ethylene (—CH$_2$CH$_2$), propylene (—(CH$_2$)$_3$—), cyclohexylene (—C$_6$H$_{10}$—), methylenedioxy (—O—CH$_2$—O—) and ethylenedioxy (—O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkylidene" refers to a bivalent group, such as =CR'R", which is attached to one atom of another group, forming a double bond. Exemplary alkylidene groups are methylidene (=CH$_2$) and ethylidene (=CHCH$_3$). As used herein, "arylalkylidene" refers to an alkylidene group in which either R' or R" is and aryl group. As used herein, "diarylalkylidene" refers to an alkylidene group in which R' and R" are both aryl groups. "Diheteroarylalkylidene" refers to an alkylidene group in which R' and R" are both heteroaryl groups.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$alkynyl" means an alkynyl radical having from 2 to 6 carbon atoms. Alkynyl groups include, but are not limited to, ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylenearyl. If aryl is taken to be phenyl, this definition would include phenyl itself as well as, for example, —CH$_2$Ph, —CH$_2$CH$_2$Ph, CH(CH$_3$)CH$_2$CH(CH$_3$)Ph.

As used herein, "alkynylene" refers to a straight, branched or cyclic, preferably straight or branched, bivalent aliphatic hydrocarbon group, preferably having from 2 to about 20 carbon atoms and at least one triple bond, more preferably 2 to 12 carbons, even more preferably lower alkynylene. The alkynylene group is optionally substituted with one or more "alkyl group substituents." There may be optionally inserted along the alkynylene group one or more oxygen, sulfur or substituted or unsubstituted nitrogen atoms, where the nitrogen substituent is alkyl as previously described. Exemplary alkynylene groups include —C≡C—C≡C—, —C≡C— and —C≡C—CH$_2$—. The term "lower alkynylene" refers to alkynylene groups having 2 to 6 carbons. Preferred alkynylene groups are lower alkynylene, with alkynylene of 3 to 4 carbon atoms being particularly preferred.

The term "alloy" refers to a substance composed of two or more metals or of a metal and a nonmetal intimately united, for example by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

As used herein, the term "antagonist" means an agent or a compound or plurality of compounds, chemical compositions, polymers, polypeptides, polynucleotides, etc., that decreases, inhibits, or modulates the biological activity of an AT$_2$ gene (Agtr2 gene) or an expression product thereof including an AT$_2$ receptor polypeptide. Examples of AT$_2$ receptor antagonists are provided below.

As used herein, the term "AT$_2$ receptor" means an Ang II type 2 (AT$_2$) receptor polypeptide that can bind Ang II and/or one or more other ligands. The term "AT$_2$ receptor" encompasses vertebrate homologs of AT$_2$ receptor family members, including, but not limited to, mammalian, reptilian and avian homologs. Representative mammalian homologs of AT$_2$ receptor family members include, but are not limited to, murine and human homologs.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

"Antigenic or immunogenic activity" refers to the ability of a polypeptide, fragment, variant or derivative thereof to produce an antigenic or immunogenic response in an animal, suitably a mammal, to which it is delivered, wherein the response includes the production of elements which specifically bind the polypeptide or fragment thereof.

As used herein, "aromatic" or "aryl" is intended to mean, unless otherwise indicated, any stable monocyclic or bicyclic carbon ring of up to 7 atoms in each ring, wherein at least one ring is aromatic. Examples of such aryl elements include, but are not limited to, phenyl, naphthyl, tetrahydronaphthyl, indanyl, biphenyl, phenanthryl, anthryl or acenaphthyl.

"Aralkyl" means alkyl as defined above which is substituted with an aryl group as defined above, e.g., —CH$_2$phenyl, —(CH$_2$)$_2$phenyl, —(CH$_2$)$_3$phenyl, —H$_2$CH(CH$_3$) CH$_2$phenyl, and the like and derivatives thereof.

As used herein, "arylene" refers to a monocyclic or polycyclic, preferably monocyclic, bivalent aromatic group, preferably having from 3 to about 20 carbon atoms and at least one aromatic ring, more preferably 3 to 12 carbons, even more preferably lower arylene. The arylene group is optionally substituted with one or more "alkyl group substituents." There may be optionally inserted around the arylene group one or more oxygen, sulfur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "arylidene" refers to an unsaturated cyclic bivalent group where both points of attachment are on the same atom of the ring. Exemplary arylidene groups include, but are not limited to, quinone methide moieties that have the formula:

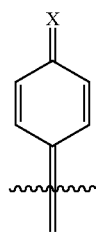

where X is O, S or NR'. "Heteroaiylidene" groups are arylidene groups where one or two, preferably two, of the atoms in the ring are heteroatoms, such as, but not limited to, O, S and N.

The term "bioabsorbable" is used herein to refer to materials selected to dissipate upon implantation within a body, independent of which mechanisms by which dissipation can occur, such as dissolution, degradation, absorption and excretion. The terms "bioabsorbable," "bioresorbable," or "biodegradable" are used synonymously herein, unless otherwise specified, to refer to the ability of the material or its degradation products to be removed by biological events, such as by fluid transport away from the site of implantation or by cellular activity (e.g., phagocytosis). Only the term "bioabsorbable" will be used in the following description to encompass absorbable, absorbable, bioabsorbable, and biodegradable, without implying the exclusion of the other classes of materials.

As used herein, recitation of a "non-bioabsorbable" material refers to a material, such as a polymer or copolymer, which remains in the body without substantial bioabsorption.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause an undesirably adverse, long-lived or escalating biological reaction or response, and is distinguished from a mild, transient inflammation which typically accompanies surgery or implantation of foreign objects into a living organism.

As used herein, the term "biological activity" means any observable effect resulting from the interaction between an AT$_2$ receptor polypeptide and a ligand. Representative, but non-limiting, examples of biological activity in the context of the present invention include association of an AT$_2$ receptor with a ligand, including an endogenous ligand such as Ang II or an $AT_2$ receptor antagonist. The term "biological activity" also encompasses both the inhibition and the induction of the expression of an $AT_2$ receptor polypeptide. Further, the term "biological activity" encompasses any and all effects resulting from the binding of a ligand by an $AT_2$ receptor polypeptide.

As used herein, the term "body vessel" means any body passage lumen that conducts fluid, including but not limited to blood vessels, esophageal, intestinal, billiary, urethral and ureteral passages.

The term "coating," as used herein and unless otherwise indicated, refers generally to material attached to a medical device. A coating can include material covering any portion of a medical device, and can be configured as one or more coating layers. A coating can have a substantially constant or a varied thickness and composition. Coatings can be adhered to any portion of a medical device surface, including the lumenal surface, the ablumenal surface, or any portions or combinations thereof.

As used herein, the phrase "controlled release" refers to the release of a therapeutic compound at a predetermined rate. A controlled release may be characterized by a drug elution profile, which shows the measured rate that the material is removed from a material-coated device in a given solvent environment as a function of time. A controlled release does not preclude an initial burst release associated with the deployment of the medical device, because in some embodiments of the invention an initial burst, followed by a more gradual subsequent release, may be desirable. The release may be a gradient release in which the concentration of the therapeutic compound released varies over time or a steady state release in which the therapeutic compound is released in equal amounts over a certain period of time (with or without an initial burst release).

When coated, the coating may be present on any portion of a surface of the device. In one embodiment, the surface is the inner surface. In another embodiment, the surface is the outer surface. In one embodiment, the layer covers at least about 10% of the surface. In another embodiment, the layer covers at least about 20% of the surface. In another embodiment, the layer covers at least about 30% of the surface. In another embodiment, the layer covers at least about 40% of the surface. In another embodiment, the layer covers at least about 50% of the surface. In another embodiment, the layer covers at least about 60% of the surface. In another embodiment, the layer covers at least about 70% of the surface. In another embodiment, the layer covers at least about 80% of the surface. In another embodiment, the layer covers at least about 90% of the surface. In another embodiment, the layer covers about 100% of the surface.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "cycloalkenyl" means a monocyclic unsaturated hydrocarbon group and may have a specified number of carbon atoms. For example, "cycloalkenyl" includes but is not limited to, cyclobutenyl, cyclopentenyl, 1-methylcyclopentenyl, cyclohexenyl and cyclohexadienyl.

Unless otherwise indicated, the term "cycloalkyl" or "aliphatic ring" means a monocyclic saturated aliphatic hydrocarbon group and may have a specified number of carbon atoms. For example, "cycloalkyl" includes, but is not limited to, cyclopropyl, methyl-cyclopropyl, 2,2-dimethyl-cyclobutyl, 2-ethyl-cyclopentyl, cyclohexyl.

By "derivative," as applied to peptides and polypeptides, refers to a peptide or polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions or deletions that provide for functional equivalent molecules.

By "effective amount," "therapeutic amount," or "therapeutically effective amount," in the context of treating or preventing a condition, is meant the delivery of that amount of active compound to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials but does not cause undesirable or intolerable side effects.

As used herein, "endolumenal" or "translumenal" refer to a device adapted for placement within a body vessel by procedures wherein the prosthesis is advanced within and through the lumen of a body vessel from a remote location to a target site within the body vessel. In vascular procedures, a medical device can typically be introduced "endovascularly" using a catheter over a wire guide under fluoroscopic guidance. The catheters and wire guides may be introduced through conventional access sites to the vascular system, such as through the femoral artery, or brachial and subclavian arteries, for access to the coronary arteries.

The terms "frame" and "support frame" are used interchangeably herein to refer to a structure that can be implanted, or adapted for implantation, within the lumen of a body vessel. In one embodiment, the frame may function as a stent.

The term "gene" as used herein refers to any and all discrete coding regions of the cell's genome, as well as associated non-coding and regulatory regions. The gene is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

The term "graft material" as used herein refers to a flexible material that can be attached to a support frame, for example to form a stent graft. A graft material can have any suitable shape, but preferably forms a tubular prosthetic vessel. A graft material can be formed from any suitable material, including the biologically derived or synthetic materials described herein.

The terms "halo" or "halogen" as used herein are intended to include chloro, fluoro, bromo and iodo.

"Heteroaralkyl" group means alkyl as defined above which is substituted with a heteroaryl group, e.g., —$CH_2$pyridinyl, —$(CH_2)_2$pyrimidinyl, —$(CH_2)_3$imidazolyl, and the like, and derivatives thereof.

The term "heteroaryl" or "heteroaromatic," as used herein, represents a stable monocyclic or bicyclic ring of up to 7 atoms in each ring, wherein at least one ring is aromatic and contains from 1 to 4 heteroatoms selected from the group consisting of 0, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, bezofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl.

Further examples of "heteroaryl" and "heterocyclyl" include, but are not limited to, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazoyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofliranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent may occur via a carbon atom or via a heteroatom.

As used herein, "heteroarylene," unless otherwise indicated, refers to a bivalent monocyclic or multicyclic ring system, preferably of about 3 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents. Exemplary heteroarylene groups include, for example, 1,4-iinidazolylene.

The term "heterocycle", "heteroaliphatic" or "heterocyclyl" as used herein is intended to mean a 5- to 10-membered nonaromatic heterocycle containing from 1 to 4 heteroatoms selected from the group consisting of 0, N and S, and includes bicyclic groups.

"Heterocyclylalkyl" group means alkyl as defined above which is substituted with a heterocycle group, e.g., —$CH_2$pyrrolidin-1-yl, —$(CH_2)_2$piperidin-1-yl, and the like, and derivatives thereof.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

The term "hydrocarbyl" as used herein includes any radical containing carbon and hydrogen including saturated, unsaturated, aromatic, straight or branched chain or cyclic, including polycyclic groups. Hydrocarbyl includes, but is not limited to, $C_1$-$C_8$alkyl, $C_2$-$C_8$alkenyl, $C_2$-$C_8$alkynyl, $C_3$-$C_{10}$cycloalkyl, aryl such as phenyl and naphthyl, Ar($C_1$-$C_8$)alkyl, such as benzyl, any of which may be optionally substituted.

The term "immuno-interactive" includes reference to any interaction, reaction, or other form of association between molecules and in particular where one of the molecules is, or mimics, a component of the immune system.

As used herein, the term "implantable" refers to an ability of a medical device to be positioned at a location within a body for any suitable period of time, such as within a body vessel. Furthermore, the terms "implantation" and "implanted" refer to the positioning of a medical device at a location within a body, such as within a body vessel. Implantable medical devices can be configured for transient placement within a body vessel during a medical intervention (e.g., seconds, minutes, hours), or to remain in a body vessel for a prolonged period of time after an implantation procedure (e.g., weeks or months or years). Implantable medical devices can include devices configured for bioabsorbtion within a body during a prolonged period of time.

The term "mixture" refers to a combination of two or more substances in which each substance retains its own chemical identity and properties.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably-linked" means that transcriptional and translational regulatory polynucleotides are positioned relative to a polypeptide-encoding polynucleotide in such a manner that the polynucleotide is transcribed and the polypeptide translated.

As used herein, the term "patient" means an animal (e.g., cow, horse, sheep, pig, chicken, turkey, quail, cat, dog, mouse, rat, rabbit or guinea pig), preferably a mammal such as a non-primate or a primate (e.g., monkey or human), most preferably a human.

The term "pharmaceutically acceptable carrier" or "carrier" includes any material which, when combined with $AT_2$ receptor antagonist, allows the $AT_2$ receptor antagonist compound to retain biological activity, such as the ability to decrease, inhibit, or modulate the biological activity of an Agtr2 gene or an expression product thereof including an $AT_2$ receptor polypeptide, and is non-reactive with the subject's immune system. Examples include, but are not limited to, any of the standard pharmaceutical carriers such as a phosphate buffered saline solution, water, emulsions such as oil/water emulsions, various polymer carrier materials, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

The terms "pharmaceutically compatible salt" and "pharmaceutically acceptable salt" are used interchangeably herein to refer to a salt which is toxicologically safe for human and animal administration. This salt may be selected from a group including hydrochlorides, hydrobromides, hydroiodides, sulfates, bisulfates, nitrates, citrates, tartrates, bitartrates, phosphates, malates, maleates, napsylates, fumarates, succinates, acetates, terephthalates, pamoates and pectinates. Pharmaceutically acceptable salts include both the metallic (inorganic) salts and organic salts; a non-exhaustive list of which is given in Remington's Pharmaceutical Sciences 17th Edition, pg. 1418 (1985). It is well known to one skilled in the art that an appropriate salt form is chosen based on physical and chemical stability, flowability, hydroscopicity and solubility.

"Phenylalkyl" means alkyl as defined above which is substituted with phenyl, e.g., —$H_2$phenyl, —$(CH_2)_2$phenyl, —$(CH_2)_3$phenyl, $CH_3CH(CH_3)CH_2$phenyl, and the like and derivatives thereof. Phenylalkyl is a subset of the aralkyl group.

The terms "polynucleotide variant" and "variant" refer to polynucleotides displaying substantial sequence identity with a reference polynucleotide sequence or polynucleotides that hybridize with a reference sequence under stringent conditions as known in the art (see for example Sambrook et al., Molecular Cloning. A Laboratory Manual", Cold Spring Harbor Press (1989)). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally-occurring allelic variants.

Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally occurring amino acid polymers.

As used herein, the terms "preventing" or "prophylaxis" include inhibiting formation of an aortic aneurysm and/or aortic dissection, in particular, abdominal aortic aneurysm and abdominal aortic dissection.

The term "prodrug" is used in its broadest sense and encompasses those compounds that are converted in vivo to an $AT_2$ receptor antagonist. Such compounds would readily occur to those of skill in the art.

As used herein, "pseudohalides" are groups that behave substantially similar to halides. Such groups can be used in the same manner and treated in the same manner as halides (X, in which X is a halogen, such as Cl or Br). Pseudohalides include, but are not limited to cyanide, cyanate, thiocyanate, selenocyanate, trifluoromethyl and azide.

As used herein, a "stent" is any structure that is used to hold tissue in place within a body, including an interior portion of a blood vessel, lymph vessel, ureter, bile duct or portion of the alimentary canal. A stent may be useful for opening up blood vessels, such as for example, an artery, vein or capillary thereby improving blood flow; keeping an artery, vein or capillary open; sealing any tears or openings in an artery, vein or capillary; preventing an artery, vein or capillary wall from collapsing or closing off again; or preventing small pieces of plaque from breaking off. In one embodiment, the stent is a stent graft.

A "stent graft," as used herein, refers to a support frame attached to a graft material. A stent graft can be any stent that is covered with a synthetic or natural (i.e., biologically-derived) material to form a graft prosthesis. The term also encompasses grafted stents, wherein the stent is covered in its entirety with a natural or synthetic graft material (e.g., Vanguard-graft stent, Palmaz-Impragraft stent or Corvita stent). In one embodiment, the stent graft is a prosthetic.

The term "substituted" and variants such as "optionally substituted" as used herein, unless otherwise indicated, mean that a substituent may be further substituted by one or more additional substituents, which may be optional or otherwise. Examples of additional substituents include $C_1$-$C_{10}$alkyl, $C_3$-$C_{10}$alkenyl, $C_3$-$C_{10}$alkynyl, aryl, —($C_1$-$C_4$alkyl)aryl, heterocyclyl, heteroaryl, $C_3$-$C_7$-cycloalkyl, $C_1$-$C_4$-perfluoroalkyl, —OH, —SH, —$HN_2$, nitrile, $C_1$-$C_{10}$-alkoxy, halo$C_{1-4}$alkyl, hydroxy$C_{1-4}$alkyl, $C_1$-$C_{10}$-alkylthio, —$CF_3$, halo (F, Cl, Br, I), —$NO_2$, —$CO_2R^{23}$, —$NH_2$, $C_1$-$C_4$alkylamino, $C_1$-$C_4$dialkylamino, arylamino, diarylamino, aryl$C_{1-4}$alkylamino, aryl$C_{1-4}$dialkylamino, aryloxy, aryl$C_{1-4}$alkyloxy, formyl, $C_{1-10}$alkylcarbonyl and $C_{1-10}$alkoxycarbonyl, —$PO_3H_2$, —$CO_2H$, —$CONHSO_2R^{21}$, —$CONHSO_2NHR^{20}$, —$NHCONHSO_2R^{21}$, —$NHSO_2R^{21}$, —$NHSO_2NHCOR^{21}$, —$SO_2NHR^{20}$, —$SO_2NHCOR^{21}$, —$SO_2NHCONHR^{20}$, —$SO_2NHCO_2R^{21}$, tetrazolyl, —CHO, —$CONH_2$, —NHCHO, —CO—($C_1$-$C_6$ perfluoroalkyl), $S(O)_r$($C_1$-$C_6$ perfluoroalkyl), wherein $R^{20}$ is H, $C_1$-$C_5$-alkyl, aryl, —($C_1$-$C_4$-alkyl)-aryl, heteroaryl; $R^{21}$ is aryl, $C_3$-$C_7$-cycloalkyl, $C_1$-$C_4$-perfluoroalkyl, $C_1$-$C_4$alkyl, optionally substituted with a substituent selected from the group consisting of aryl, heteroaryl, —OH, —SH, $C_1$-$C_4$-alkyl, $C_1$-$C_4$alkoxy, $C_1$-$C_4$alkylthio, —$CF_3$, halo, —$NO_2$, —$CO_2R^{23}$, —$NH_2$, $C_1$-$C_4$-alkylamino, $C_1$-$C_4$-dialkylamino, —$PO_3H_2$, or heteroaryl; and $R^{22}$ is selected from $C_1$-$C_6$-alkyl, $C_3$-$C_6$-cycloalkyl, aryl, —($C_1$-$C_5$-alkyl)-aryl, or heteroaryl.

The terms "therapeutic compound(s)," "active compound(s)," or "bioactive compounds" refer to the $AT_2$ receptor antagonists described herein, as well as, any other $AT_2$ receptor antagonists known to those skilled in the art.

As used herein, the term "treating" includes eradicating an aortic aneurysm and/or aortic dissection, in particular, abdominal aortic aneurysm and abdominal aortic dissection. In one embodiment, "treating" refers to minimizing the spread or minimizing the worsening of an aortic aneurysm and/or aortic dissection, in particular, an abdominal aortic aneurysm and abdominal aortic dissection.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In some embodiments, the vector may be a viral or viral-derived vector, which is operably functional in animal and preferably mammalian cells. Such vector may be derived from a poxvirus, an adenovirus or yeast. The vector can also include a selection marker, such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene, which confers resistance to the antibiotic hygromycin B.

II. AT$_2$ RECEPTOR ANTAGONIST COMPOUNDS

The present invention provides for local delivery of one or more of AT$_2$ receptor antagonist compounds proximate to a site of treatment within a body vessel by a medical device. One or more AT$_2$ receptor antagonist compounds may be provided for release from the medical device. The AT$_2$ receptor antagonist compound(s) may, for example, be included as part of at least a portion of the base material of the medical device itself; be contained within a reservoir, a well or a groove or be within a carrier material deposited on at least a portion of the medical device, or as a separate layer deposited on at least a portion of the medical device (the layer may optionally be over coated with another layer) or on at least a portion of the medical device that has been coated with a primer layer for increased adhesion, or be within the hollow walls of the device, or any combination of these. The AT$_2$ receptor antagonist compound may also be included in a separate carrier layer (or a multi-layered structure) that may be placed between elements of the medical device. For example, the separate layer may be placed between a stent and a graft material.

In certain embodiments, the release of the AT$_2$ receptor antagonist compound from the medical device depends, in part, upon the composition and configuration of the carrier material and/or the coating layer(s).

A. Illustrative AT$_2$ Receptor Antagonists

It is believed that AT$_2$ receptor antagonists may be effective in the treatment or prophylaxis of aortic aneurysms and/or aortic dissections.

Accordingly, the present invention provides methods useful for treating or preventing an aortic aneurysm and/or aortic dissection, comprising implanting into a patient in need thereof a medical device (e.g., a stent) and a therapeutically effective amount of AT$_2$ receptor antagonist.

The AT$_2$ receptor antagonist is an antagonist to one of the two main subtypes of Ang II receptors, namely Ang II type 2 receptor (A. T. Chiu et al., *Biochem. Biophys. Res. Commun.* 165:196-203 (1989)). The other receptor is Ang II type 1 (AT$_1$) receptor. Without being bound by any particular mechanism, the AT$_2$ receptor antagonist may hinder the binding of Ang II to the AT$_2$ receptor binding site or reduce the signaling by the receptor to its effector molecules, such as the coupled G-proteins, in the signal transduction cascade.

AT$_2$ receptor antagonist may be any molecule, active compound that binds to the AT$_2$ receptor subtype and that suitably modulates, decreases, or inhibits the effects of Ang II signaling through this receptor, including pharmaceutically compatible salts of the molecule or active compound. This category includes compounds showing differing structural features.

In one embodiment, the AT$_2$ receptor antagonist may be selected from the compounds listed in U.S. Pat. No. 5,789, 415, which is incorporated by reference herein in its entirety. For example, AT$_2$ receptor antagonist may be a compound, or its pharmaceutically acceptable salt, having the Formula (I):

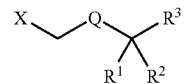

wherein:

Q is naphthyl, a 5 to 7 member heterocycle having from 1 to 3 atoms independently selected from nitrogen, oxygen and sulfur, or an 8 to 11 member heterobicycle having from 1 to 4 atoms selected from nitrogen, oxygen and sulfur, said heterocycle or heterobicycle being saturated, partially saturated or unsaturated and said naphthyl, heterocycle or heterobicycle optionally substituted with 1 to 4 W$^1$ substituents;

each W$^1$ substituent is independently selected from halo, hydroxy, nitro, cyano, C$_1$ to C$_8$ alkyl, C$_3$ to C$_7$ cycloalkyl, C$_1$ to C$_7$ alkoxy, amino, C$_1$ to C$_7$ alkylamino, di(C$_1$ to C$_7$ alkyl) amino, C$_1$ to C$_7$ alkylthio, C$_1$ to C$_7$ alkylsulfinyl, C$_1$ to C$_7$ alkylsulfonyl, —CONRR, —COOR and phenyl, said alkyl, cycloalkyl, alkoxy, alkylamino, dialkylamino, alkylthio, alkylsulfinyl and alkylsulfonyl optionally substituted with 1 or more W$^2$ substituents, and said phenyl optionally substituted with 1 or more W$^3$ substituents;

each R is independently hydrogen or C$_1$ to C$_8$ alkyl, said alkyl optionally substituted with 1 or more W$^2$ substituents;

each W$^2$ substituent is independently selected from halo, hydroxy, OXO, C$_3$ to C$_7$ cycloalkyl, C$_1$ to C$_7$ alkoxy, acyloxy, phenyl and 5 to 7 member heterocycle having 1 to 3 atoms selected from nitrogen, oxygen and sulfur, said phenyl and heterocycle optionally substituted with 1 or more W$^3$ substituents;

each W$^3$ substituent is independently selected from halo, hydroxy, nitro, C$_3$ to C$_7$ cycloalkyl, C$_1$ to C$_7$ alkoxy, amino, C$_1$ to C$_7$ alkylamino, di(C$_1$ to C$_7$ alkyl)amino, C$_1$ to C$_7$ alkylthio, C$_1$ to C$_7$ alkylsulfinyl and C$_1$ to C$_7$ alkylsulfonyl;

R$^1$ and R$^2$, when taken separately, are each independently selected from hydrogen, hydroxy, C$_1$ to C$_{10}$ alkyl, C$_1$ to C$_7$ alkylthio, C$_1$ to C$_7$ alkylsulfinyl, C$_1$ to C$_7$ alkylsulfonyl, phenyl and 5 to 7 member heterocycle or 8 to 11 member heterobicycle, having 1 to 3 atoms selected from nitrogen, oxygen and sulfur, said alkyl, alkylthio, alkylsulfinyl and alkylsulfonyl optionally substituted with 1 or more $W^4$ substituents, said phenyl and said heterocycle and heterobicycle optionally substituted with 1 to 5 $W^3$ substituents, wherein the $W^3$ substituents are as defined above, and said heterocycle being saturated, partially saturated or unsaturated, provided that $R^1$ and $R^2$ are not both hydroxy;

$R^1$ and $R^2$, when taken together with the carbon atom to which they are attached, form a $C_3$ to $C_7$ carbocyclic, $C_7$ to $C_{11}$ carbobicyclic, 3 to 7 member heterocyclic group having from 1 to 3 atoms independently selected from nitrogen, oxygen and sulfur, or a 7 to 11 member heterobicyclic group having from 1 to 4 atoms independently selected from nitrogen, oxygen and sulfur, said carbocyclic, carbobicyclic, heterocyclic or heterobicyclic group being saturated, partially saturated or unsaturated and optionally substituted with 1 or more $W^5$ substituents;

each $W^4$ substituent is independently selected from halo, $C_3$ to $C_8$ cycloalkyl, phenyl and 5 to 7 member heterocycle having 1 to 3 atoms selected from nitrogen, oxygen and sulfur, said phenyl and heterocycle optionally substituted with 1 or more substituents independently selected from halo, hydroxy, nitro, $C_1$ to $C_{10}$ alkyl, $C_3$ to $C_7$ cycloalkyl, $C_1$ to $C_7$ alkoxy, amino, $C_1$ to $C_7$ alkylamino and di($C_1$ to $C_7$ alkyl)amino;

each $W^5$ substituent is independently selected from halo, hydroxy, nitro, cyano, oxo, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl, $C_1$ to $C_7$ alkylsulfonyl, —CONRR, —COOR and phenyl, said alkyl, cycloalkyl, alkoxy, alkylamino, dialkylamino, alkylthio, alkylsulfinyl and alkylsulfonyl groups optionally substituted with 1 or more $W^2$ substituents, and said phenyl optionally substituted with 1 or more $W^3$ substituents, wherein the $W^3$ substituents are as defined above;

$R^3$ is —$(CH_2)_n COR^4$, tetrazolyl, $C_1$ to $C_5$ alkyltetrazolyl, triazolyl, $C_1$ to $C_5$ alkyltriazolyl, —$(CH_2)_n CH_2OH$, —$SO_2R^4$, —$SO_2NR^5R^6$ or —$NHSO_2R^7$;

$R^4$ is hydrogen, hydroxy, —$NHSO_2R^7$, $C_1$ to $C_{10}$ alkoxy, $C_1$ to $C_7$ alkylthio, —$NR^5R^6$, —$NHSO_2R^7$ or —OY, said alkoxy and alkylthio groups optionally substituted with 1 or more $W^6$ substituents;

n is an integer from 0 to 5;

Y is a pharmaceutically acceptable cation or a group hydrolyzable under physiological conditions;

$R^5$ and $R^6$, when taken separately, are each independently hydrogen, hydroxy, cyano, $C_1$ to $C_{10}$ alkyl, $C_1$ to $C_8$ alkoxy, —COR, —CONRR, —COOR, phenoxy, —CO($C_6H_5$) or 5 to 6 member heterocycle having 1 to 4 atoms selected from nitrogen, oxygen and sulfur, wherein R is as defined above, said alkyl optionally substituted with 1 or more $W^3$ substituents, wherein the $W^3$ substituents are as defined above, said —CO($C_6H_5$) optionally substituted with 1 to 3 $W^6$ substituents and said heterocycle optionally substituted with 1 or more $W^5$ substituents, wherein the $W^5$ substituents are as defined above;

$R^5$ and $R^6$, when taken together with the nitrogen atom to which they are attached, form a 3 to 7 member ring having 1 to 3 nitrogen atoms and from 0 to 3 atoms selected from oxygen and sulfur, said ring being saturated, partially saturated or unsaturated and optionally substituted with 1 or more $W^1$ substituents, wherein the $W^1$ substituents are as defined above;

$R^7$ is $C_1$ to $C_{10}$ alkyl or phenyl, said alkyl optionally substituted with 1 or more $W^6$ substituents, and said phenyl optionally substituted with 1 or more $W^3$ substituents, wherein the $W^3$ substituents are as defined above;

X is an azacyclic group of the formula

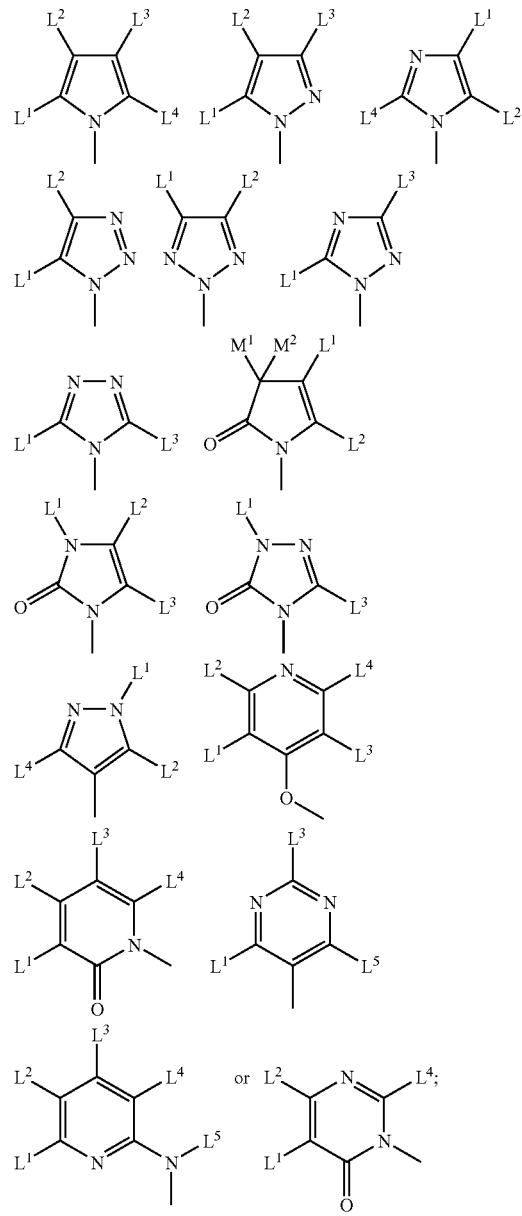

$L^1$, $L^2$, $L^3$, $L^4$ and $L^5$, when taken separately, are independently hydrogen, halo, nitro, $C_1$ to $C_6$ alkyl, $C_3$ to $C_7$ cycloalkyl, polyfluoro-$C_1$ to $C_4$ alkyl, aryl, heteroaryl, tetrazol-5-yl, —$COR^8$, —$CO_2R^8$, —$CONHSO_2R^9$, —$CONR^{10}R^{10}$, —$CONH$(tetrazol-5-yl), —$OR^9$, —$OCONR^9R^{11}$, —$NR^8R^9$, —$NHCOR^9$, —$NHCO_2R^9$, —$NHCONR^8R^9$, —$NHSO_2R^9$, —$NHSO_2NR^9R^{11}$, —$NHSO_2$-polyfluorophenyl, —$SR^9$, —$SOR^9$, —$SO_2R^9$, —$SO_2NHCN$, —$SO_2NR^{11}R^{12}$, —$SO_2NHCOR^9$, —$SO_2NH$-heteroaryl, —$PO(OR^8)_2$ or —$PO(OR^8)R^{11}$, said alkyl, cycloalkyl, aryl and heteroaryl groups optionally substituted with 1 or more substituents selected from hydroxy, halo, $C_1$ to $C_4$ perfluoroalkyl, $C_1$ to $C_4$ alkoxy, aryl, heteroaryl, guanidino, morpholino, tetrazol-5-yl, —$COR^8$, —$CO_2R^8$, —$CONHSO_2R^9$, —$CONR^8R^8$, —O—$COR^8$, —$NR^8R^8$, —$NR^{12}COOR^9$, —$N(C_1$ to $C_6$ alkyl)piperazine, —$SR^9$, —SOR⁹, —SO₂R⁹, —SO₂NR⁸CN, —SO₂NR⁸COR⁹, —SO₂NR⁸-heteroaryl, —PO(OR⁸)₂ and —PO(OR⁸)R¹³;

$L^1$ and $L^2$, $L^2$ and $L^3$, $L^3$ and $L^4$ or $L^4$ and $L^5$, when taken together with the azacyclic group to which they are attached, form a fused 8 to 11 member azabicyclic system having 1 to 5 nitrogen atoms and 0 to 3 atoms selected from oxygen and sulfur, said azabicyclic system optionally substituted with 1 to 3 $W^6$ substituents;

each $W^6$ substituent is independently halo, nitro, cyano, $C_1$ to $C_6$ alkyl, $C_3$ to $C_7$ cycloalkyl, polyfluoro-$C_1$ to $C_4$ alkyl, aryl, heteroaryl, tetrazol-5-yl, —COR⁸, —CO₂R⁸, —CONR⁸SO₂R⁹, —CONR⁹R¹⁰, —CONR⁸(tetrazol-5-yl), —OR⁹, —OCONR⁹R¹¹, —NR⁸R⁹, —NR⁸COR⁹, —NR⁸CO₂R⁹, —NR⁸CONR⁸R⁹, —NR⁸SO₂R⁹, —NR⁸SO₂NR⁹R¹¹, —NR⁸SO₂-polyfluorophenyl, —SR⁹, —SOR⁹, —SO₂R⁹, —SO₂NR⁸CN, —SO₂NR⁹R¹², —SO₂NR⁸COR⁹, —SO₂NR⁸-heteroaryl, —PO(OR⁸)₂ or —PO(OR⁸)R¹¹, said alkyl, cycloalkyl, aryl and heteroaryl groups optionally substituted with 1 or more substituents selected from hydroxy, halo, $C_1$ to $C_4$ perfluoroalkyl, $C_1$ to $C_4$ alkoxy, aryl, heteroaryl, guanidino, morpholino, tetrazol-5-yl, —COR⁸, —CO₂R⁸, —CONR⁸SO₂R⁹, —CONR⁸R⁹, —O—COR⁸, —NR⁸R⁹, —NR¹²COOR⁹, —N($C_1$ to $C_6$ alkyl)piperazine, —SR⁹, —SOR⁹, —SO₂R⁹, —SO₂NR⁸CN, —SO₂NR⁸COR⁹, —SO₂NR⁸-heteroaryl, —PO(OR⁸)₂ and —PO(OR⁸)R¹³;

each $R^8$ is independently hydrogen, $C_1$ to $C_6$ alkyl, $C_3$ to $C_7$ cycloalkyl, aryl, heteroaryl or aryl($C_1$ to $C_6$)alkyl;

each $R^9$ is independently hydrogen, $C_1$ to $C_{10}$ alkyl, $C_3$ to $C_7$ cycloalkyl, aryl, heteroaryl or polyfluoro($C_1$ to $C_4$)alkyl, said alkyl and cycloalkyl optionally substituted with 1 or more substituents selected from halo, hydroxy, nitro, $C_1$ to $C_4$ alkoxy, $C_1$ to $C_4$ alkylthio, —CO₂R¹², amino, $C_1$ to $C_4$ alkylamino, di($C_1$ to $C_4$)alkylamino, aryl, heteroaryl, —SH, —PO₃H₂, —P(O)(OH)(O—$C_1$ to $C_4$ alkyl), P(O)(OR⁸)(R¹¹) or P(O)(OR¹⁴)(R¹⁵);

each $R^{10}$ is independently hydrogen, $C_1$ to $C_5$ alkyl, aryl or —CH₂-aryl;

each $R^{11}$ is independently hydrogen, $C_1$ to $C_5$ alkyl, $C_3$ to $C_7$ cycloalkyl, aryl or —CH₂-aryl;

each $R^{12}$ is hydrogen or $C_1$ to $C_4$ alkyl;

each $R^{13}$ is independently hydrogen, $C_1$ to $C_5$ alkyl, C2 to $C_4$ alkenyl, $C_1$ to $C_4$ alkoxy($C_1$ to $C_4$)alkyl or benzyl, said benzyl optionally substituted with 1 or more substituents independently selected from hydroxy, amino, nitro and methoxy;

$R^{14}$ and $R^{15}$ are taken together and form a 5 to 7 member ring having 1 to 3 atoms independently selected from nitrogen, oxygen and sulfur;

$M^1$ and $M^2$ are taken together and are —(CH₂)$_m$; and m is an integer from 3 to 7.

AT₂ receptor antagonists may include compounds of Formula (I) wherein X is:

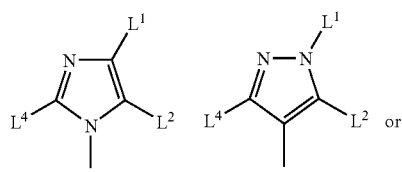

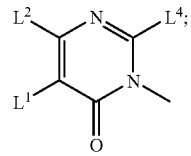

$L^1$, $L^2$ and $L^4$ are as defined above;

Q is thiophene, pyridine, pyrimidine, naphthyl, benzofuran or any of the foregoing substituted with 1 or 2 $W^1$ substituents;

$R^1$ and $R^2$ are taken together as defined above;

$R^3$ is —(CH₂)$_n$COR⁴;

n is 0 or 1;

$R^4$ is hydrogen, hydroxy or —OY;

Y is a pharmaceutically acceptable cation or a group hydrolyzable under physiological conditions; and each $W^1$ is independently halo, hydroxy, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, —CONRR or —COOR, wherein R is as defined above.

Additional examples include compounds wherein X, Q, $R^3$, $R^4$, n and Y are as defined immediately above and wherein:

$R^1$ and $R^2$ are taken together and form a $C_5$ to $C_6$ carbocyclic, $C_8$ to $C_{10}$ carbobicyclic or 5 to 7 member heterocyclic group having 1 or 2 atoms independently selected from nitrogen, oxygen and sulfur, said carbocyclic, carbobicyclic or heterocyclic group being saturated, partially saturated or unsaturated;

$L^1$ and $L^2$, when taken separately, are each independently hydrogen, halo, $C_1$ to $C_6$ alkyl, $C_3$ to $C_7$ cycloalkyl, polyfluoro-$C_1$ to $C_4$ alkyl or —CO₂R⁸;

$L^1$ and $L^2$, when taken together with the azacyclic group to which they are attached, form a fused 8 to 10 member azabicyclic system having 2 to 4 nitrogen atoms, said azabicyclic system optionally substituted with 1 to 3 $W^6$ substituents;

$L^4$ is $C_1$ to $C_4$ alkyl, $C_3$ to $C_5$ cycloalkyl or $C_1$ to $C_3$ alkoxy;

$R^8$ is hydrogen, $C_1$ to $C_6$ alkyl or $C_3$ to $C_7$ cycloalkyl; and each $W^6$ is independently halo, $C_1$ to $C_6$ alkyl, $C_3$ to $C_7$ cycloalkyl, polyfluoro-$C_1$ to $C_4$ alkyl, —CO₂R⁸, amino, $C_1$ to $C_6$ alkylamino, di($C_1$ to $C_6$)alkylamino, acylamino or diacylamino.

Among the particularly preferred compounds defined above are those having the structure

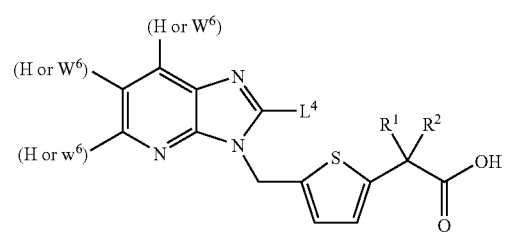

wherein:

$L^4$ is $C_1$ to $C_4$ alkyl or $C_3$ to $C_5$ cycloalkyl;

each $W^6$ is independently $C_1$ to $C_6$ alkyl, amino, $C_1$ to $C_6$ alkylamino, di($C_1$ to $C_6$)alkylamino, acylamino or diacylamino; and $R^1$ and $R^2$ are taken together and form cyclopentane, cyclohexane, cyclopentene, tetrahydropyran or indan, for example:

1-[5-(2-ethyl-5,7-dimethylimidazo[4,5-b]pyridin-3-ylmethyl)thiophen-2-yl]-cyclopent-3-ene carboxylic acid;

1-[5-(5,7-dimethyl-2-propylimidazo[4,5-b]pyridin-3-ylmethyl)thiophen-2-yl]cyclopent-3-ene carboxylic acid;

1-[5-(2-cyclopropyl-5,7-dimethylimidazo[4,5-b]pyridin-3-ylmethyl)thiophen-2-yl]cyclopent-3-ene carboxylic acid;

1-[5-(2-cyclopropyl-5,7-dimethylimidazo[4,5-b]pyridin-3-ylmethyl)thiophen-2-yl]cyclopentane carboxylic acid;

4-[5-(2-ethyl-5,7-dimethylimidazo[4,5-b]pyridin-3-ylmethyl)thiophen-2-yl]tetrahydropyran-4-carboxylic acid;

2-[5-(2-ethyl-5,7-dimethylimidazo[4,5-b]pyridin-3-ylmethyl)thiophen-2-yl]indan-2-carboxylic acid;

2-[5-(2-cyclopropyl-5,7-dimethylimidazo[4,5-b]pyridin-3-ylmethyl)thiophen-2-yl]indan-2-carboxylic acid;

1-[5-(2-ethyl-5,7-dimethylimidazo[4,5-b]pyridin-3-ylmethyl)thiophen-2-yl]cyclohexane carboxylic acid; and 1-[5-(2-cyclopropyl-5,7-dimethylimidazo[4,5-b]pyridin-3-ylmethyl)thiophen-2-yl]cyclohexane carboxylic acid.

Also among the particularly preferred compounds defined above are those having the structure

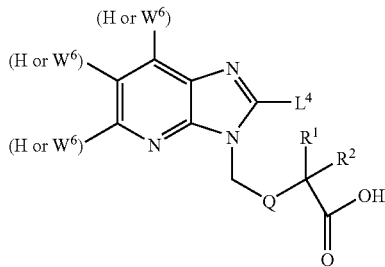

wherein:
Q is:

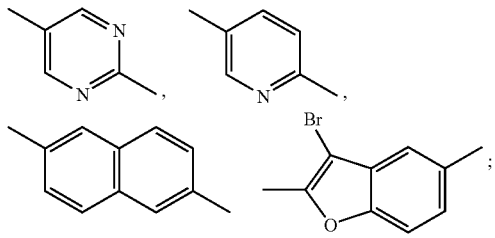

$L^4$ is $C_1$ to $C_4$ alkyl or $C_3$ to $C_5$ cycloalkyl; and $R^1$ and $R^2$ are taken together and are —CH$_2$CH$_2$CH$_2$CH$_2$— or —CH$_2$CH=CHCH$_2$—, for example:

1-[5-(2-ethyl-5,7-dimethylimidaz[4,5-b]pyridin-3-ylmethyl)pyridin-2-yl]cyclopentane carboxylic acid;

1-[5-(2-cyclopropyl-5,7-dimethylimidazo[4,5-b]pyridin-3-ylmethyl)pyridin-2-yl]cyclopentane carboxylic acid;

1-[2-(2-ethyl-5,7-dimethylimidazo[4,5-b]pyridin-3-ylmethyl)pyrimidin-5-yl]cyclopent-3-ene carboxylic acid;

1-[2-(2-cyclopropyl-5,7-dimethylimidazo[4,5-b]pyridin-3-ylmethyl)pyrimidin-5-yl]cyclopent-3-ene carboxylic acid;

1-[6-(2-ethyl-5,7-dimethylimidazo[4,5-b]pyridin-3-ylmethyl)naphthalen-2-yl]cyclopent-3-ene carboxylic acid; and 1-[3-bromo-5-(2-ethyl-5,7-dimethylimidazo[4,5-b]pyridin-3-ylmethyl)benzofuran-2-yl]cyclopentane carboxylic acid.

Also among the particularly preferred compounds defined above are those having the structure

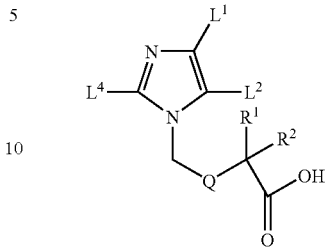

wherein:
Q is:

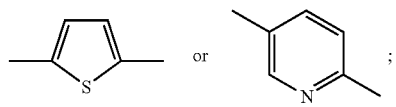

$L^1$ and $L^2$ are taken separately and are each independently halo, $C_1$ to $C_6$ alkyl or —CO$_2$H;

$L^4$ is $C_1$ to $C_4$ alkyl; and $R^1$ and $R^2$ are taken together and are —CH$_2$CH$_2$CH$_2$CH$_2$— or —CH$_2$CH=CHCH$_2$—, for example:

2-butyl-3-[5-(1-carboxycyclopent-3-enyl)thiophen-2-ylmethyl]-5-chloro-3H-imidazole-4-carboxylic acid;

3-[5-(1-carboxycyclopent-3-enyl)thiophen-2-ylmethyl]-5-ethyl-2-propyl-3H-imidazole-4-carboxylic acid; and 3-[5-(1-Carboxycyclopent-3-enyl)thiophen-2-ylmethyl]-5-chloro-2-propyl-3H-imidazole-4-carboxylic acid.

Also among the particularly preferred compounds defined above are those having the structure

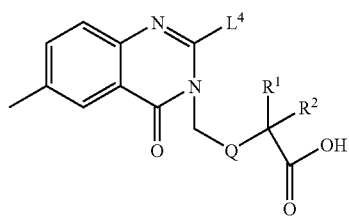

wherein:
Q is:

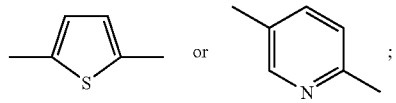

$L^4$ is $C_1$ to $C_4$ alkyl; and $R^1$ and $R^2$ are taken together and are —CH$_2$CH$_2$CH$_2$CH$_2$— or —CH$_2$CH=CHCH$_2$—, for example:

1-[5-(2-butyl-5-methyl-4-oxo-4H-quinazolin-3-ylmethyl)pyridin-2-yl]cyclopentane carboxylic acid; and 1-[5-(2-butyl-5-methyl-4-oxo-4H-quinazolin-3-ylmethyl)thiophen-2-yl]cyclopent-3-ene carboxylic acid.

Also among the compounds defined above are those having the structure

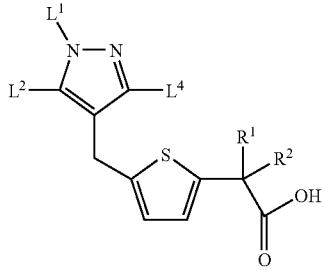

wherein:

$L^1$ and $L^2$ are taken separately and are each independently halo, $C_1$ to $C_6$ alkyl, polyfluoro-$C_1$ to $C_6$ alkyl or —$CO_2H$;

$L^4$ is $C_1$ to $C_4$ alkyl; and $R^1$ and $R^2$ are taken together and are —$CH_2CH_2CH_2CH_2$— or —$CH_2CH=CHCH_2$—, for example:

2,5-dibutyl-4-[5-(1-carboxycyclopent-3-enyl)thiophen-2-ylmethyl]-2H-pyrazole-3-carboxylic acid;

5-butyl-4-[5-(1-carboxycyclopent-3-enyl)thiophen-2-ylmethyl]-2-trifluoromethyl-2H-pyrazole-3-carboxylic acid; and 5-butyl-4-[5-(1-carboxycyclopent-3-enyl)thiophen-2-ylmethyl]-2-propyl-2H-pyrazole-3-carboxylic acid.

Other preferred compounds include compounds in the same general class as:

1-[5-(2-cyclopropyl-5,7-dimethylimidazo[4,5-b]pyridin-3-ylmethyl)thiophen-2-yl]cyclopenten-3-ene carboxylic acid benzenesulfonamide;

1-[5-(2-cyclopropyl-5,7-dimethylimidazo[4,5-b]pyridin-3-ylmethyl)thiophen-2-yl]cyclopenten-3-ene carboxylic acid p-toluenesulfonamide;

1-[5-(2-cyclopropyl-5,7-dimethylimidazo[4,5-b]pyridin-3-ylmethyl)thiophen-2-yl]cyclopenten-3-ene carboxylic acid methanesulfonamide; and 1-[5-(2-cyclopropyl-5,7-dimethylimidazo[4,5-b]pyridin-3-ylmethyl)thiophen-2-yl]cyclopenten-3-ene carboxylic acid trifluoromethanesulfonamide.

Various intermediates, particularly intermediates such as those described in the examples hereinbelow, for example, and their analogous alkyl and substituted alkyl esters are also included:

1-thiophen-2-yl-cyclopent-3-ene carboxylic acid ethyl ester;

1-(5-formylthiophen-2-yl)cyclopent-3-ene carboxylic acid ethyl ester;

1-(5-chloromethylthiophen-2-yl)cyclopent-3-ene carboxylic acid ethyl ester; and

1-[5-(2-ethyl-5,7-dimethylimidazo[4,5-b]pyridin-3-ylmethyl)thiophen-2-yl]cyclopent-3-ene carboxylic acid ethyl ester.

In yet another embodiment, the $AT_2$ receptor antagonist may be selected from 6-aminoquinazolinone compounds listed in U.S. Pat. No. 5,385,894, which is incorporated by reference herein in its entirety. U.S. Pat. No. 5,385,894 described methods for preparation of these from 6-aminoquinazolinone compounds. For example, the $AT_2$ receptor antagonist may be a compound of the general Formula (II):

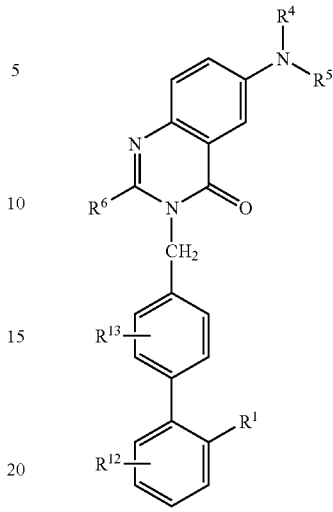

or a pharmaceutically acceptable salt thereof, wherein:

$R^1$ is (a) $CO_2R^2$, (b) tetrazol-5-yl, (c) $NHSO_2CF_3$, (d) $SO_2NHCOR^3$, or (e) $SO_2NH$-heteroaryl;

$R^2$ is (a) hydrogen, or (b) $C_1$-$C_6$ alkyl;

$R^3$ is (a) $C_1$-$C_6$ alkyl, (b) $C_3$-$C_7$ cycloalkyl, (c) phenyl, (d) substituted phenyl in which the substituent is F, Cl, Br, $C_1$-$C_4$ alkoxy, perfluoro $C_1$-$C_4$ alkyl, di-($C_1$-$C_4$-alkyl)amino, or $CO_2R^2$, (e) substituted $C_1$-$C_8$ alkyl in which the substituent is $C_3$-$C_7$ cycloalkyl, $C_1$-$C_4$ alkoxy, hydroxy, di-($C_1$-$C_4$ alkyl)amino, $CO_2R^2$, morpholinyl, $C_1$-$C_4$ alkylpiperazinyl, $CF_3$, thio, $C_1$-$C_4$ alkylsulfinyl, $C_1$-$C_4$ alkylsulfonyl, heteroaryl, $NH_2$, or aryl, or (f) heteroaryl;

$R^4$ is (a) $C_1$-$C_6$ alkyl, (b) substituted $C_1$-$C_6$ alkyl in which the substituent is $C_3$-$C_7$ cycloalkyl, $C_1$-$C_4$ alkoxy, hydroxy, di-($C_1$-$C_4$ alkyl)amino, $CO_2R^2$, morpholinyl, $C_1$-$C_4$ alkylpiperazinyl, $CF_3$, $C_1$-$C_4$ alkylthio, $C_1$-$C_4$ alkylsulfinyl, $C_1$-$C_4$ alkylsulfonyl, —CHO, $O(C_2$-$C_3$ alkyl-O—$)_nC_1$-$C_3$ alkyl where n=1-5, or $NHCO_2(C_1$-$C_6$-alkyl), (c) $C_2$-$C_6$ alkenyl, (d) phenyl $C_1$-$C_6$ alkyl, (e) substituted phenyl $C_1$-$C_6$ alkyl, in which the substituent on the phenyl group is hydroxy, $C_1$-$C_4$ alkoxy, F, Cl, I, Br, $NO_2$, cyano, $CO_2R^2$, di($C_1$-$C_4$ alkyl)amino, —Obenzyl, $CF_3$, phenyl-$C_1$-$C_4$-alkoxy, $C_1$-$C_4$ alkylthio, $C_1$-$C_4$-alkylsulfinyl, —OPO(O-benzyl)$_2$, or $C_1$-$C_4$ alkylsulfonyl, amino, $P(O)(OH)_2$, $C_1$-$C_4$ alkyl, —OPO(O—$C_1$-$C_6$ alkyl)$_2$, OPO(OH)$_2$, OCO(CH$_2$)$_2$COOH, OSO$_3$H, or O($C_2$-$C_3$ alkyl-O—$)_nC_1$-$C_3$ alkyl, (f) heteroaryl $C_1$-$C_6$ alkyl, or (g) substituted heteroaryl $C_1$-$C_6$ alkyl, in which the substituent on the heteroaryl group is F, Cl, $NO_2$, $CO_2R^2$, or di-($C_1$-$C_4$ alkyl)amino;

$R^5$ is (a) $CO_2R^7$, (b) $CONR^8R^9$, (c) $COR^{10}$, (d) $SO_2NR^8R^9$, or (e) $SO_2R^{10}$;

$R^6$ is (a) $C_1$-$C_6$ alkyl, (b) substituted $C_1$-$C_6$ alkyl in which the substituent is $C_3$-$C_7$ cycloalkyl, benzyl or $C_1$-$C_4$-alkoxy, (c) cyclopropyl;

$R^7$ is (a) $C_1$-$C_6$ alkyl, (b) substituted $C_1$-$C_6$ alkyl in which the substituent is $C_1$-$C_4$ alkoxy, hydroxy, di($C_1$-$C_4$ alkyl)amino, $CO_2R^2$, morpholinyl, $C_1$-$C_4$ alkylpiperazinyl, $C_1$-$C_4$ alkylsulfinyl, $C_1$-$C_4$ alkylsulfonyl, or O($C_2$-$C_3$ alkyl-O—$)_nC_1$-$C_3$ alkyl, (c) phenyl $C_1$-$C_6$ alkyl, (d) substituted phenyl $C_1$-$C_6$ alkyl, in which the substituent on the phenyl group is hydroxy, $C_1$-$C_4$ alkoxy, F, Cl, $NO_2$, cyano, $CO_2R_2$, di($C_1$-$C_4$ alkyl)amino, $CF_3$, phenyl $C_1$-$C_4$ alkoxy, $C_1$-$C_4$ alkylthio, $C_1$-$C_4$ alkylsulfinyl, $C_1$-$C_4$ alkylsulfonyl, or O($C_2$-$C_3$ alkyl-O—$)_nC_1$-$C_3$ alkyl, (e) heteroaryl $C_1$-$C_6$ alkyl, or (f)

substituted heteroaryl $C_1$-$C_6$ alkyl, in which the substituent on the heteroaryl group is F, Cl, $NO_2$, $CO_2R_2$, or di-($C_1$-$C_4$ alkyl)amino;

$R^8$ is (a) hydrogen, or (b) $C_1$-$C_6$ alkyl;

$R^9$ is (a) $C_1$-$C_6$ alkyl, or (b) substituted $C_1$-$C_6$ alkyl in which the substituent is $C_1$-$C_4$ alkoxy, hydroxy, di-($C_1$-$C_4$ alkyl)amino, $CO_2R^2$, morpholinyl, $C_1$-$C_4$ alkylpiperazinyl, $C_1$-$C_4$ alkylsulfinyl or $C_1$-$C_4$ alkylsulfonyl, (c) perfluoro $C_1$-$C_6$ alkyl, (d) phenyl, (e) heteroaryl, or $R^8$ and $R^9$ taken together are morpholino,

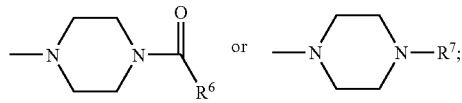

$R^{10}$ is (a) phenyl, (b) substituted phenyl in which the substituent is F, Cl, Br, I, $C_1$-$C_4$-alkoxy, $C_1$-$C_4$ alkyl, $NO_2$, cyano, $OC_6H_5$, $CO_2R^2$, di($C_1$-$C_4$ alkylamino), $CF_3$, $C_1$-$C_4$ alkylthio, $C_1$-$C_4$ alkylsulfinyl, $C_1$-$C_4$ alkylsulfonyl, —OPO($OC_1$-$C_6$-alkyl)$_2$, OPO(OH)$_2$, OPO(O-benzyl)$_2$, OCO($CH_2$)$_2$ COOH, $OSO_2$ OH, —PO($OC_1$-$C_6$— alkyl)$_2$, —PO(OH)$_2$, OBn, or O—($C_2$-$C_3$ alkyl-O)$_n$$C_1$-$C_3$ alkyl, (c) phenyl $C_1$-$C_6$ alkyl, (d) heteroaryl, (e) $C_1$-$C_6$ alkyl, (f) substituted $C_1$-$C_6$ alkyl in which the substituent is $C_3$-$C_7$ cycloalkyl, $C_1$-$C_4$ alkoxy, hydroxy, di-($C_1$-$C_4$ alkyl)amino, $CO_2R^2$, morpholinyl, $C_1$-$C_4$ alkylpiperazinyl, $CF_3$, thio, $C_1$-$C_4$ alkylsulfinyl, $C_1$-$C_4$ alkylsulfonyl, imidazolyl, —N($COC_1$-$C_6$ alkyl)piperazinyl, or N-aryl-piperazinyl, (g) substituted phenyl $C_1$-$C_6$ alkyl, in which the substituent on the phenyl group is hydroxy, $C_1$-$C_4$ alkoxy, F, Cl, $NO_2$, cyano, $CO_2R^2$, di($C_1$-$C_4$ alkyl)amino, $CF_3$, phenyl $C_1$-$C_4$ alkoxy, thio, $C_1$-$C_4$ alkylsulfinyl, or $C_1$-$C_4$-alkylsulfonyl, or (h) $C_{3-7}$ cycloalkyl.

$R^{11}$ is (a) hydrogen, (b) F, Cl, Br or I, (c) $C_1$-$C_4$ alkyl, (d) $C_1$-$C_4$ alkoxy, $R^{12}$ is (a) hydrogen, (b) $C_1$-$C_5$ alkyl, (c) phenyl, (d) substituted phenyl in which the substituent is $C_1$-$C_4$ alkoxy, F, Cl, $CO_2R^2$, di($C_1$-$C_4$ alkyl)amino, thio, $C_1$-$C_4$ alkylsulfinyl, $C_1$-$C_4$ alkylsulfonyl.

The term heteroaryl is an unsubstituted, monosubstituted or disubstituted five or six membered aromatic ring which contains 1 to 3 heteroatoms selected from O, S, or N and the substituents are selected from the group consisting of $C_1$-$C_4$ alkyl, F, Cl, $CO_2R^2$, or di-($C_1$-$C_4$ alkyl)amino.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The abbreviations defined in the table below are used in the specific embodiments which are illustrated in tabular form:

| Table of Abbreviations | |
|---|---|
| Me | methyl |
| Et | ethyl |
| Pr | n-propyl |
| iPr | isopropyl |
| cPr | cyclopropyl |
| Bu | n-butyl |
| iBu | isobutyl |
| tBu | tertbutyl |
| Pn | n-pentyl |

| Table of Abbreviations | |
|---|---|
| iPn | isopentyl |
| Hx/Hex | n-hexyl |
| chex | cyclohexyl |
| Boc | butyloxycarbonyl |
| Ph | phenyl |
| BHn | benzyl |
| Bz | benzoyl |
| TET | tetrazol-5-yl |

The $AT_2$ receptor antagonist may be a compound of the Formula (II) wherein $R^5$ is $CO_2R^7$ (Formula (IIa)).

In another embodiment, the $AT_2$ receptor antagonist may be a compound of the Formula (IIa) wherein:

$R^1$ is tetrazol-5-yl or $SO_2NHCOR^3$ or $NHSO_2CF_3$, $R^3$ is a) phenyl, b) substituted phenyl in which the substituent is F, Cl, Br, I or $C_1$-$C_4$ alkoxy, c) $C_1$-$C_8$ alkyl substituted with di-($C_1$-$C_4$-alkyl)amino or $NH_2$, or d) $C_3$-$C_7$-cycloalkyl;

$R^4$ is a) $C_2$-$C_6$ alkyl, b) substituted $C_2$-$C_6$ alkyl in which the substituent is: CHO, $CO_2C_1$-$C_4$ alkyl, $CO_2H$, $OC_1$-$C_4$ alkyl, cyclohexyl, phenyl, $NHCO_2tBu$, c) benzyl, d) substituted benzyl in which the substituent on the phenyl group is: F, Cl, Br, I, OH, OPO($OC_1$-$C_4$ alkyl)$_2$, OPO(Obenzyl)$_2$, OPO (OH)$_2$, —PO($OC_1$-$C_4$ alkyl)$_2$, —PO(Obenzyl)$_2$, OPO(OH)$_2$, $NO_2$, $NH_2$, N($C_1$-$C_4$ alkyl)$_2$, Obenzyl, e) $CH_2$ heteroaryl or f) $C_3$-$C_6$ alkenyl;

$R^6$ is a) $C_1$-$C_6$ alkyl, b) substituted $C_1$-$C_6$ alkyl in which the substituent is: -benzyl, —$C_1$-$C_3$ alkyl, or —$OC_1$-$C_4$ alkyl, or c) cyclopropyl;

$R^7$ is a) $C_1$-$C_6$ alkyl, b) benzyl, c) $C_2$-$C_4$ alkyl-O—$C_1$-$C_4$ alkyl or d) phenyl;

$R^{11}$ and $R^{12}$ are hydrogen.

Examples of compounds of the Formula (IIa) include the following:

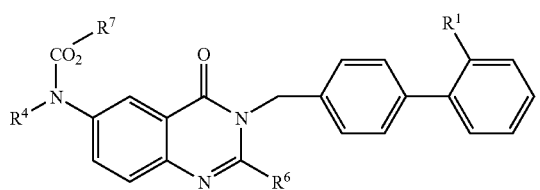

| $R^6$ | $R^1$ | $R^7$ | $R^4$ |
|---|---|---|---|
| Pr | TET | iBu | Et |
| Bu | TET | iBu | Bn |
| Bu | TET | tBu | Me |
| Pr | TET | tBu | Bu |
| Pr | TET | Et | Me |
| Pr | TET | iPr | Me |
| Pr | TET | Me | Me |
| Pr | TET | Bu | Me |
| Pr | TET | iBu | Pr |
| Pr | TET | iBu | allyl |
| Pr | TET | iBu | Pn |
| Pr | TET | iBu | Pn |
| Pr | TET | iBu | (CH$_2$)$_3$Ph |
| Pr | TET | Me | Bn |
| Pr | TET | iBu | Bn |
| Pr | TET | Pr | Bn |
| Pr | TET | Bu | Bn |
| Pr | TET | Bn | Bz |
| Pr | TET | Hx | Bn |
| Pr | TET | tBu | Bn |
| Pr | TET | (CH$_2$)$_2$OMe | Bn |
| Pr | TET | Pr | (CH$_2$)cHex |

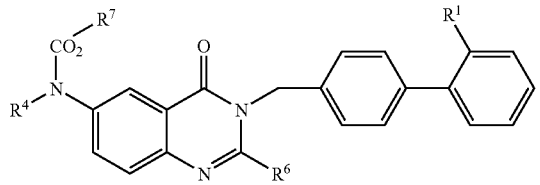

| R⁶ | R¹ | R⁷ | R⁴ |
|---|---|---|---|
| Pr | TET | Bu | Bu |
| Pr | TET | (CH₂)₂OEt | (CH₂)₂OMe |
| Et | TET | IBu | Me |
| Et | TET | IBu | Bn |
| iBu | TET | IBu | Me |
| iBu | TET | IBu | Bn |
| Me | TET | IBu | Bn |
| Me | TET | IBu | Me |
| Pr | SO₂NHCOcPh | IBu | Me |
| Pr | TET | Et | Bn |
| Pr | TET | Ph | CH₂-2-Pyr |
| Et | TET | TBu | Bn |
| Et | TET | Bn | Bn |
| Bu | SO₂NHBz | IBu | Bn |
| Pr | SO₂NHCOcPr | Bu | Bn |
| Pr | SO₂NHBz | IBu | Bn |
| Pr | SO₂NHCOcPr | IBu | Me |
| Pr | TET | Pr | CH₂-2-Pyr |
| Pr | TET | (CH₂)₂OMe | Me |
| Pr | TET | Pr | CH₂-3-Pyr |
| Pr | TET | pR | CH₂-2-Pyr |
| Pr | TET | CH₂-2-OMe | CH₂-4-Pyr |
| CH₂OMe | TET | IBu | Me |
| CH₂OMe | TET | Pr | CH₂-2-Pyr |
| Pr | SO₂NHBz | Bn | Pn |
| Pr | TET | Et | CH₂-2-Pyr |
| Pr | TET | Pr | Bn-4-NO₂ |
| Pr | TET | Pr | Bn-4-NH₂ |
| Pr | TET | Pr | Bn-4-NMe₂ |
| H | TET | IBu | Me |

The AT₂ receptor antagonist may be a compound of the Formula (II) wherein $R^5$ is CONR⁸R⁹Formula (IIb).

In another embodiment, the AT₂ receptor antagonist may be a compound of the Formula (IIb) wherein:

$R^1$ is tetrazol-5-yl or SO₂NHCOR³ or NHSO₂CF₃;

$R^3$ is a) phenyl, b) substituted phenyl in which the substituent is F, Cl, Br, I or $C_1$-$C_4$ alkoxy, c) $C_1$-$C_8$ alkyl substituted with di-($C_1$-$C_4$-alkyl)amino or NH₂, or d) $C_3$-$C_7$-cycloalkyl;

$R^4$ is a) $C_2$-$C_6$ alkyl, b) substituted $C_2$-$C_6$ alkyl in which the substituent is: CHO, CO₂$C_1$-$C_4$ alkyl, CO₂H, O$C_1$-$C_4$ alkyl, cyclohexyl, phenyl, or NHCO₂tBu, c) benzyl, d) substituted benzyl in which the substituent on the phenyl group is: F, Cl, Br, I, OH, OPO(O$C_1$-$C_4$ alkyl)₂, OPO(Obenzyl)₂, OPO(OH)₂, —PO(O$C_1$-$C_4$ alkyl)₂, —PO(Obenzyl)₂, —OPO(OH)₂, NO₂, NH₂, N($C_1$-$C_4$ alkyl)₂, or Obenzyl, e) CH₂ heteroaryl, or f) $C_3$-$C_6$ alkenyl;

$R^6$ is a) $C_1$-$C_6$ alkyl, b) substituted $C_1$-$C_6$ alkyl in which the substituent is: -benzyl, —$C_1$-$C_3$ alkyl, or —O$C_1$-$C_4$ alkyl, or c) cyclopropyl;

$R^8$ is a) $C_1$-$C_6$ alkyl or b) hydrogen;

$R^9$ is a) $C_1$-$C_6$ alkyl, or b) when taken with $R^8$ and the nitrogen atom to which they are attached from a morpholinyl, N—($C_1$-$C_6$ alkyl)piperazinyl, N—(CO$C_1$-$C_6$ alkyl)piperazinyl, or N-aryl-piperazinyl ring system;

$R^{11}$ and $R^{12}$ are hydrogen.

Some examples of compounds of the Formula (IIb) include the following:

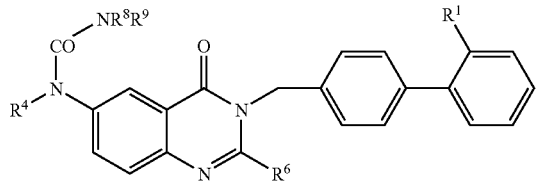

| R⁶ | R¹ | N(R⁸)R⁹ | R⁴ |
|---|---|---|---|
| Bu | TET | N(Me)iPr | Me |
| Pr | TET | N(Pn)₂ | Me |
| Pr | TET | N(Me)Pr | Bn |
| Pr | TET | N(Me)Et | Bn |
| Pr | TET | N(Me)Et | Bn |
| Pr | TET | morpholino | Bn |
| Et | TET | NHPr | Bn |
| Pr | TET | N(Me)iPr | Bn-4-F |
| Pr | TET | N(Me)iPr | CH₂-2-Pyr |

In a further embodiment, the AT₂ receptor antagonist may be a compound of the Formula (II) wherein $R^5$ is COR¹⁰Formula (IIc). One class of this embodiment is represented by the compounds of the Formula (IIc) wherein:

$R^1$ is tetrazol-5-yl, SO₂NHCOR³ or NHSO₂CF₃;

$R^3$ is a) phenyl, b) substituted phenyl in which the substituent is F, Cl, Br, I or $C_1$-$C_4$ alkoxy, c) $C_1$-$C_8$ alkyl substituted with di-($C_1$-$C_4$ alkyl)amino or NH₂, or d) $C_3$-$C_7$-cycloalkyl;

$R^4$ is a) $C_2$-$C_6$ alkyl, b) substituted $C_2$-$C_6$ alkyl in which the substituent is: CHO, CO₂$C_1$-$C_4$ alkyl, CO₂H, O$C_1$-$C_4$ alkyl, cyclohexyl, phenyl, or NHCO₂tBu, c) benzyl, d) substituted benzyl in which the substituent on the phenyl group is: F, Cl, Br, I, OH, OPO(O$C_1$-$C_4$ alkyl)₂, OPO(Obenzyl)₂, OPO(OH)₂, —PO(O$C_1$-$C_4$ alkyl)₂, —PO(Obenzyl)₂, OPO(OH)₂, NO₂, NH₂, N($C_1$-$C_4$ alkyl)₂, Obenzyl, O$C_1$-$C_4$ alkyl, COOH, or CO₂CH₃, e) CH₂ heteroaryl or f $C_3$-$C_6$ alkenyl;

$R^6$ is a) $C_1$-$C_6$ alkyl, b) substituted $C_1$-$C_6$ alkyl in which the substituent is: -benzyl, —$C_1$-$C_3$ alkyl, or —O$C_1$-$C_4$ alkyl or c) cyclopropyl;

$R^{10}$ is (a) phenyl, (b) substituted phenyl in which the substituent is F, Cl, Br, I, methoxy, methyl, CF₃, SMe, SO₂Me, OH, OPO(O—$C_1$-$C_4$ alkyl)₂, OPO(OH)₂, OPO(OBn)₂, CO₂—$C_1$-$C_4$ alkyl, COOH, Obenzyl or OC₆H₅, (c) benzyl, (d) heteroaryl, (e) $C_1$-$C_6$ alkyl or (f) substituted $C_1$-$C_6$ alkyl substituted with: imidazole, piperazine, morpholinyl, N—($C_1$-$C_6$ alkyl)piperazinyl, N—(CO$C_1$-$C_6$ alkyl)piperazinyl, or N-aryl-piperazinyl;

$R^{11}$ and $R^{12}$ are hydrogen.

Some examples of compounds of this embodiment include compounds of the Formula (IIc):

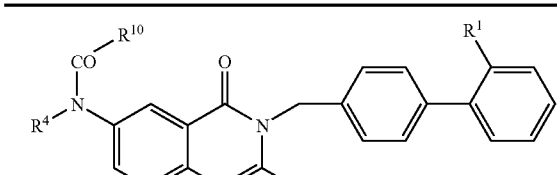

| R⁶ | R¹ | R¹⁰ | R⁴ |
|---|---|---|---|
| Pr | TET | Ph | Pn |
| Pr | TET | Bn | Pn |
| Pr | TET | 4-Pyr | Pn |

-continued

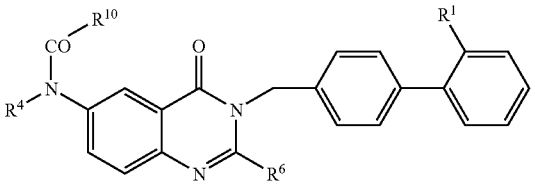

| R⁶ | R¹ | R¹⁰ | R⁴ |
|---|---|---|---|
| Pr | TET | Ph | Bn |
| Pr | TET | Ph-4-Cl | Pn |
| Pr | TET | Ph-4-Cl | Pn |
| Pr | TET | Ph-4-OMe | 4-methyl-pentyl |
| Pr | TET | 2-Furyl | Pn |
| Pr | TET | 3-methylbutyl | |
| Pr | TET | Bu | Bn |
| Pr | TET | Ph-4-F | Pn |
| Pr | TET | Ph-4-F | Bu |
| Pr | TET | Ph-4-Me | Pn |
| Pr | TET | Ph-3-Br | Pn |
| Pr | TET | 3-Methylbutyl | Bn-4-OH |
| Pr | TET | Bu | Bu |
| Et | TET | Ph | Bn |
| Pr | TET | Ph-4-CF₃ | Pn |
| Et | TET | Ph-4-F | Pn |
| 1-Methyl-pentyl | TET | Ph-4-F | Pn |
| Et | TET | PH-4-F | Bu |
| Et | TET | Ph | Bn-4-F |
| c-Pr | TET | Ph | Bn |
| c-Pr | TET | Ph | Pn |
| 1-Methyl-2-phenethyl | TET | Ph | Bn |
| c-Pr | TET | Ph | Bn |
| c-Pr | TET | Ph | Bn |
| Pr | TET | 4-Py | Bu |
| Me | TET | Ph | Bn |
| iPr | TET | Ph | Bn |
| Et | SO₂NHBz | Ph | Bn |
| Pr | TET | 3-Pyr | Pn |
| Pr | SO₂NHCOcPr | Ph | Pn |
| Pr | SO₂NHBz | Ph | Pn |
| Et | TET | 4-Pyr | Bn |
| Pr | TET | Ph-4-SMe | Pn |
| Pr | TET | Ph | Pr |
| Et | TET | Ph-2-Cl | Bn |
| Et | TET | Ph-2-Cl | Bn-2-Cl |
| Pr | TET | Ph-4-SOMe | Pn |
| Pr | TET | Ph | (CH₂)CHO |
| Pr | TET | Ph-4-SO₂Me | Pn |
| Et | TET | Ph | Bn-2-Cl |
| Et | TET | Ph | CH₂CH=CMe₂ |
| Pr | SO₂NHCOcPr | Me | Pr |
| Pr | SO₂NHCOcPr | cPr | Pn |
| Pr | SO₂NHCOcPr | Me | Pn |
| Pr | SO₂NHCOcPh | cPr | Pr |
| Pr | TET | Ph-4-F | Pr |
| Et | TET | Ph | iPn |
| iPr | TET | Ph | Bn-2-Cl |
| iPr | TET | cPr | Bn |
| iPr | TET | cPr | Bn-2-Cl |
| H | TET | Ph | Bn |
| H | TET | Ph | Bn-2-Cl |
| Et | TET | Ph | Bn-4-Cl |
| Et | TET | Ph | Bn-4-F |
| Et | TET | Ph | Bn-3-Et |
| 1-ethyl-ethyl | TET | Ph | Bn |
| 1-ethyl-ethyl | TET | Ph | Bn-2-Cl |
| Pr | TET | Ph | iBu |
| Pr | TET | Ph | (CH₂)₃CO₂Et |
| Pr | NHSO₂CF₃ | Ph | Pn |
| Pr | TET | Ph | (CH₂)₃COOH |
| Me | TET | Ph | Bn-2-Cl |
| Me | TET | 4-Pyr | Bn |
| Pr | SO₂NHCO_cPr | Me | Me |
| Pr | TET | Ph | CH₂CO₂Et |
| Me | TET | 4-Pyr | Bn-2-Cl |

-continued

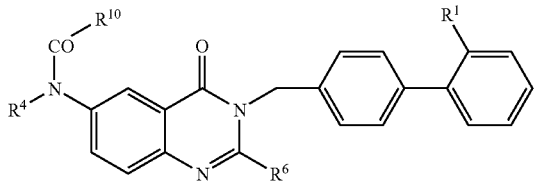

| R⁶ | R¹ | R¹⁰ | R⁴ |
|---|---|---|---|
| Me | TET | 4-Pyr | CH₂CH=CM_{e2} |
| Et | TET | Ph | Bn-4-I |
| Pr | TET | 2-thienyl | Pn |
| Pr | TET | 2-thienyl | Me |
| iPr | TET | Ph | Bn-4-I |
| Et | TET | Ph-4-I | Bn |
| Et | TET | Ph | Bz-2-I |
| Et | TET | 2-thienyl | Bn |
| Pr | TET | 4-Pyr | (CH₂)₂OMe |
| Pr | TET | Ph | CH₂COOH |
| CH₂OMe | TET | Ph-4-Cl | Pn |
| Et | TET | 2-furoyl | Bn |
| Pr | TET | 2-thienyl | Bn |
| Pr | TET | 2-thienyl | Et |
| Pr | TET | 2-furoyl | Et |
| Pr | TET | Ph-2-OMe | Bn |
| Pr | TET | Ph-2-OMe | Pr |
| Pr | TET | Ph-4-OBn | Pn |
| Pr | TET | Ph-4-OBn | Pr |
| Pr | TET | Ph-4-OH | Pn |
| Pr | TET | Ph-4-OH | Pr |
| Pr | TET | CH₂imidazole | Bn |
| Pr | TET | CH₂PIPBoc | Bn |
| Pr | TET | 3-Pyr | Bn |
| Pr | TET | 2-Pyr | Bn |
| Pr | TET | Ph | CH₂-2-Pyr |
| Pr | TET | Ph | CH₂-4-Pyr |
| Pr | TET | 4-Pyr | Bn |
| Me | TET | Ph | CH₂-3-Pyr |
| Me | TET | Ph | CH₂-2-Pyr |
| Pr | TET | Ph-4-OPO(OBn)₂ | Pn |
| Pr | TET | Ph-4-OH | Bu |
| Pr | TET | 4-Pyr | CH₂-2-Pyr |
| Pr | TET | Ph-4-OPO(OH)₂ | Pn |
| Pr | TET | Ph-4-OH | Bn |
| Pr | TET | 2-furoyl | CH₂-2-Pyr |
| Pr | TET | Ph-4-OPO(ONa)₂ | Bu |

Note:
PIP-piperazinyl

In yet another embodiment, the AT₂ receptor antagonist may be a compound of the Formula (II) wherein R⁵ is SO₂R¹⁰ Formula (IId). One class of this embodiment is represented by the compounds of the Formula (IId) wherein:

$R^1$ is tetrazol-5-yl, $SO_2NHSO_2CF_3$ or $NHSO_2CF_3$;

$R^3$ is (a) phenyl, (b) substituted phenyl in which the substituent is F, Cl, Br, I or $C_1$-$C_4$ alkoxy, (c) $C_1$-$C_8$ alkyl substituted with di-($C_1$-$C_4$ alkyl)amino or $NH_2$, or (d) $C_3$-$C_7$-cycloalkyl;

$R^4$ is (a) $C_2$-$C_6$ alkyl, (b) substituted $C_2$-$C_6$ alkyl in which the substituent is: CHO, $CO_2C_1$-$C_4$ alkyl, $CO_2H$, $OC_1$-$C_4$ alkyl, cyclohexyl, phenyl, or $NHCO_2tBu$, (c) benzyl, (d) substituted benzyl in which the substituent on the phenyl group is: F, Cl, Br, I, OH, $OPO(OC_1$-$C_4$ alkyl$)_2$, $OPO(Obenzyl)_2$, $OPO(OH)_2$, —$PO(OC_1$-$C_4$-alkyl$)_2$, —$PO(Obenzyl)_2$, —$OPO(OH)_2$, $NO_2$, $NH_2$, $N(C_1$-$C_4$ alkyl$)_2$, or Obenzyl, (e) $CH_2$ heteroaryl or (f) $C_3$-$C_6$ alkenyl;

$R^6$ is (a) $C_1$-$C_6$ alkyl, (b) substituted $C_1$-$C_6$ alkyl in which the substituent is: -benzyl, —$C_1$-$C_3$ alkyl, or —OC, —$C_4$ alkyl or, (c) cyclopropyl;

$R^{10}$ is (a) phenyl, (b) substituted phenyl in which the substituent is F, Cl, Br, I, methoxy, methyl, $CF_3$, SMe, SOMe, $SO_2Me$, OH, $OPO(O\text{—}C_1\text{-}C_4\text{ alkyl})_2$, $OPO(OH)_2$, OPO $(OBn)_2$, $CO_2C_1\text{-}C_4$ alkyl, or COOH, (c) benzyl, d) heteroaryl, (e) $C_1\text{-}C_6$ alkyl, or (f) substituted $C_1\text{-}C_6$ alkyl substituted with: imidazole, piperazine, morpholinyl, N—($C_1\text{-}C_6$ alkyl)-piperazinyl, N—($COC_1\text{-}C_6$ alkyl)-piperazinyl, or N-aryl-piperazinyl;

$R^{11}$ and $R^{12}$ are hydrogen.

Some examples illustrating compounds of the Formula (IId):

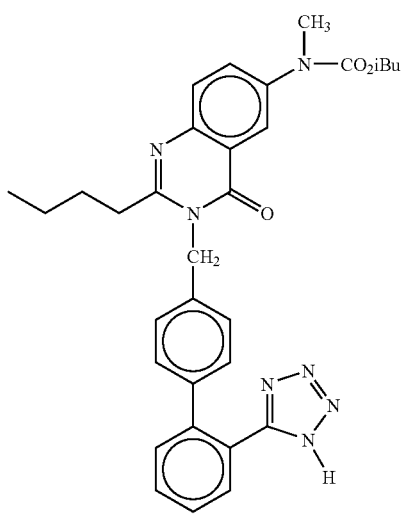

| $R^6$ | $R^1$ | $R^{10}$ | $R^4$ |
|---|---|---|---|
| Pr | TET | Bu | Bn |
| Et | TET | Pr | Pn |
| Et | TET | Bu | Pn |
| Et | TET | Pr | $(CH_2)_3NHBoc$ |
| Et | TET | Pr | Bn |

In naming compounds of Formula (II), it should be noted that the following two names for compound (i) shown below are considered to be equivalent:

(1) 2-Butyl-6-(N-methyl-N-isobutyloxycarbonyl)-amino-3-[(2'-(tetrazol-5-yl)biphen-4-yl)methyl]quinazolin-4-(3H)-one; or, (2) 2-n-Butyl-6-(N-methyl-N-isobutyloxycarbonyl)-amino-3-[(2'-(tetrazol-5-yl)[1,1']-biphenyl-4-yl)methyl]quinazolin-4(3H)-one.

In still another embodiment, the $AT_2$ receptor antagonist may be selected from the substituted quinazolinone compounds listed in U.S. Pat. No. 5,441,959, which is incorporated by reference herein in its entirety. Because U.S. Pat. No. 5,441,959 also describes preparation methods for the compounds included in the reference, these methods are not provided in this application. For example, $AT_2$ receptor antagonist compounds may have the general Formula (III):

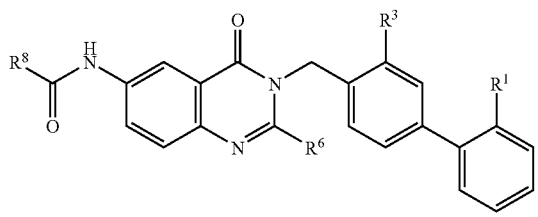

or a pharmaceutically acceptable salt thereof, wherein: $R^1$ is —$SO_2NHCO_2R^{23}$;

$R^3$ is (a) halogen (Cl, Br, I, F), (b) $C_1$-$C_4$ alkyl, or (c) $CF_3$;

$R^6$ is straight chain $C_1$-$C_4$ alkyl;

$R^8$ is (a) $R^{23'}$, (b) $NR^{24}R^{23'}$;

$R^{23}$ and $R^{23'}$ are independently (a) aryl, wherein aryl is defined as phenyl or naphthyl unsubstituted or substituted with one or two substituents selected from the group consisting of: halogen (Cl, Br, I, F), $N(R^{24})_2$, $CO_2R^{24}$, $C_1$-$C_4$ alkyl, $C_1$-$C_4$ alkoxyl, $NO_2$, $CF_3$, $C_1$-$C_4$ alkylthio, OH, —$SO_2N(R^{24})_2$, $C_3$-$C_7$ cycloalkyl, $C_3$-$C_{10}$ alkenyl and $S(O)_n(C_1$-$C_4$ alkyl); where n=1 or 2, (b) heteroaryl, wherein heteroaryl is an unsubstituted or mono, or disubstituted heteroaromatic 5- or 6-membered ring which can contain one or two heteroatoms selected from the group consisting of N, O and S and wherein the substituents are members selected from the group consisting of —OH, —SH, $C_1$-$C_4$ alkyl, $C_1$-$C_4$ alkoxy, $CF_3$, halogen (Cl, Br, I, F) and $NO_2$, (c) $C_3$-$C_7$ cycloalkyl, (d) $C_1$-$C_6$ alkyl optionally substituted with a substituent selected from the group consisting of aryl as defined above, heteroaryl as defined above, —OH, —SH, $C_1$-$C_4$ alkyl, —O($C_1$-$C_4$ alkyl), $C_3$-$C_7$ cycloalkyl, —$S(O)_n(C_1$-$C_4$ alkyl), —$CF_3$, halogen (Cl, Br, F, I), —$NO_2$, —$CO_2H$, $CO_2$—$C_1$-$C_4$-alkyl, —$NH_2$, —$NH(C_1$-$C_4$ alkyl), —$N(C_1$-$C_4$ alkyl)$_2$, or (e) perfluoro-$C_1$-$C_4$ alkyl; and $R^{24}$ is (a) H, (b) $C_1$-$C_6$ alkyl, unsubstituted or substituted with aryl as defined above or heteroaryl as defined above, or (c) aryl; and $R^{23'}$ and $R^{24}$ when taken together may form a morpholine or piperazine ring, wherein the piperazine ring may be substituted on the nitrogen with $C_1$-$C_4$ alkyl or $C_1$-$C_4$ acyl.

In one embodiment of the compounds of Formula (III) above are those wherein:

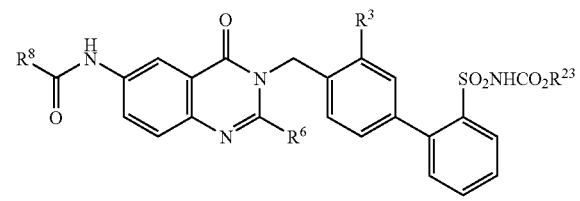

$R^3$ is (a) F, (b) Me, or (c) $CF_3$;

$R^6$ is straight chain $C_1$-$C_4$ alkyl;

$R^8$ is $R^{23'}$;

$R^{23'}$ is (a) aryl, wherein aryl is defined as phenyl or naphthyl unsubstituted or substituted with one or two substituents selected from the group consisting of: halogen (Cl, Br, I, F), N(R$^{24}$)$_2$, CO$_2$R$^{24}$, C$_1$-C$_4$ alkyl, C$_1$-C$_4$ alkoxyl, NO$_2$, CF$_3$, C$_1$-C$_4$ alkylthio, OH, —SO$_2$ N(R$^{24}$)$_2$, C$_3$-C$_7$ cycloalkyl, C$_3$-C$_{10}$ alkenyl and S(O)$_n$(C$_1$-C$_4$ alkyl); where n=1 or 2, (b) heteroaryl, wherein heteroaryl is an unsubstituted or mono- or disubstituted heteroaromatic 5- or 6-membered ring which can contain one or two heteroatoms selected from the group consisting of N, O and S and Wherein the substituents are members selected from the group consisting of —OH, —SH, C$_1$-C$_4$ alkyl, C$_1$-C$_4$ alkoxy, CF$_3$, halogen (Cl, Br, I, F) and NO$_2$, (c) C$_1$-C$_6$ alkyl unsubstituted or substituted with a substituent selected from the group consisting of aryl as defined above, heteroaryl as defined above, —OH, —SH, C$_1$-C$_4$ alkyl, —O(C$_1$-C$_4$ alkyl), C$_3$-C$_7$ cycloalkyl, —CF$_3$, halogen (Cl, Br, F, I), —N(C$_1$-C$_4$ alkyl)$_2$, or C$_3$-C$_7$ cycloalkyl; and R$^{23}$ is (a) C$_1$-C$_6$-alkyl, unsubstituted or substituted with a substituent selected from the group consisting of: aryl as defined above, heteroaryl as defined above, C$_1$-C$_4$ alkyl, CF$_3$, —O(C$_1$-C$_4$ alkyl), C$_3$-C$_7$ cycloalkyl, or (b) perfluoro-C$_1$-C$_4$-alkyl.

This embodiment is exemplified further by:

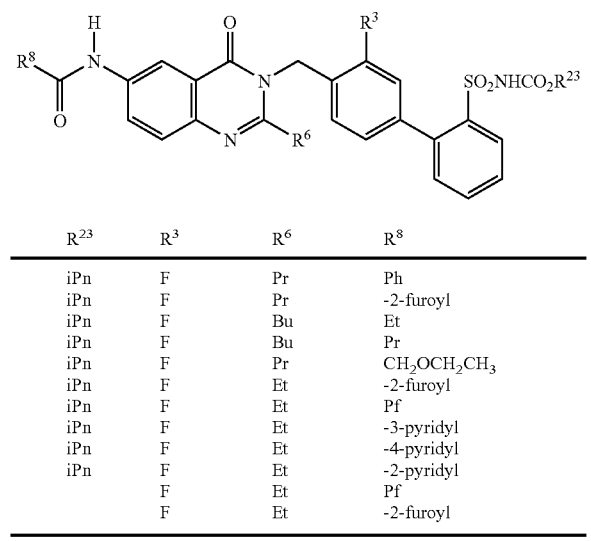

| R$^{23}$ | R$^3$ | R$^6$ | R$^8$ |
|---|---|---|---|
| iPn | F | Pr | Ph |
| iPn | F | Pr | -2-furoyl |
| iPn | F | Bu | Et |
| iPn | F | Bu | Pr |
| iPn | F | Pr | CH$_2$OCH$_2$CH$_3$ |
| iPn | F | Et | -2-furoyl |
| iPn | F | Et | Pf |
| iPn | F | Et | -3-pyridyl |
| iPn | F | Et | -4-pyridyl |
| iPn | F | Et | -2-pyridyl |
|  | F | Et | Pf |
|  | F | Et | -2-furoyl |

Wherein:
Et is ethyl,
Pr is n-propyl,
cPr is cyclopropyl,
Bu is n-butyl,
iPn is 3-methylbutyl,
Ph is phenyl.

In another embodiment of structures of the Formula (III) above, are those wherein R$^{23}$, R$^3$, R$^6$ are as recited in the first embodiment and all other substituents are as recited below:

R$^8$ is —NR$^{24}$R$^{23'}$; R$^{23'}$ is C$_1$-C$_6$ alkyl which is unsubstituted or substituted with a substituent selected from the group aryl, heteroaryl, C$_1$-C$_4$ alkyl, —O(C$_1$-C$_4$ alkyl), CF$_3$, NH(C$_1$-C$_4$ alkyl), N(C$_1$-C$_4$ alkyl)$_2$, C$_3$-C$_7$ cycloalkyl;

R$^{24}$ is (a) C$_1$-C$_6$ alkyl which is unsubstituted or substituted with aryl or heteroaryl, or (b) H; and R$^{23'}$ and R$^{24}$ when taken together may form a morpholine or piperazine ring, wherein the piperazine ring may be substituted on the nitrogen with C$_1$-C$_4$ alkyl or C$_1$-C$_4$ acyl.

This embodiment is exemplified further by compounds including:

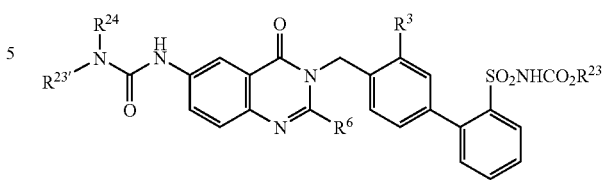

| R$^{23}$ | R$^3$ | R$^6$ | R$^{23'}$ | R$^{24}$ |
|---|---|---|---|---|
| iPn | Me | Pr | iPr | H |
| Bu | Me | Pr | iPr | H |
| Bu | F | Pr | iPr | H |
| iPn | F | Pr | iPr | H |
| iPn | Me | Pr | iPr | H |
| Bu | F | Bu | iPr | Me |
| iPn | F | Pr | iPr | H |
| (CH$_2$)$_2$cPr | F | Bu | iPr | Me |
| (CH$_2$)$_2$cPr | F | Et | Et | H |
| Me | F | Et | Et | H |
| iPn | F | Pr |  | morpholino |
| iPn | F | Bu | iPr | Me |
| iPn | F | Et | iPr | Me |
| iPn | F | Et |  | morpholino |
| Bu | F | Et |  | morpholino |
| iPn | F | Bu |  | piperazinyl-4-methyl |
| Bu | F | Et | iPr | Me |
| (CH$_2$)$_2$cPr | F | Pr | iPr | H |
| tBu | F | Pr | iPr | H |
| iPr | F | Pr | Me | Me |
| iHx | F | Et |  | morpholino |
| iPn | F | Et | Me | Me |
| (CH$_2$)$_2$cPr | F | Et | iPr | H |
| (CH$_2$)$_2$cPr | F | Et | iPr | Me |
| iPn | F | Me | iPr | H |
| iPn | F | Me | iPr | Me |
| (CH$_2$)$_2$cPr | F | Me | Me | Me |
| iBu | F | Et | iPr | Me |
| iPn | F | Et | iPr | Me |

Wherein: Me is methyl, Et is ethyl, Pr is n-propyl, cPr is cyclopropyl, iPr is isopropyl, Bu is n-butyl, iBu is isobutyl, tBu is t-butyl, iPn is 3-methylbutyl, iHx is 4-methylpentyl.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The heteroaryl substituent recited above represents any 5 or 6-membered aromatic ring containing from one to three heteroatoms selected from the group consisting of nitrogen, oxygen, and sulfur, for example, pyridyl, thienyl, furyl, pyrazolyl, pyrrolyl, imidazolyl, pyridazinyl, pyrimidinyl, pyrazinyl, isoxazolyl, isothiazolyl, oxazolyl, triazolyl and thiazolyl.

In still other embodiments, the AT$_2$ receptor antagonist may be selected from the imidazole compounds listed in U.S. Pat. No. 5,545,651, which is incorporated by reference herein in its entirety. Methods of preparation of these imidazole compounds are also described in U.S. Pat. No. 5,545,651 and are incorporated by reference herein. For example, the AT$_2$ receptor antagonist may be compounds of the following Formula (IV):

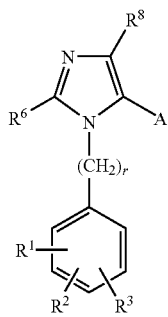

wherein R¹ is in the meta or para position and is
(a) 4-CO₂H,
(b) —CH₂CO₂H,
(c) —C(CF₃)₂OH,
(d) —CONHNHSO₂CF₃,
(e) 4-CONHCH(CO₂H)CH₂C₆H₅ (L-isomer),
(f) 4-CONHOR¹²,
(g) —CONHSO₂R¹⁰,
(h) —CONHSO₂NHR⁹,
(i) —C(OH)R⁹PO₃H₂,
(j) —NHCOCF₃,
(k) —NHCONHSO₂R¹⁰,
(l) —NHPO₃H₂,
(m) 4-NHSO₂R¹⁰,
(n) —NHSO₂NHCOR¹⁰,
(o) —OPO₃H₂,
(p) —OSO₃H,
(q) —PO₃H₂,
(r) —PO(OH)R⁹,
(s) —SO₃H,
(t) —SO₂NHR⁹,
(u) —SO₂NHCOR¹⁰,
(v) —SO₂NHCONHR⁹,

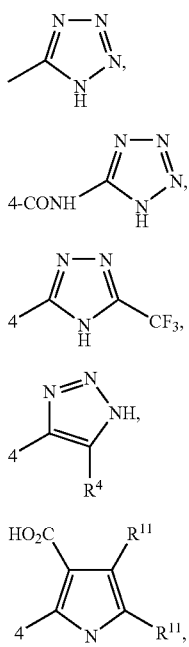

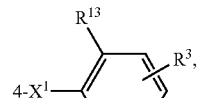

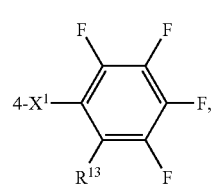

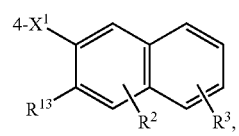

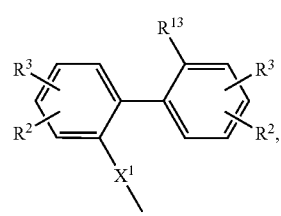

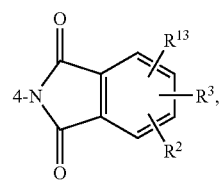

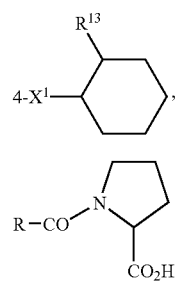

(ii) —SO₂NHCO₂R¹⁰;
R² is independently
(a) H,
(b) halo (F, Cl, Br, I),
(c) C₁-C₄-alkyl,
(d) C₁-C₄-alkoxy,
(e) C₁-C₄-acyloxy,
(f) C₁-C₄-alkylthio,
(g) C₁-C₄-alkylsulfinyl,
(h) C₁-C₄-alkylsulfonyl,
(i) —(C₁-C₄-alkyl)-OH,
(j) —(C₁-C₄)alkyl-aryl,
(k) —CO₂H,
(l) —CN,
(m) tetrazol-5-yl,
(n) —CONHOR₁₂,
(o) —SO₂NHR⁹, (p) —$NH_2$,
(q) $C_1$-$C_4$-alkylamino,
(r) $C_1$-$C_4$-dialkylamino,
(s) —$NHSO_2R^{10}$,
(t) —$NO_2$,
(u) furyl,
(v) phenyl or phenyl optionally substituted with one or two substituents selected from the group consisting of halo, $C_1$-$C_4$-alkyl, $C_1$-$C_4$-alkoxy, —$NO_2$, —$CF_3$, $C_1$-$C_4$-alkylthio, —OH, —$NH_2$, $C_1$-$C_4$-alkylamino, $C_1$-$C_4$-dialkylamino, —CN, —$CO_2R^2$, acetyl;
$R^3$ is independently:
(a) H,
(b) halo,
(c) $C_1$-$C_4$-alkyl,
(d) $C_1$-$C_4$-alkoxy, or
(e) —$C_1$-$C_4$-alkyl-($C_1$-$C_4$-alkoxy);
$R^4$ is:
(a) —CN,
(b) —$NO_2$, or
(c) —$CO_2R^{11}$;
$R^5$ is:
(a) H,
(b) $C_1$-$C_6$-alkyl,
(c) $C_3$-$C_6$-cycloalkyl,
(d) $C_2$-$C_4$-alkenyl, or
(e) $C_2$-$C_4$-alkynyl;
$R^6$ is:
(a) $C_1$-$C_{10}$-alkyl,
(b) $C_3$-$C_{10}$-alkenyl,
(c) $C_3$-$C_{10}$-alkynyl,
(d) $C_3$-$C_8$-cycloalkyl,
(e) $C_3$-$C_8$-cycloalkenyl,
(f) —$C_1$-$C_3$-alkyl-($C_3$-$C_8$-cycloalkyl),
(g) —$C_1$-$C_3$-alkenyl-($C_5$-$C_{10}$-cycloalkyl),
(h) —$C_1$-$C_3$-alkynyl-($C_5$-$C_{10}$-cycloalkyl),
(i) —$(CH_2)_sS(CH_2)_mR^5$, or
(j) benzyl, optionally substituted on the phenyl ring with 1-2 substituents selected from the group consisting of halo, $C_1$-$C_4$-alkyl, $C_1$-$C_4$-alkoxy or —$NO_2$;
$R^7$ is:
(a) $C_1$-$C_6$-alkyl,
(b) $C_3$-$C_6$-cycloalkyl,
(c) aryl, or
(d) benzyl, optionally substituted on the phenyl ring with 1-2 substituents selected from the group consisting of halo, $C_1$-$C_4$-alkyl, $C_1$-$C_4$-alkoxy or —$NO_2$;
$R^8$ is:
(a) H,
(b) halogen (F, Cl, Br, I),
(c) phenyl, or phenyl optionally substituted with halogen (F, Cl, Br, I), $C_1$-$C_4$-alkyl, —OH, $C_1$-$C_4$-alkoxy, —$NO_2$, —$NR^{26}R^{27}$, —$NR^{26}COR^{11}$, —$NR^{26}CO_2R^7$, —$S(O)_rR^{10}$, —$SO_2NR^{26}R^{27}$, —$NR^{26}SO_2R^{10}$, —$CF_3$,
(d) $C_1$-$C_6$-alkyl, optionally substituted with
i) $OR^{25}$,
ii) $S(O)_rR^{10}$,
iii) $NR^{23}R^{24}$,
iv) $NR^{26}COR^{11}$,
v) $NR^{26}CO_2R^7$,
yl) $NR^{26}CONR^{23}R^{24}$,
vii) $OCONR^{23}R^{24}$,
viii) $OCOR^{11}$,
ix) aryl,
(e) $C_2$-$C_6$-alkenyl,
(f) —$C_1$-$C_4$-alkyl-aryl,
(h) $C_1$-$C_4$-alkoxy, (i) $C_vF_{2v+1}$ where v=1 to 3,
(j) —$S(O)_rR^{10}$,
(k) —$S(O)_2NR^{23}R^{24}$,
(l) —$CONR^{23}R^{24}$,
(m) —$COR^7$, or
(n) —$CO_2R^{12}$;
$R^9$ is:
(a) H,
(b) $C_1$-$C_5$-alkyl,
(c) aryl,
(d) —($C_1$-$C_4$-alkyl)-aryl,
(e) heteroaryl, or
(f) $C_3$-$C_5$-cycloalkyl;
$R^{10}$ is:
(a) aryl,
(b) $C_3$-$C_7$-cycloalkyl,
(c) $C_1$-$C_4$-perfluoroalkyl,
(d) $C_1$-$C_4$-alkyl, optionally substituted with a substituent selected from the group consisting of aryl, heteroaryl, —OH, —SH, $C_1$ $C_4$-alkyl, $C_1$-$C_4$-alkoxy, $C_1$-$C_4$-alkylthio, —$CF_3$, halo, —$NO_2$, —$CO_2R^{12}$, —$NH_2$, $C_1$-$C_4$-alkylamino, $C_1$-$C_4$-dialkylamino, —$PO_3H_2$, or
(e) heteroaryl;
$R^{11}$, $R^{11a}$ and $R^{11b}$ are independently:
(a) H,
(b) $C_1$-$C_6$-alkyl,
(c) $C_3$-$C_6$-cycloalkyl,
(d) aryl,
(e) —($C_1$-$C_5$-alkyl)-aryl, or
(f) heteroaryl;
$R^{12}$ is:
(a) H,
(b) methyl, or
(c) benzyl, optionally substituted on the phenyl ring with 1-2 substituents selected from the group consisting of halo, $C_1$-$C_4$-alkyl, $C_1$-$C_4$-alkoxy or —$NO_2$;
$R^{13}$ is:
(a) —$CO_2H$,
(b) —$CH_2CO_2H$,
(c) —$C(CF_3)_2OH$,
(d) —$CONHNHSO_2CF_3$,
(e) —$CONHOR^{12}$,
(f) —$CONHSO_2R^{10}$,
(g) —$CONHSO_2NHR_9$,
(h) —$C(OH)R_9PO_3H_2$,
(i) —$NHCOCF_3$,
(j) —$NHCONHSO_2R^{10}$,
(k) —$NHPO_3H_2$,
(l) —$NHSO_2R^{10}$,
(m) —$NHSO_2NHCOR^{10}$,
(n) —$OPO_3H_2$,
(o) —$OSO_3H$,
(p) —$PO(OH)R^9$,
(q) —$PO_3H_2$,
(r) —$SO_3H$,
(s) —$SO_2NHR^9$,
(t) —$SO_2NHCOR^{10}$,
(u) —$SO_2NHCONHR^9$,
(v) —$SO_2NHCO_2R^{10}$,

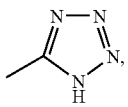 (w)

-continued (y)
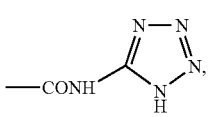

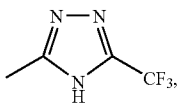

(z)
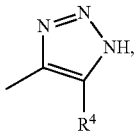

(aa)
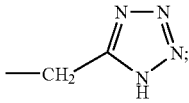

$R^{14}$ is:
(a) H,
(b) $C_1$-$C_6$-alkyl,
(c) —$CH_2CH$=$CH_2$, or
(d) benzyl, optionally substituted on the phenyl ring with 1-2 substituents selected from the group consisting of halo, $C_1$-$C_4$-alkyl, $C_1$-$C_4$-alkoxy or —$NO_2$;
$R^{15}$ is:
(a) H,
(b) $C_1$-$C_8$-alkyl,
(c) $C_1$-$C_8$-perfluoroalkyl,
(d) $C_3$-$C_6$-cycloalkyl,
(e) aryl, or
(f) benzyl, optionally substituted on the phenyl ring with 1-2 substituents selected from the group consisting of halo, $C_1$-$C_4$-alkyl, $C_1$-$C_4$-alkoxy or —$NO_2$;
$R^{16}$ is
(a) H,
(b) $C_1$-$C_6$-alkyl, or
(c) benzyl, optionally substituted on the phenyl ring with 1-2 substituents selected from the group consisting of halo, $C_1$-$C_4$-alkyl, $C_1$-$C_4$-alkoxy or —$NO_2$;
$R^{17}$ is:
(a) H,
(b) $C_1$-$C_6$-alkyl,
(c) $C_3$-$C_6$-cycloalkyl,
(d) aryl, or
(e) benzyl, optionally substituted on the phenyl ring with 1-2 substituents selected from the group consisting of halo, $C_1$-$C_4$-alkyl, $C_1$-$C_4$-alkoxy or —$NO_2$;
$R^{18}$ is:
(a) —$NR^{19}R^{20}$,
(b) —$NHCONH_2$,
(c) —$NHCSNH_2$, or
(d) —$NHSO_2$—$C_6H_5$;
$R^{19}$ and $R^{20}$ are independently:
(a) H,
(b) $C_1$-$C_5$-alkyl, or
(c) aryl,
$R^{21}$ and $R^{22}$ are independently:
(a) $C_1$-$C_4$-alkyl,
or taken together are
(b) —$(CH_2)_q$—;

$R^{23}$ and $R^{24}$ are, independently:
(a) H,
(b) $C_1$-$C_6$-alkyl,
(c) aryl, or
(d) —($C_1$-$C_4$-alkyl)-aryl, or
(e) $R^{23}$ and $R^{24}$ when taken together constitute a pyrrolidine, piperidine or morpholine ring;
$R^{25}$ is:
(a) H,
(b) $C_1$-$C_6$-alkyl,
(c) aryl,
(d) —($C_1$-$C_4$-alkyl)-aryl,
(e) $C_3$-$C_6$-alkenyl, or
(f) —($C_3$-$C_6$-alkenyl)-aryl;
$R^{26}$ and $R^{27}$ are independently:
(a) H,
(b) $C_1$-$C_4$-alkyl,
(c) aryl, or
(d) —$CH_2$-aryl;
$R^{28}$ is:
(a) aryl, or
(b) heteroaryl;
$R^{29}$ is:
(a) —CHO,
(b) —$CONH_2$,
(c) —NHCHO,
(d) —CO—($C_1$-$C_6$ perfluomalkyl),
(e) —S(O)$_r$—($C_1$-$C_6$ perfluoroalkyl),
(f) —O—($C_1$-$C_6$ perfluoroalkyl), or
(g) —$NR^{11a}$—($C_1$-$C_6$ perfluoroalkyl);
$R^{30}$ is:
(a) —CHO,
(b) —$SO_2$—($C_1$-$C_6$ perfluoroalkyl), or
(c) —CO—($C_1$-$C_6$ perfluoroalkyl);
A is:
(a) —$(CH_2)_n$-$L^1$-B-(T)$_y$-(B)$_y$-$X^2$-(B)$_y$-$R^{28}$,
(b) —$(CH_2)_n$-$L^1$-B-T-(B)$_y$-$R^{28}$,
(c) —$(CH_2)_n$-$L^1$-B-(T)$_y$-(B)$_y$-$X^2$-B,
(d) —$(CH_2)_n$-$L^1$-B-T-(B)$_y$-$R^{29}$,
(e) —$(CH_2)_n$-$L^1$-T-(B)$_y$-$X^2$-(B)$_y$-$R^{28}$,
(f) —$(CH_2)_n$-$L^1$-T-(B)$_y$-$R^{28}$,
(g) —$(CH_2)_n$-$L^1$-T-(B)$_y$-$X^2$-B,
(h) —$(CH_2)_n$-$L^1$-($CR^{19}R^{20}$)-D-(T)$_y$-(B)$_y$-$X^3$-(B)$_y$-$R^{28}$,
(i) —$(CH_2)_n$-$L^1$-($OR^{19}R^{20}$)-D-T-(B)$_y$-$R^{28}$,
(j) —$(CH_2)_n$-$L^1$-($CR^{19}R^{20}$)-D-(T)$_y$-(B)$_y$-$X^3$-B,
(k) —$(CH_2)_n$-$L^1$-($CR^{19}R^{20}$)-D-T-(B)$_y$-$R^{29}$,
(l) —$(CH_2)_n$-$L^1$-($CR^{19}R^{20}$)-D-T-(B)$_y$-$X^4$-(B)$_y$-$R^{28}$,
(m) —$(CH_2)_n$-$L^1$-($CR^{19}R^{20}$)-D-B-$X^4$-(B)$_y$-$R^{28}$,
(n) —$(CH_2)_n$-$L^1$-($CR^{19}R^{20}$)-D-T-(B)$_y$-$X^4$-B,
(o) —$(CH_2)_n$-$L^1$-($CR^{19}R^{20}$)-D-B-$X^4$-B,
(p) —$(CH_2)_n$-$L^2$-B-(T)$_y$-(B)$_y$-$X^2$-(B)$_y$-$R^{28}$,
(q) —$(CH_2)_n$-$L^2$-B-T-(B)$_y$-$R^{28}$,
(r) —$(CH_2)_n$-$L^2$-B-(T)$_y$-(B)$_y$-$X_2$-B,
(s) —$(CH_2)_n$-$L^2$-B-T-(B)$_y$-$R^{29}$,
(t) —$(CH_2)_n$-$L^2$-T-(B)$_y$-$X^2$-(B)$_y$-$R^{28}$,
(u) —$(CH_2)_n$-$L^2$-T-(B)$_y$-$R^{28}$,
(v) —$(CH_2)_n$-$L^2$-T-(B)$_y$-$X^2$-B,
(w) —$(CH_2)_n$-$L^2$-D-(T)$_y$-(B)$_y$-$X^3$-(B)$_y$-$R^{28}$,
(x) —$(CH_2)_n$-$L^2$-D-T-(B)$_y$-$R^{28}$,
(y) —$(CH_2)_n$-$L^2$-D-(T)$_y$-(B)$_y$-$X^3$-(B),
(z) —$(CH_2)_n$-$L^2$-D-T-(B)$_y$-$R^{29}$,
(aa) —$(CH_2)_n$-$L^2$-D-T-(B)$_y$-$X^4$-(B)$_y$-$R^{28}$,
(bb) —$(CH^2)_n$-$L^2$-D-B-$X^4$-(B)$_y$-$R^{28}$,
(cc) —$(CH_2)_n$-$L^2$-D-T-(B)$_y$-$X^4$-B,
(dd) —$(CH_2)_n$-$L^2$-D-B-$X^4$-B,
(ee) —$(CH_2)_m$-$L^3$-B-(T)$_y$-(B)$_y$-$X^2$-(B)$_y$-$R^{28}$,
(ff) —$(CH_2)_m$-$L^3$-B-T-(B)$_y$-$R^{28}$, (gg) —(CH$_2$)$_m$-L$^3$-B-(T)$_y$-(B)$_y$-X$^2$-B,
(hh) —(CH$_2$)$_m$-L$^3$-B-T-(B)$_y$-R$^{29}$,
(ii) —(CH$_2$)$_m$-L$^3$-T-(B)$_y$-X$^2$-(B)$_y$-R$^{28}$,
(jj) —(CH$_2$)$_m$-L$^3$-T-(B)$_y$-R$^{28}$,
(kk) —(CH$_2$)$_m$-L$^3$-T-(B)$_y$-X$^2$-B,
(ll) —(CH$_2$)$_m$-L$^3$-(CR$^{19}$R$^{20}$)-D-(T)$_y$-(B)$_y$-X$^3$-(B)$_y$-R$^{28}$,
(mm) —(CH$_2$)$_m$-L$^3$-(CR$^{19}$R$^{20}$)-D-T-(B)$_y$-R$^{28}$,
(nn) —(CH$_2$)$_m$-L$^3$-(CR$^{19}$R$^{20}$)-D-(T)$_y$-(B)$_y$-X$^3$-B,
(oo) —(CH$_2$)$_m$-L$^3$-(CR$^{19}$R$^{20}$)-D-T-(B)$_y$-R$^{29}$,
(pp) —(CH$_2$)$_m$-L$^3$-(CR$^{19}$R$^{20}$)-D-T-(B)$_y$-X$^4$-(B)$_y$-R$^{28}$,
(qq) —(CH$_2$)$_m$-L$^3$-(CR$^{19}$R$^{20}$)-D-(B)-X$^4$-(B)$_y$-R$^{28}$,
(rr) —(CH$_2$)$_m$-L$^3$-(CR$^{19}$R$^{20}$)-D-T-(B)$_y$-X$^4$-B,
(ss) —(CH$_2$)$_m$-L$^3$-(CR$^{19}$R$^{20}$)-D-T-B-X$^4$-B, (tt) 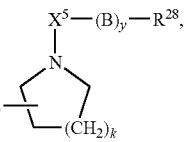

(uu) 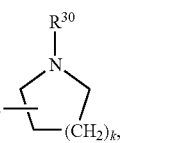

(vv) 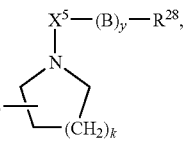

(ww) 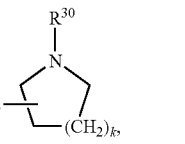

(xx) 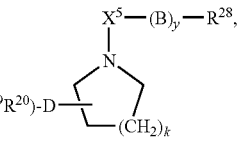

(yy) 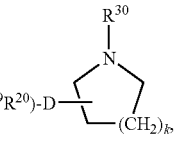

(zz) 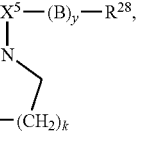

(aaa) 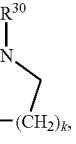

(bbb) 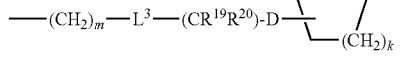

(ccc) 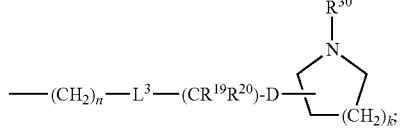

L$^1$ is:
(a) —CO$_2$—,
(b) —CONR$^{11a}$—,
(c) —NR$^{11a}$CO$_2$—, or
(d) —NR$^{11a}$CONR$^{11b}$—;

L$^2$ is:
(a) —CO—,
(b) NR$^{11a}$CO—, or
(c) —O$_2$C—;

L$^3$ is:
(a) —O—,
(b) —SO—, or
(c) —NR$^{11a}$—; B is C$_1$-C$_6$ alkyl; D is C$_2$-C$_8$ alkenyl or C$_2$-C$_8$ alkynyl;

T is:
(a) arylene
(b) heteroarylene;

X$^1$ is:
(a) a carbon-carbon single bond,
(b) —CO—,
(c) —C(R$^{19}$)(R$^{20}$)—,
(d) —O—,
(e) —S—,
(f) —SO—,
(g) —SO$_2$—,
(h) —NR$^{14}$—,
(i) —CONR$_{16}$—,
(j) —NR$^{16}$CO—,
(k) —OC(R$^{19}$)(R$^{20}$)—,
(l) —C(R$^{19}$)(R$^{20}$)O—,
(m) —SC(R$^{19}$)(R$^{20}$)—,
(n) —C(R$^{19}$)(R$^{20}$)—S—,
(o) —NHC(R$^{19}$)(R$^{20}$)—,
(p) —C(R$^{19}$)(R$^{20}$)NH—,
(q) —NR$^{16}$SO$_2$—,
(r) —SO$_2$NR$^{16}$—,
(s) —CH=CH—,
(t) —CF=CF—,
(u) —CF=CH—,
(v) —CH=CF—,
(w) —CF$_2$CF$_2$—,
(x) —CH(OR$^{15}$)—,
(y) —CH(OCOR$^{17}$)—,
(z) —C(=NR$^{18}$)—,
(aa) —C(OR$^{21}$)(OR$^{22}$)—,
(bb) 1,2-cyclopropyl, or
(cc) 1,1-cyclopropyl;

X$^2$ is:
(a) —CO—,
(b) —O—,
(c) —S(O)$_r$—, (d) —($C_1$-$C_4$-alkylene)-,
(e) —$NR^{11a}CONR^{11b}$—,
(f) —$CONR^{11a}$—,
(g) —$NR^{11a}CO$—,
(h) —$SO_2NR^{16}$—,
(i) —$NR^{16}SO_2$—,
(j) —$OCONR^{11a}SO_2$—,
(k) —$SO_2NR^{11a}CO$—,
(l) —$SO_2NR^{11a}CO$—,
(m) —$OCONR^{11a}SO_2$—,
(n) —$SO_2NR^{11a}CONR^{11b}$—,
(o) —$NR^{11a}CONR^{11b}SO_2$—,
(p) —$SO_2NR^{11a}SO_2$—,
(q) —$CONR^{11a}SO_2NR^{11b}$—, or
(r) —$NR^{11a}SO_2NR^{11b}CO$—;
$X^3$ is:
(a) —CO—,
(b) —SO—,
(c) —$SO_2$—,
(d) single bond,
(e) —$CONR^{11a}$—,
(f) —$SO_2NR^{16}$—,
(g) —$CONR^{11a}SO_2$—,
(h) —$SO_2NR^{11a}CO$—,
(i) —$SO_2NR^{11a}CO_2$—,
(j) —$SO_2NR^{11a}CONR^{11b}$—,
(k) —$SO_2NR^{11a}SO_2$—, or
(l) —$CONR^{11a}SO_2NR^{11b}$—;
$X^4$ is
(a) —$NR^{11a}CONR^{11b}$—,
(b) —$OCONR^{11a}SO_2$—,
(c) —$NR^{16}SO_2$—,
(d) —$OCONR^{11a}SO_2$—,
(e) —$NR^{11a}CONR^{11b}SO_2$—, or
(f) —$NR^{11a}SO_2 NR^{11b}CO$—;
$X^5$ is
(a) —CO—,
(b) —$SO_2$—,
(c) —COO—, or
(d) —$CONR^{11a}$—;
Z is:
(a) —O—,
(b) —S—, or
(c) —$NR^{11}$—; k is 1 or 2; m is 1 to 5; n is 0 to 2; q is 2 to 3; r is 0 to 2; s is 0 to 5; t is 0 to 3; u is 2 to 5; y is 0 or 1; and pharmaceutically acceptable salts of these compounds.

Examples of $AT_2$ receptor antagonists include those of Formula (IV), wherein A is:
(a) —$(CH_2)_n$-$L^1$-S-$(T)_y$-$(S)_y$-$X^2$-$(S)_y$-$R^{28}$,
(b) —$(CH_2)_n$-$L^1$-B-$T$-$(B)_y$-$R^{28}$,
(c) —$(CH_2)_n$-$L^1$-B-$(T)_y$-$(B)_y$-$X^2$-B,
(d) —$(CH_2)_n$-$L^1$-B-$T$-$(B)_y$-$R^{29}$,
(e) —$(CH_2)_n$-$L^2$-B-$(T)_y$-$(B)_y$-$X^2$-$(B)_y$-$R^{28}$,
(f) —$(CH_2)_n$-$L^2$-B-$T$-$(B)_y$-$R^{28}$, or
(g) —$(CH_2)_n$-$L^2$-B-$(T)_y$-$(B)_y$-$X^2$-B,
(h) —$(CH_2)_n$-$L^2$-B-$T$-$(B)_y$-$R^{29}$.

In one embodiment the $AT_2$ receptor antagonist may be a compound of Formula (V):

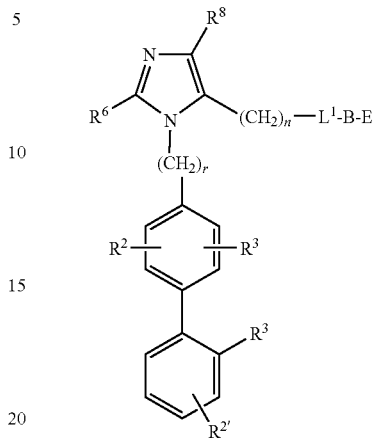

wherein $R^2$ is independently:
(a) H,
(b) halo (F, Cl, Br, I), or
(c) $C_1$-$C_4$-alkyl;
$R^3$ is:
(a) H, or
(b) halo (F, Cl, Br, I);
$R^6$ is
(a) $C_1$-$C_{10}$ alkyl,
(b) $C_3$-$C_{10}$ alkenyl, or
(c) $C_3$-$C_{10}$ alkynyl;
$R^9$ is:
(a) H,
(b) $C_1$-$C_5$-alkyl,
(c) aryl,
(d) —($C_1$-$C_4$-alkyl)-aryl, or
(e) heteroaryl;
$R^{10}$ is
(a) aryl,
(b) $C_3$-$C_7$-cycloalkyl,
(c) $C_1$-$C_4$-perfluoroalkyl,
(d) $C_1$-$C_4$-alkyl, optionally substituted with a substituent selected from the group consisting of aryl, heteroaryl, —OH, —SH, $C_1$-$C_4$-alkyl, $C_1$-$C_4$-alkoxy, $C_1$-$C_4$-alkylthio, —$CF_3$, halo, —$NO_2$, —$CO_2R^{12}$, —$NH_2$, $C_1$-$C_4$-alkylamino, $C_1$-$C_4$-dialkylamino, —$PO_3H_2$, or
(e) heteroaryl;
$R^{11}$, $R^{11a}$ and $R^{11b}$ are independently:
(a) H,
(b) $C_1$-$C_6$-alkyl,
(c) $C_3$-$C_6$-cycloalkyl,
(d) aryl,
(e) —($C_1$-$C_5$-alkyl)-aryl, or
(f) heteroaryl;
$R^{13}$ is:
(a) —$CO_2H$,
(b) —$CONHSO_2R^{10}$,
(c) —$CONHSO_2NHR^9$,
(d) —$NHCONHSO_2R^{10}$,
(e) —$NHSO_2R^{10}$,
(f) —$NHSO_2NHCOR^{10}$,
(g) —$SO_2NHR^9$,
(h) —$SO_2NHCOR^{10}$, (i) —SO$_2$NHCONHR$^9$, (j) —SO$_2$NHCO$_2$R$^{10}$, or

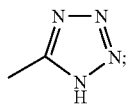
(k)

R$^{16}$ is:

(a) H, (b) C$_1$-C$_6$-alkyl, or (c) benzyl, optionally substituted on the phenyl ring with 1-2 substituents selected from the group consisting of halo, C$_1$-C$_4$-alkyl, C$_1$-C$_4$-alkoxy or —NO$_2$;

R$^{28}$ is (a) aryl, or (b) heteroaryl;

R$^{29}$ is (a) —CHO, (b) —CONH$_2$, (c) —NHCHO, (d) —CO—(C$_1$-C$_6$ perfluomalkyl), (e) —S(O)$_r$—(C$_1$-C$_6$ perfluoroalkyl);

E is:

(a) -(T)$_y$-(B)$_y$-X$_2$-(B)$_y$-R$^{28}$, (b) -T-(B)$_y$-R$^{28}$, (c) -(T)$_y$-(B)$_y$-X$^2$-B or, (d) -T-(B)$_y$-R$^{29}$;

L$^1$ is (a) —CO$_2$—, (b) —CONR$^{11a}$—, (c) —NR$^{11a}$CO$_2$—, (d) —NR$^{11a}$CONR$^{11b}$;

B is C$_1$-C$_6$ alkyl;

X$^2$ is:

(a) —CO—, (b) —O—, (c) —S(O)$_r$—, (d) —(C$_1$-C$_4$-alkylene)-, (e) —NR$^{11al}$CONR$^{11b}$—, (f) —CONR$^{11a}$—, (g) —NR$^{11a}$CO—, (h) —SO$_2$NR$^{16}$, (i) —NR$^{16}$SO$_2$—, (j) —CONR$^{11a}$SO$_2$—, (k) —SO$_2$NR$^{11a}$CO—, (l) —SO$_2$NR$^{11a}$CO$_2$—, (m) —OCONR$^{11a}$SO$_2$—, (n) —SO$_2$NR$^{11a}$CONR$^{11b}$—, (o) —NR$^{11a}$CONR$^{11b}$SO$_2$—, (p) —SO$_2$NR$^{11a}$SO$_2$—, (q) —CONR$_{11a}$SO$_2$NR$^{11b}$—, or (r) —NR$^{11a}$SO$_2$NR$^{11b}$CO—, and pharmaceutically acceptable salts of these compounds.

Other examples of AT$_2$ receptor antagonists include compounds of Formula (VI):

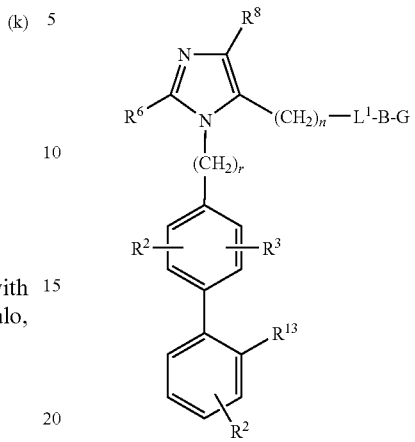

wherein R$^2$ is independently:

(a) H, (b) halo (F, Cl, Br, I), or (c) C$_1$-C$_4$-alkyl;

R$^3$ is (a) H, or (b) halo (F, Cl, Br, I);

R$^6$ is (a) C$_1$-C$_{10}$ alkyl, (b) C$_3$-C$_{10}$ alkenyl, or (c) C$_3$-C$_{10}$ alkynyl;

R$^9$ is (a) H, (b) C$_1$-C$_5$-alkyl, (c) aryl, (d) —(C$_1$-C$_4$-alkyl)-aryl, or (e) heteroaryl;

R$^{10}$ is (a) aryl, (b) C$_3$-C$_7$-cycloalkyl, (c) C$_1$-C$_4$-perfluoroalkyl, (d) C$_1$-C$_4$-alkyl, optionally substituted with a substituent selected from the group consisting of aryl, heteroaryl, —OH, —SH, C$_1$-C$_4$-alkyl, C$_1$-C$_4$-alkoxy, C$_1$-C$_4$-alkylthio, —CF$_3$, halo, —NO$_2$, —CO$_2$R$^{12}$, —NH$_2$, C$_1$-C$_4$-alkylamino, C$_1$-C$_4$-dialkylamino, —PO$_3$H$_2$, or (e) heteroaryl;

R$^{11}$, R$^{11a}$ and R$^{11b}$ are independently:

(a) H, (b) C$_1$-C$_6$-alkyl, (c) C$_3$-C$_6$-cycloalkyl, (d) aryl, (e) —(C$_1$-C$_5$-alkyl)-aryl, or (f) heteroaryl;

R$^{13}$ is (a) —CO$_2$H, (b) —CONHSO$_2$R$^{10}$, (c) —CONHSO$_2$NHR$^9$, (d) —NHCONHSO$^2$R$^{10}$, (e) —NHSO$^2$R$^{10}$, (f) —NHSO$_2$NHCOR$^{10}$, (g) —SO$_2$NHR$^9$, (h) —SO$_2$NHCOR$^{10}$, (i) —SO₂NHCONHR⁹,
(j) —SO₂NHCO₂R¹⁰, or (k)

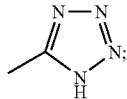

R¹⁶ is:
(a) H,
(b) $C_1$-$C_6$-alkyl, or
(c) benzyl, optionally substituted on the phenyl ring with 1-2 substituents selected from the group consisting of halo, $C_1$-$C_4$-alkyl, $C_1$-$C_4$-alkoxy or —NO₂;
R²⁸ is:
(a) aryl, or
(b) heteroaryl;
R²⁹ is
(a) —CHO,
(b) —CONH₂,
(c) —NHCHO,
(d) —CO—($C_1$-$C_6$ perfluomalkyl),
(e) —S(O)$_r$—($C_1$-$C_6$ perfluoroalkyl),
G is:
(a) -(T)$_y$-(B)$_y$-X²-(B)$_y$-R²⁸,
(b) -T-(B)$_y$-R²⁸,
(c) -(T)$_y$-(B)$_y$-X²-(B), or
(d) -T-(B)$_y$-R²⁹;
L² is —CO—, —NR¹¹ᵃCO— or —O₂C—;
B is $C_1$-$C_6$ alkyl;
X² is
(a) —CO—,
(b) —O—,
(c) —S(O)$_r$—,
(d) —($C_1$-$C_4$-alkylene)-,
(e) —NR¹¹ᵃCO, —NR¹¹ᵃCONR¹¹ᵇ—,
(f) —CONR¹¹ᵃ—,
(g) —NR¹¹ᵃCO—,
(h) —SO₂NR¹⁶—,
(i) —NR¹⁶SO₂—,
(j) —SO₂NR¹¹ᵃSO₂—,
(k) —SO₂NR¹¹ᵃCO₂—,
(l) —SO₂NR¹¹ᵃCO₂—,
(m) —OCONR¹¹ᵃSO₂—,
(n) —SO₂NR¹¹ᵃCONR¹¹ᵇ—,
(o) —NR¹¹ᵃCONR¹¹ᵇSO₂—,
(p) —SO₂NR¹¹ᵃSO₂—,
(q) —CONR¹¹ᵃSO₂NR¹¹ᵇ—, or
(r) —NR¹¹ᵃSO₂NR¹¹ᵇCO—,
and pharmaceutically acceptable salts of these compounds.

Exemplary compounds of Formulas IV, V, and VI are the following:

1-((2'-((i-Amyloxycarbonylamino)sulfonyl)-3-fluoro-(1,1'-biphenyl)-4-yl)methyl)-5-[2-(N-benzoyl-N-phenylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-benzoyl-N-phenylamino)ethylcarbonyl]-4-ethyl-2-propyl-1H-imidazole;

1-((2'-((n-Propyloxycarbonylamino)sulfonyl)-3-fluoro-(1,1'-biphenyl)-4-yl)methyl)-5-[2-(N-benzoyl-N-phenylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-benzoyl-N-butylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-benzoyl-N-propylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-butyryl-N-propylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-butyryl-N-phenylamino)ethylcarbonyl]-4-ethyl-2-propyl-1H-imidazole;

1-((2'-((i-Amyloxycarbonylamino)sulfonyl)-3-fluoro-(1,1'-biphenyl)-4-yl)methyl)-5-[2-(N-butyryl-N-phenylamino)ethylcarbonyl]-4-ethyl-2-propyl-1H-imidazole;

1-((2'-((i-Amyloxycarbonylamino)sulfonyl)-3-fluoro-(1,1'-biphenyl)-4-yl)methyl)-5-[2-(N-isonicotinoyl-N-pyridin-3-ylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-isonicotinoyl-N-pyridin-3-ylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-nicotinoyl-N-pyridin-3-ylamino)ethylcarbonyl]-4-ethyl-2-propyl-1H-imidazole;

1-((2'-((i-Amyloxycarbonylamino)sulfonyl)-3-fluoro-(1,1'-biphenyl)-4-yl)methyl)-5-[2-(N-nicotinoyl-N-pyridin-3-ylamino)ethylcarbonyl]-4-ethyl-2-propyl-1 H-imidazole;

1-((2'-((i-Amyloxycarbonylamino)sulfonyl)-3-fluoro-(1,1'-biphenyl)-4-yl)methyl)-5-[2-(N-nicotinoyl-N-pyridin-2-ylamino)ethylcarbonyl]-4-ethyl-2-propyl-1H-imidazole;

1-((2'-((i-Amyloxycarbonylamino)sulfonyl)-3-fluoro-(1,1'-biphenyl)-4-yl)methyl)-5-[2-(N-isonicotinoyl-N-phenylamino)ethylcarbonyl]-4-ethyl-2-propyl-1H-imidazole;

1-((2'-((i-Amyloxycarbonylamino)sulfonyl)-3-fluoro-(1,1'-biphenyl)-4-yl)methyl)-5-[2-(N-butyryl-N-pyridin-3-ylamino)ethylcarbonyl]-4-ethyl-2-propyl-1H-imidazole;

1-((2'-((i-Amyloxycarbonylamino)sulfonyl)-3-fluoro-(1,1'-biphenyl)-4-yl)methyl)-5-[2-(N-isobutyryl-N-pyridin-3-ylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-acetyl-N-pyridin-3-ylamino)ethylcarbonyl]-4-ethyl-2-propyl-1H-imidazole;

1-((2'-((i-Amyloxycarbonylamino)sulfonyl)-3-fluoro-(1,1'-biphenyl)-4-yl)methyl)-5-[2-(N-butyryl-N-pyridin-2-ylamino)ethylcarbonyl]-4-ethyl-2-propyl-1H-imidazole;

1-((2'-((i-Amyloxycarbonylamino)sulfonyl)-(1,1'-biphenyl)-4-yl)methyl)-5-[2-(N-butyryl-N-pyridin-3-ylamino)ethylcarbonyl]-2-butyl-4-chloro-1H-imidazole;

1-((2'-((i-amyloxycarbonylamino)sulfonyl)-3-fluoro-(1,1'-biphenyl)-4-yl)methyl)-5-[2-(N-propionyl-N-pyridin-3-ylamino)ethylcarbonyl]-4-ethyl-2-propyl-1H-imidazole;

1-((2'-((i-Amyloxycarbonylamino)sulfonyl)(1,1'-biphenyl)-4-yl)methyl)-5-[2-(N-nicotinoyl-N-pyridin-3-ylamino)ethylcarbonyl]-4-ethyl-2-propyl-1H-imidazole;

1-((2'-((i-Amyloxycarbonylamino)sulfonyl)(1,1'-biphenyl)-4-yl)methyl)-5-[2-(N-butyryl-N-pyridin-3-ylamino)ethylcarbonyl]-4-ethyl-2-propyl-1H-imidazole;

1-((2'-((n-Butyloxycarbonyl-amino)sulfonyl)-3-fluoro-(1,1'-biphenyl)-4-yl)methyl)-4-ethyl-5-(2-(2-phenoxyphenyl)ethylcarbonyl)-2-propyl-1H-imidazole;

4-[((5-(2-Benzoylbenzyloxycarbonyl)-4-ethyl-2-n-propyl)imidazol-1-yl)methyl]-3-fluoro-2'-n-butyloxycarbonylaminosulfonyl-1,1'-biphenyl;

4-[((5-(2-Benzoylbenzyloxycarbonyl)-4-ethyl-2-n-propyl)imidazol-1-yl)methyl]-3-fluoro-2'-((2-phenyl)ethyloxycarbonylaminosulfonyl)-1,1'-biphenyl;

4-[((5-(2-Benzoylbenzyloxycarbonyl)-4-ethyl-2-n-propyl)imidazol-1-yl)methyl]-2'-((2-phenyl)ethyloxycarbonylaminosulfonyl)-1,1'-biphenyl;

4-[((5-(2-Benzoylbenzyloxycarbonyl)-4-ethyl-2-n-propyl)imidazol-1-yl)methyl]-3-fluoro-2'-n-butyloxycarbonylaminosulfonyl-1,1'-biphenyl;

4-[((5-(2-Benzoylbenzyloxycarbonyl)-4-ethyl-2-n-propyl)imidazol-1-yl)methyl]-3-fluoro-2'-n-isoamyloxycarbonylaminosulfonyl-1,1'-biphenyl;

4-[((5-(2-Benzoylbenzyloxycarbonyl)-4-ethyl-2-n-propyl)imidazol-1-yl)methyl]-2'-n-isoamyloxycarbonylaminosulfonyl-1,1'-biphenyl;

4-[((5-(2-Benzoylbenzyloxycarbonyl)-4-ethyl-2-n-propyl)imidazol-1-yl)methyl]-3-fluoro-2'-n-propyloxycarbonylaminosulfonyl-1,1'-biphenyl;

4-[((5-(2-Isoamyloxybenzyloxycarbonyl)-4-ethyl-2-n-propyl)imidazol-1-yl)methyl]-3-fluoro-2'-n-butyloxycarbonylaminosulfonyl-1,1'-biphenyl;

4-[((5-(2-Phenylaminocarbonyl)benzyloxycarbonyl-4-ethyl-2-n-propyl)imidazol-1-yl)methyl]-3-fluoro-2'-n-butyloxycarbonylaminosulfonyl-1,1'-biphenyl;

4-[((5-(2-Benzoylbenzyloxycarbonyl)-4-ethyl-2-n-propyl)imidazol-1-yl)methyl]-3-fluoro-2'-(1H-tetrazol-5-yl)-1,1'-biphenyl;

4-[((5-)2-trifluorophenyl)methylaminocarbonyl)-4-ethyl-2-n-propyl)imidazol-1-yl)methyl]-3-fluoro-2'-isoamyloxycarbonylaminosulfonyl-1,1'-biphenyl;

N-butyl, N-benzyl-2-(aminocarbonyl)ethynylmethyl 4-ethyl-2-propyl-1-[[2'-(1H-tetrazol-5-yl)biphenyl-4-yl]methyl]imidazole-5-carboxylate;

N,N-diphenyl-2-(aminocarbonyl)ethynylmethyl 4-ethyl-2-propyl-1-[[2'-(1H-tetrazol-5-yl)biphenyl-4-yl]methyl]imidazole-5-carboxylate;

N-phenyl-2-(aminocarbonyl)ethyl 4-ethyl-2-propyl-1-[[2'-(1H-tetrazol-5-yl)biphenyl-4-yl]methyl]imidazole-5-carboxylate;

N-butyl, N-benzyl-4-(aminocarbonyl)propyl 4-ethyl-2-propyl-1-[[2'-(1H-tetrazol-5-yl)biphenyl-4-yl]methyl]imidazole-5-carboxylate;

N,N-dipentyl-4-(aminocarbonyl)propyl 4-ethyl-2-propyl-1-[[2'-(tetrazol-5-yl)biphenyl-4-yl]methyl]imidazole-5-carboxylate;

4-[(5-((2-benzoyl)phenylcarbonyloxymethyl)-4-chloro-2-n-propylimidazol-1-yl)methyl]-3-fluoro-2'-isoamyloxycarbonylaminosulfonylbiphenyl; and 1-((2'-((n-butyloxycarbonylamino)sulfonyl)-3-fluoro-(1,1'-biphenyl)-4-yl)methyl)-2-(n-propyl)-4-ethyl-5-(2-(phenoxy)phenoxy)acetyl-1H-imidazole.

With reference to compounds of Formulas IV, V, and VI, when an alkyl substituent is mentioned, the normal alkyl structure is meant (e.g. butyl is n-butyl) unless otherwise specified. However, in the definition of radicals above (e.g. $R^3$), both branched and straight chains are included in the scope of alkyl, alkenyl and alkynyl.

The term aryl is meant to include phenyl, biphenyl, napthyl, or fluorenyl group optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$.

The term heteroaryl is meant to include unsubstituted, monosubstituted or disubstituted 5- to 10-membered mono- or bicyclic aromatic rings which can optionally contain from 1 to 3 heteroatoms selected from the group consisting of O, N, and S. Included in the definition of the group heteroaryl, but not limited to, are the following: pyridyl, pyridazinyl, pyrimidinyl, pyrazinyl, 1,3,5-triazinyl, furyl, thiophenyl, imidazolyl, oxazolyl, thiazolyl, benzofuranyl, benzothiophenyl, benzimidazolyl, benzoxazolyl, benzothiazolyl, indolin-2-onyl, indolinyl, indolyl, pyrrolyl, quinonlinyl and isoquinolinyl. Particularly preferred are 2-, 3-, or 4-pyridyl; 2-, or 3-furyl; 2-, or 3-thiophenyl; 2-, 3-, or 4-quinolinyl; or 1-, 3-, or 4-isoquinolinyl optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$.

The term arylene is meant to include a phenyl, biphenyl, napthyl, or fluorenyl group which is used as a link for two groups to form a chain. Included in the definition of arylene, but not limited to, are the following isomeric linkers: 1,2-phenyl, 1,3-phenyl, 1,4-phenyl; 4,4'-biphenyl, 4,3'-biphenyl, 4,2'-biphenyl, 2,4'-biphenyl, 2,3'-biphenyl, 2,2'-biphenyl, 3,4'-biphenyl, 3,3'-biphenyl, 3,2'-biphenyl; 1,2-napthyl, 1,3-napthyl, 1,4-napthyl, 1,5-napthyl, 1,6-napthyl, 1,7-napthyl, 1,8-napthyl, 2,6-napthyl, 2,3-napthyl; 1,4-fluorenyl. Particularly preferred are 1,2-phenyl, 1,3-phenyl, 1,4-phenyl, 4,4'-biphenyl, 3,3'-biphenyl, and 2,2'-biphenyl optionally substituted with one to three substituents selected from the group consisting of —OH, —SH, $C_1$-$C_4$ alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$.

The term heteroarylene is meant to include unsubstituted 5- to 10-membered aromatic ring which can optionally contain from 1 to 3 heteroatoms selected from the group consisting of O, N, and S which is used as a link for two groups to form a chain. Included in the definition of the group heteroaryl, but not limited to, are the following: 2,3-pyridyl, 2,4-pyridyl, 2,5-pyridyl, 2,6-pyridyl, 3,4-pyridyl, 3,5-pyridyl, 3,6-pyridyl; 2,3-furyl, 2,4-furyl, 2,5-furyl; 2,3-thiophenyl, 2,4-thiophenyl, 2,5-thiophenyl; 4,5-imidazolyl, 4,5-oxazolyl; 4,5-thiazolyl; 2,3-benzofuranyl; 2,3-benzothiophenyl; 2,3-benzimidazolyl; 2,3-benzoxazolyl; 2,3-benzothiazolyl; 3,4-indolin-2-onyl; 2,4-indolinyl; 2,4-indolyl; 2,4-pyrrolyl; 2,4-quinolinyl, 2,5-quinolinyl, 4,6-quinolinyl; 3,4-isoquinolinyl, 1,5-isoquinolinyl. Particularly preferred are 2,3-pyridyl, 3,4-pyridyl, 2,3-furyl, 3,4-furyl 2,3-thiophenyl, 3,4-thiophenyl, 2,3-quinolinyl, 3,4-quinolinyl and 1,4-isoquinolinyl optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$.

Pharmaceutically acceptable salts include both the metallic (inorganic) salts and organic salts; a non-exhaustive list of which is given in Remington's Pharmaceutical Sciences 17th Edition, pg. 1418 (1985). It is well known to one skilled in the art that an appropriate salt form is chosen based on physical and chemical stability, flowability, hydroscopicity and solubility. Preferred salts include potassium, sodium, calcium and ammonium salts.

It should be noted in the foregoing structural formula, when a radical can be a substituent in more than one previously defined radical, that first radical ($R^\#$, B or y) can be selected independently in each previously defined radical. For example, $R^1$ and $R^2$ can each be —$CONHOR^{12}$. $R^{12}$ need not be the same substituent in each of $R^1$ and $R^2$, but can be selected independently for each of them. Or if, for example, the same R group (let us take $R^2$, for instance) appears twice in a molecule, each of those R groups is independent of each other (one $R^2$ group may be —$CONHOR^{12}$, while the other $R^2$ group may be —CN).

It is understood that many of the compounds of Formulas IV, V, and VI above contain one or more chiral centers and that these stereoisomers may possess distinct physical and biological properties. All of the stereoisomers or mixtures thereof are included. If the pure enantiomers or diastereomers are desired, they may be prepared using starting materials with the appropriate stereochemistry, or may be separated from mixtures of undesired stereoisomers by standard techniques, including chiral chromatography and recrystallization of diastereomeric salts.

Additional examples of non-peptide antagonists of Ang II, including some biphenylmethyl imidazoles for example in U.S. Pat. No. 5,138,069; Australian Application AU-A-80163/91 (EP 465,368); and EPA 503,162.

In still other embodiments, the $AT_2$ receptor antagonist may be selected from the compounds listed in U.S. Pat. No. 5,338,740, which is incorporated by reference herein in its entirety. U.S. Pat. No. 5,338,740 also provides methods for producing these compounds.

For example, $AT_2$ receptor antagonist may be a compound of general Formula (VII):

Ar—W-Het wherein Ar is selected from the group consisting of

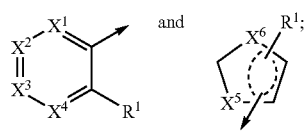

and $X^1$, $X^2$, $X^3$ and $X^4$ are independently selected from $CR^2$ and nitrogen;

one of $X^5$ and $X^6$ is CH and the other is S;

$R^1$ is selected from the group consisting of $CO_2H$, $NHSO_2CF_3$, $CONHSO_2(C_1-C_8)$alkyl, $PO_3H$, $SO_3H$, —$CONHSO_2(C_6H_5)$, $CONHSO_2CF_3$, tetrazole,

and —$SO_2NHCO_2(C_1-C_8)$alkyl; $R^2$ is selected from hydrogen, $(C_1-C_8)$alkyl, $(C_2-C_{10})$alkenyl, $(C_3-C_8)$cycloalkyl, halo, hydroxy, —O—$(C_1-C_6)$alkyl, —S—$(C_1-C_6)$alkyl, —SO—$(C_1-C_6)$alkyl, —$SO_2$—$(C_1-C_6)$alkyl, —$NR^3R^4$, and phenyl, wherein said phenyl is optionally mono-, di- or tri-substituted with substituents independently selected from hydrogen, $(C_1-C_8)$alkyl, $(C_2-C_{10})$alkenyl, $(C_3-C_8)$cycloalkyl, halo, $(C_1-C_6)$alkoxy, —S—$(C_1-C_6)$alkyl, —SO—$(C_1-C_6)$alkyl, —$SO_2$—$(C_1-C_6)$alkyl, —O—$(C_1-C_6)$alkyl, and —$NR^3R^4$;

$R^3$ and $R^4$ are independently selected from hydrogen, $(C_1-C_8)$alkyl, $(C_2-C_{10})$alkenyl and $(C_3-C_8)$cycloalkyl, or $R^3$ and $R^4$, together with the nitrogen to which they are attached, form a cyclic 5-7-membered saturated or partially saturated carbocyclic or heterocyclic ring with one or two heteroatoms independently selected from nitrogen, oxygen and sulfur; and the dotted line represents that the ring containing $X^5$ and $X^6$ is aromatic:

W is a carbobicyclic or heterobicyclic ring system having the formula

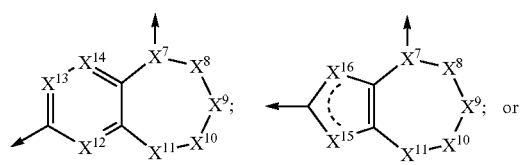

-continued

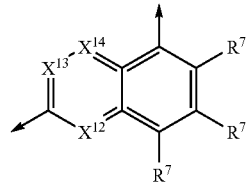

and $X^8$, $X^9$, $X^{10}$ and $X^{11}$ are present or absent, and each of $X^7$, $X^8$, $X^9$, $X^{10}$ and $X^{11}$ is independently selected from $CHR^5$, O, S, SO, $SO_2$, and $NR^6$;

$X^{12}$, $X^{13}$, and $X^{14}$ are independently selected from $CR^7$ or N;

$X^{15}$ and $X^{16}$ are independently selected from $CR^7$ and S;

$R^5$ is absent when the CH moiety of $CHR^5$ is connected to Het and when $R^5$ is present it is selected from hydrogen, $(C_1-C_8)$alkyl, $(C_2-C_{10})$alkenyl, $(C_3-C_8)$cycloalkyl, —O—$(C_1-C_6)$alkyl, and phenyl, wherein said phenyl is optionally mono-, di- or tri-substituted with substituents independently selected from hydrogen, $(C_1-C_8)$alkyl, $(C_2-C_{10})$alkenyl, $(C_3-C_8)$cycloalkyl, halo, $(C_1-C_6)$alkoxy, —S—$(C_1-C_6)$alkyl, —SO—$(C_1-C_6)$alkyl, —$SO_2$—$(C_1-C_6)$alkyl, —O—$(C_1-C_6)$ alkyl, and —$NR^3R^4$;

$R^6$ is selected from $(C_1-C_8)$alkyl, $(C_3-C_8)$cycloalkyl and phenyl, wherein said cycloalkyl is saturated or partially saturated and wherein said cycloalkyl may optionally contain a heteroatom selected from nitrogen, oxygen, and sulfur, and said phenyl is optionally mono-, di- or tri-substituted with substituents independently selected from hydrogen, $(C_1-C_8)$alkyl, $(C_1-C_{10})$alkenyl, $(C_3-C_8)$cycloalkyl, halo, $(C_1-C_6)$alkoxy, —S—$(C_1-C_6)$alkyl, —SO—$(C_1-C_6)$alkyl, —$SO_2$-$_2$-$(C_1-C_6)$alkyl, —O—$(C_1-C_6)$alkyl, and —$NR^3R^4$;

$R^7$ is selected from hydrogen, $(C_1-C_8)$alkyl, $(C_2-C_{10})$alkenyl, $(C_3-C_8)$cycloalkyl, halo, hydroxy, —O—$(C_1-C_6)$alkyl, —S—$(C_1-C_6)$alkyl, —SO—$(C_1-C_6)$alkyl, —$SO_2$-$_2$—$(C_1-C_6)$alkyl, —$NR^3R^4$, and phenyl, wherein said phenyl is optionally mono-, di- or tri-substituted with substituents selected from hydrogen, $(C_1-C_8)$alkyl, $(C_1-C_{10})$alkenyl, $(C_3-C_8)$cycloalkyl, halo, $(C_1-C_6)$alkoxy, —S—$(C_1-C_6)$alkyl, —SO—$(C_1-C_6)$alkyl, —$SO_2$—$(C_1-C_6)$alkyl, —O—$(C_1-C_6)$ alkyl, and —$NR^3R^4$; and the dotted line represents that the ring containing $X^{15}$ and $X^{16}$ contain one or two double bonds; and Het is selected from the group consisting of:

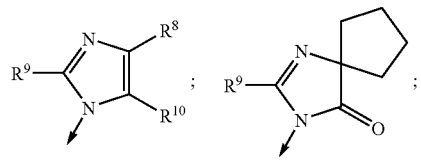

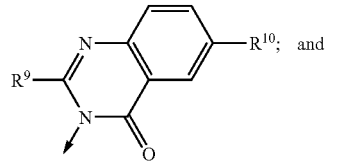

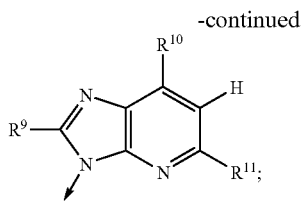

and $R^8R^9$, $R^{10}$ and $R^{11}$ are independently selected from hydrogen, $(C_1-C_8)$alkyl, $(C_1-C_{10})$alkenyl, $(C_3-C_8)$cycloalkyl, halo, $(C_1-C_8)$alkoxy, —S—$(C_1-C_6)$alkyl, —SO—$(C_1-C_6)$alkyl, —$CO_2H$, —$SO_2NR^3R^4$, —$NR^3R^4$, and phenyl, wherein said phenyl is optionally mono-, di-, or tri-substituted with halo, hydroxy, nitro, $(C_1-C_8)$alkyl, $(C_3-C_6)$cycloalkyl, $(C_1-C_7)$alkoxy, $(C_1-C_7)$alkylthio, and amino, wherein said amino is optionally mono- or di-substituted with $(C_1-C_7)$alkyl;

and wherein each occurrence of $R^3$ can be the same or different from any other occurrence of $R^3$, and each occurrence of $R^4$ can be the same or different from any other occurrence of $R^4$;

with the proviso that: (a) no more than two of $X^1$, $X^2$, $X^3$ and $X^4$ can be nitrogen; and (b) at least two of $X^7$, $X^8$, $X^9$, $X^{10}$ and $X^{11}$ are present;

and to pharmaceutically acceptable salts thereof.

As used above:

the term "halo," unless otherwise indicated, includes chloro, fluoro, bromo and iodo;

the term "alkyl", unless otherwise indicated, includes saturated monovalent hydrocarbon radicals having straight, branched or cyclic moieties or combinations thereof, for example methyl, ethyl, n-propyl, isopropyl, n-butyl, isobutyl and t-butyl;

the term "alkenyl," unless otherwise indicated, means straight or branched unsaturated hydrocarbon radicals, for example, ethenyl, 1- or 2-propenyl, 2-methyl-1 propenyl and 1- or 2-butenyl;

the term "cycloalkyl," unless otherwise indicated, means a saturated carbocyclic radical, for example, cyclopropyl, cyclobutyl, cyclopentyl and cyclohexyl; and the term "alkoxy", unless otherwise indicated, includes O-alkyl groups wherein "alkyl" is defined as above.

Some examples of $AT_2$ receptor antagonists include those wherein W has the formula:

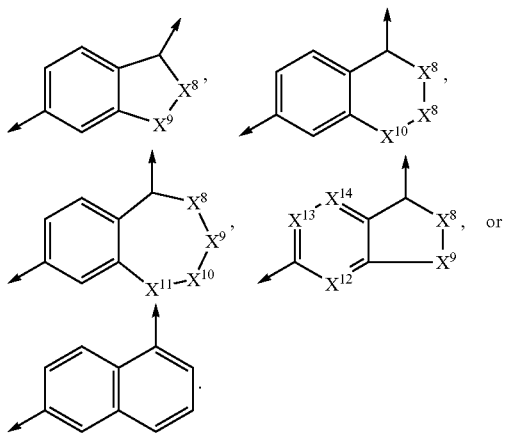

Examples of some specific $AT_2$ receptor antagonists based on Formula VII are:

2-butyl-5-chloro-1-{5-[2-(1H-tetrazol-5-yl)-phenyl]-indan-1-yl}-1H-imidazole-4-carboxylic acid ethyl ester;

2-butyl-5-chloro-1-{5-[2-(1H-tetrazol-5-yl)-phenyl]-indan-1-yl}-1H-imidazole-4-carboxylic acid;

2-butyl-3-{5-[2-(1H-tetrazol-5-yl)-phenyl]-indan-1-yl}-1,3-diazaspiro[4.4]non-1-en-4-one;

(2-butyl-5-chloro-1-{5-[2-(1H-tetrazol-5-yl)-phenyl]-indan-1-yl}-1H-imidazol-4-yl)methanol 2-ethyl-5,7-dimethyl-3-{5-[2-(1H-tetrazol-5-yl)-phenyl}-indan-1-yl}-3H-imidazole[4,5-b]pyridine;

(S)-2-ethyl-5,7-dimethyl-3-{5-[2-(1H-tetrazol-5-yl)-phenyl]-indan-1-yl}-3H-imidazo[4,5-b]pyridine;

(R)-2-ethyl-5,7-dimethyl-3-{5-[2-(1H-tetrazol-5-yl)-phenyl]-indan-1-yl}-3H-imidazol[4,5-b]pyridine;

2-ethyl-7-methyl-3-{5-[2-(1H-tetrazol-5-yl)-phenyl}-indan-1-yl}-3H-imidazo[4,5-b]pyridine;

5,7-dimethyl-2-propyl-3-{5-[2-(1H-tetrazol-5-yl)-phenyl]-indan-1-yl}-3H-imidazo[4,5-b]pyridine;

2-cyclopropyl-5,7-dimethyl-3-{5-[2-(1H-tetrazol-5-yl)-phenyl]-indan-1-yl}-3H-imidazo[4,5-b]pyridine;

2-butyl-5,7-dimethyl-3-{5-[2-(1H-tetrazol-5-yl)-phenyl]-indan-1-yl}-3H-imidazo[4,5-b]pyridine;

2-butyl-3-{5-[2-(1H-tetrazol-5-yl)-phenyl]-indan-1-yl}-3H-imidazo[4,5-b]pyridine;

2-[1-(2-ethyl-5,7-dimethyl-imidazo[4,5-b]pyridin-3-yl)-indan-5-yl-benzoic acid;

2-[5-(2-ethyl-5,7-dimethyl-imidazo[4,5-b]pyridin-3-yl)-5,6,7,8-tetrahydro-4H-naphthalen-2-yl]-benzoic acid;

2-ethyl-5,7-dimethyl-3-{6-[2-(1H-tetrazol-5-yl)-phenyl]-1,2,3,4-tetrahydro-4H-naphthalen-1-yl}-3H-imidazo[4,5-b]pyridine;

2-ethyl-5,7-dimethyl-3-{2-[2-(1H-tetrazol-5-yl)-phenyl]-6,7,8,9-tetrahydro-5H-benzocyclohepten-5-yl}-3H-imidazo[4,5-b]pyridine;

2-ethyl-5,7-dimethyl-3-{7-[2-(1H-tetrazol-5-yl)-phenyl]-chroman-4-yl}-3H-imidazo[4,5-b]pyridine;

2-ethyl-5,7-dimethyl-3-{3-[2-(1H-tetrazol-5-yl)-phenyl]-bicyclo[4.2.0]octa-1,3,5-trien-7-yl}-3H-imidazo[4,5-b]pyridine;

2-ethyl-5,7-dimethyl-3-{7-[2-(1H-tetrazol-5-yl)-phenyl]-chroman-4-yl}-3H-imidazo[4,5-b]pyridine;

2-ethyl-5,7-dimethyl-3-{3-[2-(1H-tetrazol-5-yl)-phenyl]-6,7-dihydro-5H-[1]pyridin-7-yl}-3H-imidazo[4,5-b]pyridine;

2-[5-(2-butyl-imidazo[4,5-b]pyridin-3-yl)-naphthalen-2-yl]-benzoic acid;

2-butyl-3-{6-[2-(1H-tetrazol-5-yl)-phenyl]-naphthalen-1-yl}3H-imidazo[4,5-b]pyridine; and 2-ethyl-5,7-dimethyl-3-{6-[2-(1H-tetrazol-5-yl)-phenyl-naphthalen-1-yl}-3H-imidazo[4,5-b]pyridine.

Other $AT_2$ receptor antagonists include the following compounds:

2-ethyl-5,7-dimethyl-3-{7-[2-(2H-tetrazol-5-yl)-phenyl]-thiochroman-4-yl}-3H-imidazo[4,5-b]pyridine;

3-{1,1-dioxo-7-[2-(2H-tetrazol-5-yl)-phenyl]-thiochroman-4-yl}-2-ethyl-5,7-dimethyl-3H-imidazo[4,5-b]pyridine;

2-ethyl-5,7-dimethyl-3-{2-[2-(2H-tetrazol-5-yl)-phenyl]-5,6-dihydro-4H-thieno[2,3-b]thiopyran-4-yl}-3H-imidazo[4,5-b]pyridine;

2-ethyl-5,7-dimethyl-3-{2-[2-(2H-tetrazol-5-yl)-phenyl] 4,5,6,7-tetrahydrobenzo[b]thiophen-4-yl}-3H-imidazo[4,5-b]pyridine; P0 2-ethyl-5,7-dimethyl-3-{2-[2-(2H-tetrazol-5-yl)-phenyl]-5,6-dihydro-4H-cyclopenta[b]thiophen-4-yl}-3H-imidazo[4,5-b]pyridine;

2-ethyl-5,7-dimethyl-3-{6-[2-(2H-tetrazol-5-yl)-phenyl]-3,4-dihydro-2H-thieno[2,3-b]pyran-4-yl}-3H-imidazo[4,5-b]pyridine;

2-ethyl-5,7-dimethyl-3-{2-[2-(2H-tetrazol-5-yl)-phenyl]-6,7-dihydro-5H-[1]pyridin-5-yl}-3H-imidazo[4,5-b]pyridine;

5-(2-ethyl-5,7-dimethyl-imidazo[4,5-b]pyridin-3-yl)-2-[2-(2H-tetrazol-5-yl)-phenyl]-5,6,7,8-tetrahydro-quinoline;

4-(2-ethyl-5,7-dimethyl-imidazo[4,5-b]pyridin-3-yl)-7-[2-(2H-tetrazol-5-yl)-phenyl]-3,4-dihydro-2H-thiopyrano[2,3-b]pyridine-1,1-dioxide;

2-ethyl-5,7-dimethyl-3-{2-[2-(2H-tetrazol-5-yl)-phenyl]-6,7-dihydro-5H-cyclopentapyrimidin-5-yl}-3H-imidazo[4,5-b]pyridine;

2-ethyl-5,7-dimethyl-3-{3-[2-(2H-tetrazol-5-yl)-phenyl]-6,7-dihydro-5H-[2]pyrindin-7-yl}-3H-imidazo[4,5-b]pyridine;

2-ethyl-5,7-dimethyl-3-{5-[3-(2H-tetrazol-5-yl)-thiophen-2-yl]-indan-1-yl}-3H-imidazo[4,5-b]pyridine;

2-ethyl-5,7-dimethyl-3-{5-[2-(2H-tetrazol-5-yl)-thiophen-3-yl]-indan-1-yl}-3H-imidazo[4,5-b]pyridine;

2-ethyl-5,7-dimethyl-3-{5-[4-(2H-tetrazol-5-yl)-thiophen-3-yl]-indan-1-yl}-3H-imidazo[4,5-b]pyridine;

2-ethyl-5,7-dimethyl-3-{5-[3-(2H-tetrazol-5-yl)-pyridin-4-yl]-indan-1-yl}-3H-imidazo[4,5-b]pyridine;

2-ethyl-5,7-dimethyl-3-{5-[4-(2H-tetrazol-5-yl)-pyridin-3-yl]-indan-1-yl}-3H-imidazo[4,5-b]pyridine;

2-ethyl-5,7-dimethyl-3-{5-[3-(2H-tetrazol-5-yl)-pyridin-2-yl]-indan-1-yl}-3H-imidazo[4,5-b]pyridine;

(2-butyl-5-chloro-3-{5-[2-(2H-tetrazol-5-yl)-phenyl]-indan-1-yl}-3H-imidazole-4-yl)methanol;

2-butyl-5-chloro-3-{5-[2-(2H-tetrazol-5-yl)-phenyl]-indan-1-yl}-3H-imidazole-4-carboxylic acid;

2-butyl-5-(1,1,2,2,2-pentafluoro-ethyl)-3-{5-[2-(2H-tetrazol-5-yl)-phenyl]-indan-1-yl}-3H-imidazole-4-carboxylic acid;

2-butyl-5-ethyl-3-{5-[2-(2H-tetrazol-5-yl)-phenyl]-indan-1-yl}-3H-imidazole-4-carboxylic acid;

2-ethoxy-3-{5-[2-(2H-tetrazol-5-yl)-phenyl]-indan-1-yl}-3H-benzoimidazole-4-carboxylic acid;

b 2-ethylsulfanyl-3-{5-[2-(2H-tetrazol-5-yl)-phenyl]-indan-1-yl}-3H-benzoimidazole-4-carboxylic acid;

N-benzoyl-2-[1-(2-ethyl-5,7-dimethyl-imidazo[4,5-b]pyridin-3-yl)-indan-5-yl]-benzenesulfonamide; and N-{2-[1-(2-ethyl-5,7-dimethyl-imidazo[4,5-b]pyridin-3-yl)-indan-5-yl]-phenyl}-benzenesulfonamide.

In another embodiment, the $AT_2$ receptor antagonist may be any antagonist previously described in WO 2006/066361 and U.S. Pub. No. 2006/0223741 A1, which are incorporated by reference herein in their entirety.

For example, the $AT_2$ receptor antagonist may be a compound of Formula (VIII):

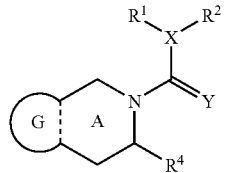

wherein:

$R^1$ and $R^2$ are independently selected from H, benzyl, substituted benzyl, phenyl, substituted phenyl, $C_{1-6}$alkyl, substituted C $C_{1-6}$alkyl, C $C_{3-6}$cycloalkyl, substituted C $C_{3-6}$cycloalkyl, and heteroaryl, providing that both $R^1$ and $R^2$ are not hydrogen, $R^4$ is selected from a carboxylate, carboxylic acid, sulfate, phosphate, sulfonamide, phosphonamide or amide, X is selected from CH, nitrogen, sulfur or oxygen with the proviso that when $R^4$ is sulfur or oxygen one of $R^1$ or $R^2$ is absent, Y is selected from sulfur, oxygen or N—$R^N$, where $R^N$ is selected from H, C1 6alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, G is a five or six membered, homoaromatic or unsaturated, substituted or unsubstituted, heterocyclic ring including but not limited to the following rings systems:

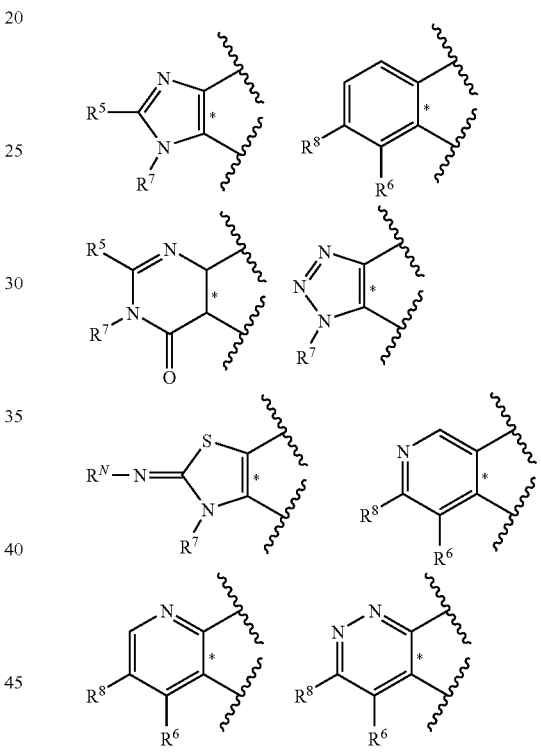

where the symbol '*' indicates the bond shared between the fused rings 'A' and 'G', $R^5$ is selected from H, $C_{1-6}$alkyl, phenyl, substituted phenyl, substituted $C_{1-6}$alkyl, $C_{1-6}$alkoxy, or substituted $C_{1-6}$alkoxy, $R^6$ and $R^8$ are independently selected from H, $C_{1-6}$alkyl, substituted $C_{1-6}$alkyl, $C_{1-6}$alkoxy, substituted $C_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of $R^6$ or $R^8$ is not hydrogen, and $R^7$ is selected from phenyl, substituted phenyl, benzyl, substituted benzyl, biphenyl, substituted biphenyl, biphenylmethylene, substituted biphenylmethylene, napthyl, substituted napthyl, napthylmethylene, and/or a pharmaceutically compatible salt thereof.

In another example, the AT$_2$ receptor antagonist may be a compound selected from compounds represented by Formula (IX):

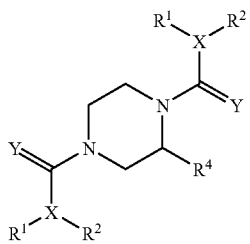

wherein:

R$^1$ and R$^2$ are independently selected from H, phenyl, substituted phenyl, benzyl, substituted benzyl, C$_{1-6}$alkyl, substituted C$_{1-6}$alkyl, C$_{3-6}$cyloalkyl, substituted C$_{3-6}$cycloalkyl, heteroaryl, and substituted heteroaryl, substituted biphenylmethylene and saturated and unsaturated substituted biphenylmethylene, provided that one of R$^1$ or R$^2$ is not hydrogen, R$^4$ is selected from a carboxylate, carboxylic acid, sulfate, phosphate, sulfonamide, phosphonamide or amide, X is selected from CH, nitrogen, sulfur or oxygen with the proviso that when R$^4$ is sulfur or oxygen one of R$^1$ or R$^2$ is absent, and Y is selected from sulfur, oxygen or N—R$^N$, where R$^N$ is selected from H, C$_{1-6}$alkyl, substituted C$_{1-6}$alkyl, aryl, substituted aryl, benzyl, substituted benzyl, C$_{1-4}$alkylaryl, substituted C$_{1-4}$alkylaryl, OH, or NH$_2$, or a pharmaceutically compatible salt thereof.

In yet another example, the AT$_2$ receptor antagonist may be selected from compounds represented by Formula (X):

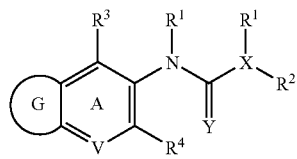

wherein:

R$^1$, R$^2$ and R$^3$ are independently selected from H, phenyl, substituted phenyl, benzyl substituted benzyl, C$_{1-6}$alkyl, substituted C$_{1-6}$alkyl, with the proviso that at least one of R$^1$ or R$^2$ are not hydrogen, X is selected from CH, nitrogen, sulfur or oxygen with the proviso that when R$^4$ is sulfur or oxygen, one of R$^1$ or R$^2$ is absent, or is aryl or heteroaryl with the proviso that both R$^1$ and R$^2$ are absent, V is selected from CH or nitrogen atom, Y is selected from sulfur, oxygen or N—R$^N$, where R$^N$ is selected from H, C$_{1-6}$alkyl, substituted C$_{1-6}$alkyl, aryl, substituted aryl, benzyl, substituted benzyl, C$_{1-4}$alkylaryl, substituted C$_{1-4}$alkylaryl, OH, or NH$_2$, R$^4$ is selected from a carboxylate, carboxylic acid, sulfate, phosphate, sulfonamide, phosphonamide, or amide, G is a five or six membered, homoaromatic or unsaturated, substituted or unsubstituted, heterocyclic ring including but not limited to the following rings systems:

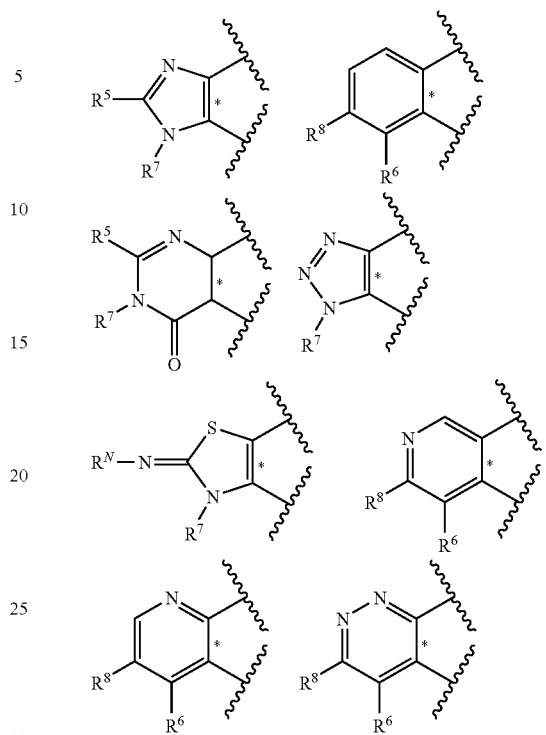

where the symbol '*' indicates the bond shared between the fused rings 'A' and 'G', R$^5$ is selected from H, C$_{1-6}$alkyl, phenyl, substituted phenyl, substituted C$_{1-6}$alkyl, or C$_{1-6}$alkoxy, R$^6$ and R$^8$ are independently selected from H, C$_{1-6}$alkyl, substituted C$_{1-6}$alkyl, C$_{1-6}$alkoxy, substituted C$_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of R$^6$ or R$^8$ is not hydrogen, and R$^7$ is selected from phenyl, substituted phenyl, benzyl, substituted benzyl, biphenyl, substituted biphenyl, biphenylmethylene, substituted biphenylmethylene, napthyl, substituted napthyl, napthylmethylene, and/or a pharmaceutically compatible salt thereof.

In yet another embodiment, the AT$_2$ receptor antagonist may be selected from compounds represented by Formula (XI):

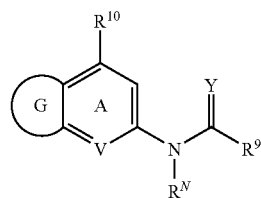

wherein:

R$^{10}$ is selected from H, halogen, C$_{1-6}$alkyl, phenyl, substituted phenyl, substituted C$_{1-6}$alkyl, or C$_{1-6}$alkoxy, R$^9$ is selected from —NR$^{13}$R$^{14}$, wherein R$^{13}$ and R$^{14}$ are independently selected from C$_{1-6}$alkyl, substituted C$_{1-6}$alkyl, aryl, substituted aryl, benzyl, substituted benzyl, C$_{1-4}$alkylaryl, substituted C$_{1-4}$alkylaryl, OH, or NH$_2$; a five or six membered, saturated or unsaturated, substituted or unsubstituted, carbocyclic or heterocyclic ring including but not limited to:

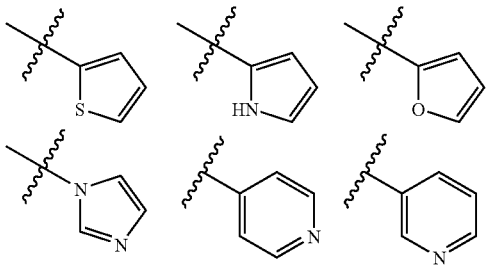

V is selected from CH or a nitrogen atom,

Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, G is a five or six membered homoaromatic or heterocyclic, unsaturated, substituted ring including but not limited to the following rings systems:

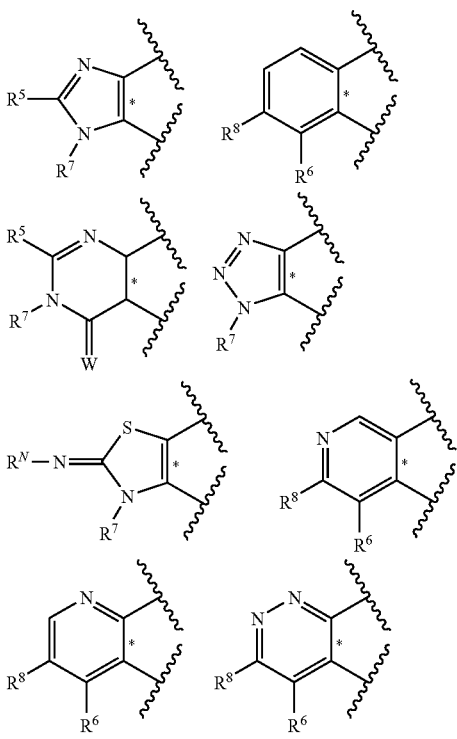

where the symbol '*' indicates the bond shared between the fused rings 'A' and 'G', $R^5$ is selected from $C_{1-6}$alkyl, phenyl, substituted phenyl, substituted $C_{1-6}$alkyl, or $C_{1-6}$alkoxy, $R^6$ and $R^8$ are independently selected from H, $C_{1-6}$alkyl, substituted $C_{1-6}$alkyl $C_{1-6}$alkoxy, substituted, $C_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of $R^6$ or $R^8$ is not hydrogen, and $R^7$ is selected from phenyl, substituted phenyl, benzyl, substituted benzyl, biphenyl, substituted biphenyl, biphenylmethylene, substituted biphenylmethylene, napthyl, substituted napthyl, napthylmethylene, and/or a pharmaceutically compatible salt thereof.

In yet another embodiment, the $AT_2$ receptor antagonist may be selected from compounds represented by the Formula (XII):

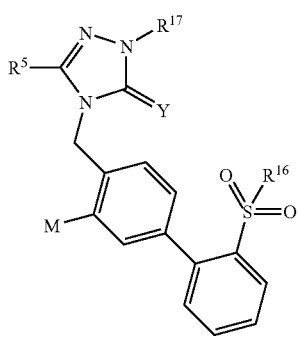

wherein:

M is H or a halogen (fluoro, bromo, iodo, chloro), $R^5$ is selected from $C_{1-6}$alkyl, phenyl, substituted phenyl, substituted $C_{1-6}$alkyl, or $C_{1-6}$alkoxy, $R^{16}$ is selected from $C_{1-6}$alkylamino, $C_{1-6}$-dialkylamino, substituted $C_{1-6}$alkylamino, substituted dialkylamino, arylamino, diarylamino, substituted arylamino, substituted diarylamino, alkylarylamino, dialkylarylamino, substituted alkylarylamino, substituted dialkylarylamino, heteroarylamino, substituted heteroarylamino, cycloalkylamino, dicycloalkylamino, diheteroarylamino, alkylcarbonylamino, arylcarbonylamino, alkylarylcarbonylamino, cycloalkylcarbonylamino, and $R^{17}$ is selected from $C_{1-6}$alkyl, substituted $C_{1-6}$alkyl, phenyl, substituted phenyl, benzyl, substituted benzyl, biphenyl, substituted biphenyl, biphenylmethylene, substituted biphenylmethylene, naphthyl, substituted naphthyl, heteroaryl, or substituted heteroaryl, or a pharmaceutically compatible salt thereof.

In yet another embodiment, the $AT_2$ receptor antagonist may be selected from $AT_2$ receptor antagonist peptides illustrative examples of which include hexa-, hepta-, and octapeptides represented by Formula (XIII):

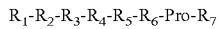

$R_1$-$R_2$-$R_3$-$R_4$-$R_5$-$R_6$-Pro-$R_7$ wherein:

$R_1$ is absent or is selected from hydrogen, succinyl, L-aspartyl, sarcosyl, L-seryl, succinamyl, L-propyl, glycyl, L-tyrosyl, $N_\alpha$-nicotinoyl-tyrosyl, or D- or L-asparagyl;

$R_2$ is selected from arginyl or N-benzoylcarbonyl arginyl;

$R_3$ is absent or valyl;

$R_4$ is absent or is selected from L-phenylalanyl or L-tyrosyl;

$R_5$ is selected from valyl, L-isoleucyl, L-alanyl or L-lysyl;

$R_6$ is selected from L-histidyl, L-isoleucyl, L-tyrosyl or p-aminophenylalanyl; and $R_7$ is selected from L-alanine, L-tyrosine, L- or D-leucine, glycine, L-isoleucine or β-alanine residue; or a pharmaceutically compatible salt thereof.

Representative examples according to formula (XIII) include, but are not limited to:

```
H-Asn-Arg-Val-Tyr-Val-His-Pro-Ala-OH                              (SEQ ID NO: 1)

H-Asn-Arg-Val-Tyr-Val-His-Pro-Leu-OH                              (SEQ ID NO: 2)

Succinyl-Arg-Val-Tyr-Val-His-Pro-Ala-OH                           (SEQ ID NO: 3)

H-Asp-Arg-Val-Tyr-Val-His-Pro-Ala-OH                              (SEQ ID NO: 4)

H-Arg-Val-Tyr-Val-His-Pro-Ala-OH                                  (SEQ ID NO: 5)

H-Sar-Arg-Val-Tyr-His-Pro-Ala-OH                                  (SEQ ID NO: 6)

H-Ser-Arg-Val-Tyr-His-Pro-Ala-OH                                  (SEQ ID NO: 7)

Succinarnyl-Arg-Val-Tyr-Val-His-Pro-Ala-OH                        (SEQ ID NO: 8)

H-Asn-Arg-Val-Tyr-Val-His-Pro-Gly-OH                              (SEQ ID NO: 9)

H-Asn-Arg-Val-Tyr-Val-His-Pro-Ile-OH                              (SEQ ID NO: 10)

H-Sar-Arg-Val-Tyr-Val-His-Pro-Gly-OH                              (SEQ ID NO: 11)

H-Pro-Arg-Val-Tyr-Val-His-Pro-Gly-OH                              (SEQ ID NO: 12)

H-Asn-Arg-Val-Tyr-Val-His-Pro-Gly-OH                              (SEQ ID NO: 13)

H-Sar-Arg-Val-Tyr-Val-His-Pro-β-Ala-OH                            (SEQ ID NO: 14)

H-Asn-Arg-Val-Tyr-Val-His-Pro-β-Ala-OH                            (SEQ ID NO: 15)

H-Gly-Arg-Val-Tyr-Val-His-Pro-Ala-OH                              (SEQ ID NO: 16)

H-Sar-Arg-Val-Tyr-Ile-His-Pro-Leu-OH                              (SEQ ID NO: 17)

H-Asn-Arg-Val-Tyr-Val-His-Pro-Leu-OH                              (SEQ ID NO: 18)

H-Sar-Arg-Val-Tyr-Ile-His-Pro-Ala-OH,                             (SEQ ID NO: 19)

also known as saralasin;

H-Asn-Arg-Val-Tyr-Ile-His-Pro-Ala-OH                              (SEQ ID NO: 20)

H-Asn-Arg-Val-Tyr-Ala-His-Pro-Ala-OH                              (SEQ ID NO: 21)

H-Asp-Arg-Val-Phe-Ile-His-Pro-Tyr-OH,                             (SEQ ID NO: 22)

also known as Phe$^4$-Tyr$^8$-Ang II; and

H-Asp-Arg-Val-Tyr-Ile-p-NH$_2$-Phe-Pro-Phe-OH,                    (SEQ ID NO: 23)

also known as [p-NH$_2$Phe$^6$-Ang II; and nicotinic acid-Tyr-(N-benzoylcarbonyl-Arg)-Lys-His-Pro-Ile-OH,    (SEQ ID NO: 24)

also known as CGP-42112A.
```

In other embodiments, the AT$_2$ receptor antagonist may be selected from antigen-binding molecules that are immuno-interactive with an AT$_2$ receptor polypeptide. Illustrative antigen-binding molecules include whole polyclonal antibodies. Such antibodies may be prepared, for example, by injecting an AT$_2$ receptor polypeptide or fragment thereof into a production species, which may include mice or rabbits, to obtain polyclonal antisera. Methods of producing polyclonal antibodies are well known to those skilled in the art. Exemplary protocols which may be used are described for example in Coligan et al., "Current Protocols In Immunology", (John Wiley & Sons, mc, 1991), and Ausubel et al., ("Current Protocols in Molecular Biology", John Wiley & Sons mc, 1994-1998), in particular Section III of Chapter 11.

In lieu of the polyclonal antisera obtained in the production species, monoclonal antibodies may be produced using the standard method as described, for example, by Köhler and Milstein (1975, Nature 256, 495-497), or by more recent modifications thereof as described, for example, in Coligan et al., (1991, supra) by immortalizing spleen or other antibody-producing cells derived from a production species which has been inoculated with an AT$_2$ receptor polypeptide or fragment thereof.

The invention also contemplates as antigen-binding molecules Fv, Fab, Fab' and F(ab')$_2$ immunoglobulin fragments. Alternatively, the antigen-binding molecule may be in the form of a synthetic stabilized Fv fragment, a single variable region domain (also known as a dAbs), a "minibody" and the like as known in the art.

Also contemplated as antigen binding molecules are humanized antibodies. Humanized antibodies are produced by transferring complementary determining regions from heavy and light variable chains of a non human (e.g., rodent, preferably mouse) immuno globulin into a human variable domain. Typical residues of human antibodies are then substituted in the framework regions of the non human counterparts. The use of antibody components derived from humanized antibodies obviates potential problems associated with the immunogenicity of non human constant regions. General techniques for cloning non human, particularly murine, immunoglobulin variable domains are described, for example, by Orlandi et al. (*Proc. Natl. Acad. Sci. USA,* 86:3833 (1989)). Techniques for producing humanized monoclonal antibodies are described, for example, by Jones et al. (*Nature,* 321:522 (1986)), Carter et al. (*Proc. Natl. Acad. Sci. USA,* 89:4285 (1992)), Sandhu (*Crit. Rev. Biotech.,* 12:437 (1992)), Singer et al. (*J. Immun.,* 150:2844 (1993)), Sudhir (ed., Antibody Engineering Protocols, Humana Press, Inc. (1995)), Kelley ("Engineering Therapeutic Antibodies," *Protein Engineering: Principles and Practice* Cleland et al. (eds.), pages 399-434 (John Wiley & Sons, Inc. 1996), and by Queen et al., U.S. Pat. No. 5,693,762 (1997).

Illustrative antigen-binding molecules that are immuno-interactive with $AT_2$ receptor polypeptides and methods for their preparation are described by Nora et al. (*Am J. Physiol.,* 275(4 Pt 2):H1395403 (1998)), Yiu et al. (*Regul Pept.,* 70(1): 15-21 (1997)), Reagan et al. (*Proc Natl Acad Sci USA,* 90(17):7956-7960 (1993)), Rakugi et al. (*Hypertens Res.,* 20(1):51-55 (1997)) and Wang et al. (*Hypertension,* 32(I):78-83 (1998)), and some are available commercially, such as but not limited to H-143 (Santa Cruz Biotechnology, Santa Cruz, Calif.), which is directed against amino acid residues 221-363 from the carboxy terminus of human $AT_2$, $rAT_2$ (Ab #1), which is directed against an 18-residue C-terminal fragment of rat $AT_2$), $rAT_2$ (Ab #2) which is directed against an 18-residue C-terminal fragment of rat $AT_2$) aiid $rAT_2$ (Ab #3), which is directed against a 10-residue N-terminal fragment of rat $AT_2$ (Alpha Diagnostic International, Inc.-5415 Lost Lane, SA).

In still other embodiments, the $AT_2$ receptor antagonist may be selected from nucleic acid molecules that inhibit or otherwise reduce the level or functional activity of an expression product of an $AT_2$ gene, illustrative examples of which include antisense molecules, ribozymes and RNAi molecules. Thus, $AT_2$ receptor antagonist may include antisense RNA and DNA molecules as well as ribozymes and RNAi molecules that function to inhibit the translation, for example, of Agtr2 mRNA. Antisense RNA and DNA molecules act to directly block the translation of mRNA by binding to targeted mRNA and preventing protein translation.

In regard to antisense DNA, oligodeoxyribonucleotides derived from the translation initiation site, e.g., between −10 and +10 regions of an Agtr2 gene, may be desirable. Exemplary antisense oligonucleotides may be derived from any nucleic acid molecule that encodes an $AT_2$ receptor, such as those described in U.S. Pat. No. 5,556,780, and in U.S. Pub. No. 2003/0083339. Therapeutic methods utilizing antisense oligonucleotides have been described in the art, for example, in U.S. Pat. Nos. 5,627,158 and 5,734,033. Generally, antisense molecules comprise from about 8 to about 30 bases (i.e., from about 8 to about 30 linked nucleosides) and typically comprise from about 12 to about 25 bases.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Within the scope of the invention are engineered hammerhead motif ribozyme molecules that specifically and efficiently catalyze endonucleolytic cleavage of Agtr2 RNA sequences. Specific ribozyme cleavage sites within any potential RNA target are initially identified by scanning the target molecule for ribozyme cleavage sites which include the following sequences, GUA, GUU and GUC. Once identified, short RNA sequences of between and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both antisense RNA and DNA molecules and ribozymes may be prepared by any method known in the art for the synthesis of nucleic acid molecules. These include techniques for chemically synthesizing oligodeoxyribonucleotides well known in the art, such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to nucleic acid molecules may be introduced as a means of increasing intracellular stability and half-life. Possible modifications include but are not limited to the addition of flanking sequences of ribo- or deoxy-nucleotides to the 5' and/or 3' ends of the molecule or the use of artificial linkages rather than phosphodiesterase linkages within the oligodeoxyribonucleotide backbone. Illustrative modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino pl1osphoramidate and aminoalkylphosphoramidates, thionophosphoramidates, thionoalkylphosphonates, thionoalkylphosphotriesters, and boranophosphates having normal 3'-5' linkages, 2'-S' linked analogs of these, and those having inverted polarity wherein the adjacent pairs of nucleoside units are linked 3'-5' to 5'-3' or 2'-5' to 5'-2'. Various salts, mixed salts and free acid forms are also included.

Other agents that may be used to decrease the expression of an Agtr2 gene or the level and/or functional activity of an expression product of that gene include RNA molecules that mediate RNA interference (RNAi) of a Agtr2 gene or gene transcript. RNAi refers to interference with or destruction of the product of a target gene by introducing a single stranded, and typically a double stranded RNA (dsRNA), which is homologous to the transcript of the target gene. Thus, in one embodiment, dsRNA per se and especially dsRNA-producing constructs that encode an amino acid sequence corresponding to at least a portion of an $AT_2$ receptor polypeptide may be used to decrease its level and/or functional activity. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a target gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts which then anneal to form a dsRNA having homology to a target gene.

Absolute homology is not required for RNAi, with a lower threshold being described at about 85% homology for a dsRNA of about 200 base pairs (Plasterk and Ketting, 2000, *Current Opinion in Genetics and Dev.* 10: 562-567). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, may be at least about 100 nucleotides in length. RNA-encoding constructs that express a single RNA designed to form a dsRNA via internal folding may be at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In another embodiment, RNA molecules of about 21 to about 23 nucleotides, which direct cleavage of specific mRNA to which they correspond, as for example described by Tuschl et al. in U.S. Pub. No. 2002/0086356, can be utilized for mediating RNAi. Such 21-23 nt RNA molecules may comprise a 3' hydroxyl group, may be single-stranded or double stranded (as two 21-23 nt RNAs) wherein the dsRNA molecules can be blunt ended or comprise overhanging ends (e.g., 5', 3').

In yet another embodiment, the $AT_2$ receptor antagonist may be selected from compounds, or pharmaceutically compatible salts thereof, represented by Formula (XIV):

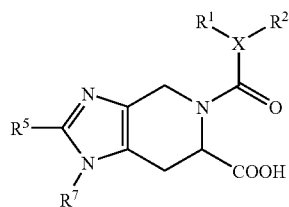

wherein:

X is selected from CH or nitrogen, $R^1$ and $R^2$ are independently selected from phenyl, substituted phenyl, benzyl, substituted benzyl, $C_{1-6}$alkyl, substituted $C_{1-6}$alkyl, $C_{3-6}$cycloalkyl, substituted $C_{3-6}$cycloalkyl and heteroaryl, $R^5$ is selected from hydrogen, $C_{1-6}$alkyl, phenyl, substituted phenyl, substituted $C_{1-6}$alkyl, $C_{1-6}$alkoxy, and substituted $C_{1-6}$alkoxy, and $R^7$ is selected from phenyl, substituted phenyl, benzyl, substituted benzyl, biphenyl, substituted biphenyl, biphenylmethylene, substituted biphenylmethylene, napthyl, substituted napthyl, napthylmethylene, and substituted napthylmethylene.

In another embodiment, the $AT_2$ receptor antagonist may be a compound, or pharmaceutically compatible salt thereof, represented by the Formula (XIV), wherein $R^1$ and $R^2$ are phenyl, X is CH, $R^5$ is hydrogen or $C_{1-4}$alkyl, and $R^7$ is selected from substituted benzyl.

In yet another embodiment, the $AT_2$ receptor antagonist may be AT2 receptor antagonist is selected from compounds, or pharmaceutically compatible salts thereof, represented by the Formula (XIV), $R^5$ is hydrogen and $R^7$ is selected from 4-(N,N-dimethylamino)-3-methylbenzyl, 4-methoxy-3-methylbenzyl, 4-amino-3-methylbenzyl.

In yet another embodiment, the $AT_2$ receptor antagonist may be selected from compounds, or pharmaceutically compatible salts thereof, represented by the Formula (XV):

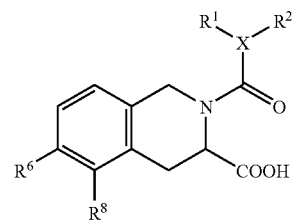

wherein:

X is selected from CH or nitrogen, $R^1$ and $R^2$ are independently selected from phenyl, substituted phenyl, benzyl, substituted benzyl, $C_{1-6}$alkyl, substituted $C_{1-6}$alkyl, $C_{3-6}$cycloalkyl, substituted $C_{3-6}$cycloalkyl and heteroaryl, and $R^6$ and $R^8$ are independently selected from H, $C_{1-6}$alkyl, substituted $C_{1-6}$alkyl $C_{1-6}$alkoxy, substituted, $C_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of $R^6$ or $R^8$ is not hydrogen.

In another embodiment, the $AT_2$ receptor antagonist may be selected from compounds, or pharmaceutically compatible salts thereof, represented by the Formula (XV), wherein $R^1$ and $R^2$ are independently selected from phenyl or substituted phenyl, X is CH, $R^4$ is a carboxylic acid, $R^6$ is selected from $C_{1-6}$alkyl, substituted $C_{1-6}$alkyl $C_{1-6}$alkoxy, substituted $C_{1-6}$alkoxy, phenyl, phenyloxy, and $R^8$ is selected from H, phenyl, phenyloxy, benzyl, benzyloxy, benzylamino, biphenyl, substituted biphenyl, biphenyloxy, substituted biphenyloxy, napthyl, and substituted napthyl.

In yet another embodiment, the $AT_2$ receptor antagonist is selected from compounds, or pharmaceutically compatible salts thereof, represented by Formula (XVI):

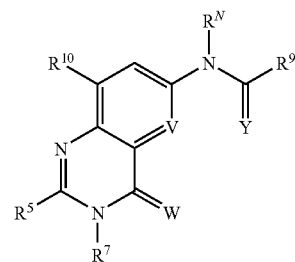

wherein:

V is selected from CH or a nitrogen atom,

Y and W are independently selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, $R^5$ is selected from $C_{1-6}$alkyl, phenyl, substituted phenyl, substituted $C_{1-6}$alkyl, or $C_{1-6}$alkoxy, $R^7$ is selected from phenyl, substituted phenyl, benzyl, substituted benzyl, biphenyl, substituted biphenyl, biphenylmethylene, substituted biphenylmethylene, napthyl, substituted napthyl, napthylmethylene, and $R^9$ is selected from —$NR^{13}R^{14}$, wherein $R^{13}$ and $R^{14}$ are independently selected from $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$; a five or six membered, saturated or unsaturated, substituted or unsubstituted, carbocyclic or heterocyclic ring including but not limited to:

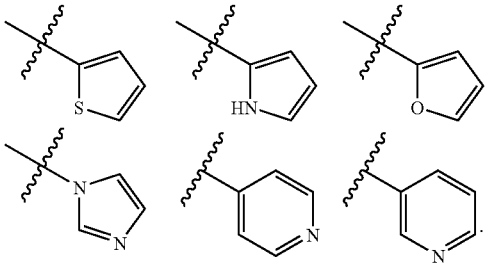

and $R^{10}$ is selected from H, halogen, $C_{1-6}$alkyl, phenyl, substituted phenyl, substituted $C_{1-6}$alkyl, or $C_{1-6}$alkoxy.

In another embodiment, the $AT_2$ receptor antagonist may be selected from compounds, or pharmaceutically compatible salts thereof, represented by the Formula (XVI), wherein V is CH, Y and W are oxygen, $R^5$ is selected from $C_{1-6}$alkyl, phenyl, substituted phenyl, substituted $C_{1-6}$alkyl, or $C_{1-6}$alkoxy, $R^7$ is selected from biphenyl, substituted biphenyl, biphenylmethylene, substituted biphenylmethylene, napthyl, substituted napthyl, napthylmethylene, and substituted napthylmethylene, $R^N$ is selected from H, $C_{1-6}$alkyl, substituted $C_{1-6}$alkyl, aryl, substituted aryl, $C_{1-4}$alkylaryl, substituted $C_{1-4}$alkylaryl, OH, or $NH_2$, $R^9$ is selected from —$NR^{13}R^{14}$, wherein $R^{13}$ and $R^{14}$ are independently selected from $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$; a five or six membered, saturated or unsaturated, substituted or unsubstituted, carbocyclic or heterocyclic ring including but not limited to:

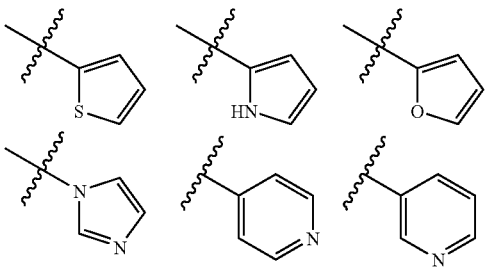

and $R^{10}$ is selected from H, halogen, $C_{1-6}$alkyl, phenyl, substituted phenyl, substituted $C_{1-6}$alkyl, or $C_{1-6}$alkoxy.

In another embodiment, the $AT_2$ receptor antagonist may be selected from compounds, or pharmaceutically compatible salts thereof, represented by the Formula (XVI), wherein V is CH, Y and W are oxygen, $R^5$ is selected from $C_{1-6}$alkyl, substituted $C_{1-6}$alkyl, or $C_{1-6}$alkoxy, $R^7$ is selected from biphenylmethylene, substituted biphenylmethylene, napthylmethylene, and substituted napthylmethylene, $R^N$ is selected from H, $C_{1-6}$alkyl, substituted $C_{1-6}$alkyl, aryl, substituted aryl, $C_{1-4}$alkylaryl, substituted $C_{1-4}$alkylaryl, $R^9$ is selected from —$NR^{13}R^{14}$, wherein $R^{13}$ and $R^{14}$ are independently selected from $C_{1-6}$alkyl, substituted $C_{1-6}$alkyl, aryl, substituted aryl, benzyl, substituted benzyl, $C_{1-4}$alkylaryl, substituted $C_{1-4}$alkylaryl; a five or six membered, saturated or unsaturated, substituted or unsubstituted, carbocyclic or heterocyclic ring including but not limited to:

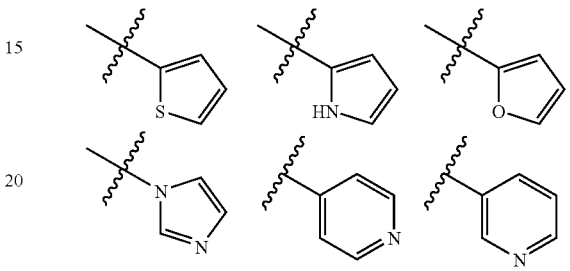

and $R^{10}$ is H.

In yet another embodiment, the $AT_2$ receptor antagonist may be selected from compounds, or pharmaceutically compatible salts thereof, represented by the formula XI, wherein $R^7$ is selected from a substituted biphenylmethylene group represented by Formula (XVII):

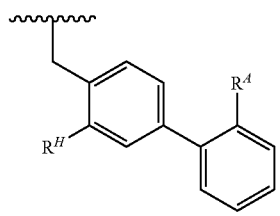

wherein:

$R^H$ is selected from hydrogen, —OH, —SH, —$HN_2$, nitrile, $CF_3$, halo (F, Cl, Br, I), —$NO_2$, $C_1$-$C_4$alkylamino, $C_1$-$C_4$dialkylamino, and $R^A$ is selected from $C_1$-$C_{10}$alkyl, $C_3$-$C_{10}$alkenyl, $C_3$-$C_{10}$alkynyl, aryl, —($C_1$-$C_4$alkyl)aryl, heterocyclyl, heteroaryl, $C_3$-$C_7$-cycloalkyl, $C_1$-$C_4$-perfluoroalkyl, —OH, —SH, —$HN_2$, nitrile, $C_1$-$C_{10}$-alkoxy, halo$C_{1-4}$alkyl, hydroxy$C_{1-4}$alkyl, $C_1$-$C_{10}$-alkylthio, —$CF_3$, halo (F, Cl, Br, I), —$NO_2$, —$CO_2R^{23}$, —$NH_2$, $C_1$-$C_4$alkylamino, $C_1$-$C_4$dialkylamino, arylamino, diarylamino, aryl$C_{1-4}$alkylamino, aryl$C_{1-4}$dialkylamino, aryloxy, aryl$C_{1-4}$alkyloxy, formyl, $C_{1-10}$alkylcarbonyl and $C_{1-10}$alkoxycarbonyl, —$PO_3H_2$, —$CO_2H$, —$CONHSO_2R^{21}$, —$CONHSO_2NHR^{20}$, —$NHCONHSO_2R^{21}$, —$NHSO_2R^{21}$, —$NHSO_2NHCOR^{21}$, —$SO_2NHR^{20}$, —$SO_2NHCOR^{21}$, —$SO_2NHCONHR^{20}$, —$SO_2NHCO_2R^{21}$, tetrazolyl, —CHO, —$CONH_2$, —NHCHO, —CO—($C_1$-$C_6$ perfluoroalkyl), —S(O)$_r$—($C_1$-$C_6$ perfluoroalkyl), wherein $R^{20}$ is H, $C_1$-$C_5$-alkyl, aryl, —($C_1$-$C_4$-alkyl)-aryl, heteroaryl;

$R^{21}$ is aryl, $C_3$-$C_7$-cycloalkyl, $C_1$-$C_4$-perfluoroalkyl, $C_1$-$C_4$alkyl, optionally substituted with a substituent selected from the group consisting of aryl, heteroaryl, —OH, —SH, $C_1$-$C_4$-alkyl, $C_1$-$C_4$alkoxy, $C_1$-$C_4$alkylthio, —$CF_3$, halo, —NO$_2$, —CO$_2$R$^{23}$, —NH$_2$, C$_1$-C$_4$-alkylamino, C$_1$-C$_4$-dialkylamino, —PO$_3$H$_2$, or heteroaryl; and R$^{22}$ is selected from C$_1$-C$_6$-alkyl, C$_3$-C$_6$-cycloalkyl, aryl, —(C$_1$-C$_5$-alkyl)-aryl, or heteroaryl.

In another embodiment, AT$_2$ receptor antagonists, which are small molecule Ang II receptor antagonists may be used in the present invention. Examples of such Ang II receptor antagonists include those disclosed in U.S. Pat. Nos. 5,958,884 and 5,264,581; and other Ang II receptor type AT$_1$ and AT$_2$ receptor blockers as disclosed in U.S. Pat. No. 5,889,020, contents of which are incorporated by reference in their entirety.

In another embodiment, the AT$_2$ receptor antagonist may be PD123319 (Timmermans PBMWM, et al., "Angiotensin II receptors and angiotensin II antagonists," *Pharmacol Rev* 25:205-251 (1993); and Inagami T, "Recent progress in molecular and cell biological studies of angiotensin receptors," *Curr Opin Nephrol Hypertens* 4:47-54 (1995)).

In another embodiment, the AT$_2$ receptor antagonist may be CGP 42112B (Whitebread et al., "Preliminary biochemical characterization of two angiotensin II receptor subtypes," *Biochemical and Biophysical Research Communications* 163:284-291 (1989) and LeNoble et al., *The FASEB Journal*, 6(4):A937 (1992)).

In another embodiment, the AT$_2$ receptor antagonist may be WL 19 (Wiest S A, et al., *J Cardiovasc Pharmacol*, 17(2): 177-184 (1991)).

In yet another embodiment, the AT$_2$ receptor antagonist may be one selected from compounds listed in U.S. Pat. No. 6,444,646, contents of which is incorporated herein by reference in its entirety. For example, the AT$_2$ receptor antagonist comprises a sequence of the Formula (XVIII):

$$R^1-R^2-R^3-R^4-R^5-R^6-R^7-R^8$$

wherein R$^1$ is selected from the group consisting of Asp, Glu, Asn. Acpc, Ala, Me$^2$Gly, Pro, Bet, Glu(NH$_2$), Gly, Asp (NH$_2$), and Suc;

R$^2$ is selected from the group consisting of Arg, Lys, Ala, Orn Ser(Ac), Sar, D-Arg, and D-Lys;

R$^3$ is selected from the group consisting of Val, Ala, Leu, Ile, Gly, Pro, Aib, Acpc, and Tyr;

R$^4$ is selected from the group consisting of Tyr, Thr, Ser, and aza Tyr;

R$^5$ is selected from the group consisting of Ile, Ala, Leu, Val, and Gly;

R$^6$ is p-NH$_2$-Phe;

R$^7$ is Pro or Ala;

R$^8$ is selected from the group consisting of Phe, Phe(Br), Ile, and Tyr; and wherein the active agent is not Ang II.

In addition to the exemplary AT$_2$ receptor antagonists provided above, other known AT$_2$ receptor antagonists may be used in this invention.

B. Identification of AT$_2$ Receptor Antagonists

Various methods of screening for agents that antagonize an AT$_2$ receptor, including reducing the expression of an AT$_2$ gene (also known as an Agtr2 gene) or the level and/or functional activity of an expression product of that gene may be used. Exemplary methods of screening for antagonist compounds were previously described in International Pub. WO 2006/066361, contents of which are incorporated by reference herein in its entirety. A candidate agent identified according to these methods has an ability to reduce the biological activity or property of an AT$_2$ receptor polypeptide. For example, candidate agents may include antagonistic antigen-binding molecules, and inhibitor peptide fragments, antisense molecules, ribozymes, RNAi molecules and co-suppression molecules. Other candidate agents include small organic compounds having a molecular weight of more than 50 and less than about 2,500 Dalton and will typically comprise functional groups necessary for structural interaction with proteins, particularly hydrogen bonding, and typically include at least an amine, carbonyl, hydroxyl or carboxyl group, suitably at least two of the functional chemical groups. Candidate agents may often comprise cyclical carbon or heterocyclic structures or aromatic or polyaromatic structures substituted with one or more of the above functional groups. Candidate agents may also be found among biomolecules including, but not limited to: peptides, saccharides, fatty acids, steroids, purines, pyrimidines, derivatives, structural analogues or combinations thereof.

Small (non-peptide) molecule AT$_2$ receptor antagonists are generally advantageous because such molecules are more readily absorbed after administration, have fewer potential antigenic determinants, or are more likely to cross the cell membrane than larger, protein-based pharmaceuticals. Small organic molecules may also have the ability to gain entry into an appropriate cell and affect the expression of a gene (e.g., by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or may be readily produced. Additionally, natural or synthetically produced libraries and compounds may be readily modified through conventional chemical, physical and biochemical means, and may be used to produce combinatorial libraries. Known pharmacological agents may be subjected to directed or random chemical modifications, such as acylation, alkylation, esterification, amidification, etc to produce structural analogues.

Screening may also be directed to known pharmacologically active compounds and chemical analogues thereof.

For example, antagonist compounds may be identified by methods comprising the steps of: (1) contacting a preparation with a test agent, wherein the preparation contains (i) a polypeptide comprising an amino acid sequence corresponding to at least a biologically active fragment of an AT$_2$ receptor, or to a variant or derivative thereof; or (ii) a polynucleotide comprising at least a portion of a genetic sequence that regulates an AT$_2$ gene, which is operably linked to a reporter gene; and (2) detecting a decrease in the level and/or functional activity of the polypeptide, or an expression product of the reporter gene, relative to a normal or reference level and/or functional activity in the absence of the test agent, which indicates that the agent antagonizes the AT$_2$ receptor.

In illustrative examples of this type, the methods comprise the steps of establishing a control system comprising an AT$_2$ receptor polypeptide and a ligand which is capable of binding to the polypeptide; establishing a test system comprising an AT$_2$ receptor polypeptide, the ligand, and a candidate compound; and determining whether the candidate compound inhibits or otherwise reduces the functional activity of the polypeptide by comparison of the test and control systems. Representative ligands may include a compound described herein, and in these embodiments, the functional activity screened can include binding affinity.

In another example, the methods for identifying AT$_2$ receptor antagonist may include (a) incubating an AT$_2$ receptor polypeptide with a ligand (e.g., Ang II) in the presence of a test inhibitor compound; (b) determining an amount of ligand that is bound to the AT$_2$ receptor polypeptide, wherein decreased binding of ligand to the AT$_2$ receptor polypeptide in the presence of the test inhibitor compound relative to binding in the absence of the test inhibitor compound is indicative of inhibition; and (c) identifying the test compound as an $AT_2$ receptor antagonist if decreased ligand binding is observed. In other embodiments, the methods may include: (a) incubating a cell membrane, which comprises an $AT_2$ receptor polypeptide, with a first ligand (e.g., Ang II) in the presence of a test inhibitor compound; (b) optionally blocking any $AT_1$ receptors present on or in the membrane with a second ligand that binds specifically to the $AT_1$ receptor (e.g., losartan or candesartan) if the first ligand also binds to the $AT_1$ receptor; (c) determining an amount of first ligand that is bound to the membrane, wherein decreased binding of ligand to the membrane in the presence of the test inhibitor compound relative to binding in the absence of the test inhibitor compound is indicative of inhibition; and (d) identifying the test compound as $AT_2$ receptor antagonist if decreased first ligand binding is observed.

In still other illustrative examples, a plurality of different small test compounds may be synthesized on a solid substrate, such as plastic pins or some other surface. The test compounds may be reacted with an $AT_2$ receptor polypeptide, or fragments thereof. Bound polypeptide may then be detected by methods well known to those of skill in the art. The polypeptide may also be placed directly onto plates for use in the aforementioned drug screening techniques.

In other illustrative examples, the methods for identifying $AT_2$ receptor antagonists may include: contacting an $AT_2$ receptor polypeptide with individual members of a library of test samples; detecting an interaction between a test sample and an $AT_2$ receptor polypeptide; identifying a test sample that interacts with an $AT_2$ receptor polypeptide; and isolating a test sample that interacts with an AT2 receptor polypeptide.

In each of the foregoing screening methods, an interaction may be detected spectrophotometrically, radiologically or immunologically. An interaction between $AT_2$ receptor polypeptide and a test sample may also be quantified using methods known to those of skill in the art.

The screening methods may also include incubating a cell (e.g., an endothelial cell such as a coronary endothelial cell (CEC), a PC12W cell, a SK-UT-1 cell, a 3T3 fibroblast cell or a NG1 08-15 cell), which naturally or recombinantly expresses an $AT_2$ receptor on its surface, in the presence and absence of a candidate agent under conditions in which the $AT_2$ receptor is able to bind an $AT_2$ receptor ligand, and the level of $AT_2$ receptor activation is measured by a suitable assay. For example, an $AT_2$ receptor antagonist may be identified by measuring the ability of a candidate agent to decrease $AT_2$ receptor activation in the cell from a baseline value in the presence of receptor ligand. For example, PC12W cells are exposed to, or cultured in the presence of Ang II and in the presence and absence of the candidate agent under conditions in which the $AT_2$ receptor is active on the cells, and differentiation of the cells is measured. An agent tests positive for $AT_2$ receptor antagonism if it inhibits differentiation of the cells. In another example, PC12W cells may be exposed to, or cultured in the presence of Ang II and in the presence and absence of, the candidate agent under conditions in which the $AT_2$ receptor is active on the cells, and the level of nitric oxide or the level or functional activity of nitric oxide synthase in the cells is measured. An agent will test positive for $AT_2$ receptor antagonism if it inhibits nitric oxide or the level or functional activity of nitric oxide synthase. In another illustrative example, coronary endothelial cells may be exposed to, or cultured in the presence of Ang II and in the presence and absence of, the candidate agent under conditions in which the $AT_2$ receptor is active on the cells, and expression of Zfhep, which is a protein associated with cell differentiation, in the cells is measured. An agent will test positive for $AT_2$ receptor antagonism if it inhibits Zfhep expression in the cells. In specific embodiments, any $AT_1$ receptors on the surface of the cells may be blocked using an $AT_1$ receptor ligand, such as losartan and candesartan.

C. Other Antagonist Compounds

In addition to the $AT_2$ receptor antagonist compounds described above, other Ang II inhibitors that inhibit or block Ang II activity may also be used with the device of this invention.

These Ang II inhibitors may prevent Ang II production from its precursor molecule, angiotensin I, as for example when the Ang II inhibitor is an angiotensin converting enzyme (ACE) inhibitor. Many peptido-mimetic ACE inhibitors are available and are widely used (see below). Alternatively, Ang II inhibitors may inhibit the production of the Ang II precursor, angiotensin I from angiotensinogen by inhibiting renin, the enzyme that catalyzes this reaction. Renin inhibitors are also available and well known to those of skill in the art. Ang II inhibitors may also be interfering with the transcription of the angiotensinogen gene, or by interfering with the expression of the angiotensinogen protein from the angiotensinogen mRNA.

Examples of Ang II inhibitors include anti-renin monoclonal antibodies of U.S. Pat. No. 4,780,401; drugs and drug candidate molecules as Losartan (DuPont's DUP753/MK954) and polymorphs of Losartan disclosed in U.S. Pat. No. 5,608,075, Saralasin, ES-8891 and related N-substituted imidazole-2-ones disclosed in U.S. Pat. No. 5,087,634, SK&F 108566 (SmithKline & French), Remikirin (Roche R O 42-5892), Benzimidazole derivatives disclosed in U.S. Pat. No. 6,004,989, and Ortho-substituted benzoylguanidines described in U.S. Pat. No. 6,001,881; ACE inhibitors, such as BRL 36,378 of Beecham Laboratories disclosed in EP80822 and EP60668, CGS 14824 disclosed in UK Pat. No. 2103614, CGS 16,617 disclosed in U.S. Pat. No. 4,473,575 of Ciba Geigy, MC-838 of Chugai Pharmaceuticals disclosed in Canadian Pat. No. 102:72588v and Jap. J. Pharmacol. 40:373 (1986); the mercaptoalkanoyl prolines, such as Captopril (U.S. Pat. No. 4,105,776) and Zefenopril (U.S. Pat. No. 4,316,906), the carboxyalkyl dipeptide derivatives such as Enalapril (U.S. Pat. No. 4,374,829), Quinapril (U.S. Pat. No. 4,344,949), Perindopril (U.S. Pat. No. 4,508,729), Ramipril (U.S. Pat. No. 4,587,256) and Lisinopril (U.S. Pat. No. 5,045,553), and the carboxyalkyl dipeptide mimics such as Benzazepril (U.S. Pat. No. 4,410,520), Cilazapril (U.S. Pat. No. 4,512,924), phosphoalkanoyl prolines, such as Fosinopril (U.S. Pat. No. 4,168,267) and Fisinopril (U.S. Pat. No. 4,337,201), the phosphinylalkanoyl prolines, such as Trandopril and Pamipril (U.S. Pat. No. 5,256,687), the ether/thioether mercaptoacyl prolines, such as Zefenopril (U.S. Pat. No. 4,316,906), the N-aminoacyl amino acid derivatives, such as Anapryl (U.S. Pat. No. 5,589,499), the phosphonate substituted amino/imino acids such as Ceranopril (U.S. Pat. No. 4,452,790) and the phosphoamidates (See U.S. Pat. No. 4,432,971); renin inhibitors, such as urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471), a variety of other peptide analogs as disclosed in the following U.S. Pat. Nos. 5,071,837; 5,064,965; 5,063,207; 5,036,054; 5,036,053; 5,034,512 and 4,894,437, diol sulfonamides and sulfinyls (U.S. Pat. No.

5,098,924), N-morpholino derivatives (U.S. Pat. No. 5,055, 466), N-heterocyclic alcohols (U.S. Pat. No. 4,885,292) and pyrolimidazolones (U.S. Pat. No. 5,075,451), also, pepstatin derivatives (U.S. Pat. No. 4,980,283) and fluoro- and chloro-derivatives of statone-containing peptides (U.S. Pat. No. 5,066,643), anti-renin monoclonal antibodies such as those disclosed in U.S. Pat. No. 4,780,401.

All the $AT_2$ receptor antagonist compounds as well as Ang II antagonist compounds described above may be used in accordance with this invention. Other suitable $AT_2$ receptor antagonist compounds, derivatives, or mixtures thereof, will be known to those of ordinary skill in the art and are also included.

D. Compositions

An effective amount of an $AT_2$ receptor antagonist for use with the device of this invention may be in composition with a pharmaceutically acceptable carrier and/or diluent.

Any described herein and/or known $AT_2$ receptor antagonist may be used with the device of the present invention, provided that the $AT_2$ receptor antagonist is pharmaceutically active. A "pharmaceutically active" $AT_2$ receptor antagonist is in a form, which results in the treatment and/or prevention of aneurysm, such as aortic aneurysm, and aortic dissection, when provided to an individual.

The active compounds of the present invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Pharmaceutical compositions suitable for use in the present invention include compositions wherein the pharmaceutically active compounds are contained in an effective amount to achieve their intended purpose. The dose of active compounds administered to a patient should be sufficient to achieve a beneficial response in the patient over time such as a reduction in the size of the aneurysm or aortic dissection. The quantity of the pharmaceutically active compounds(s) to be delivered may depend on the subject to be treated inclusive of the age, sex, weight and general health condition thereof. In this regard, precise amounts of the active compound(s) for administration will depend on the judgment of the physician. In determining the effective amount of the active compound(s) to be administered in the treatment or prophylaxis of aortic aneurysm or aortic dissection, the physician may evaluate the size and the location of the aneurysm or aortic dissection. In any event, those of skill in the art may readily determine suitable dosages of the $AT_2$ receptor antagonists of the invention.

An effective amount of an $AT_2$ receptor antagonist is one that is effective for the treatment or prevention of aneurysm, such as aortic aneurysm, or aortic dissection.

Devices of the present invention that include $AT_2$ receptor antagonist(s) are suitable for treating an individual who has been diagnosed with an aneurysm or aortic dissection, who is suspected of having an aneurysm or aortic dissection, who is known to be susceptible and who is considered likely to develop an aneurysm or aortic dissection, or who is considered likely to develop a recurrence of a previously treated aneurysm or aortic dissection.

In some embodiments, the $AT_2$ receptor antagonist-containing compositions will generally contain about 0.000001% to 90%, about 0.0001% to 50%, or about 0.01% to about 25%, by weight of $AT_2$ receptor antagonist, the remainder being suitable pharmaceutical carriers or diluents etc. The dosage of the $AT_2$ receptor antagonist can be easily determined by a person of skill in the art using standard protocols.

In one example, $AT_2$ receptor antagonists may be, for example, admixed with excipients or carriers suitable for either enteral or parenteral application. In one embodiment, Ang II receptor antagonists may be admixed with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; and/or if desired c) disintegrants, e.g., starches, agar, alginic acid or its sodium salt, or effervescent mixtures. These compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The Ang II receptor antagonist compositions may be prepared according to conventional mixing, granulating or coating methods, respectively. The $AT_2$ receptor antagonist compositions may contain about 0.1 to 95% of the $AT_2$ receptor antagonist. In another embodiment, the $AT_2$ receptor antagonist compositions may contain about 0.1 to 75% of the $AT_2$ receptor antagonist. In yet another embodiment, the $AT_2$ receptor antagonist compositions may contain about 1 to 50% of the $AT_2$ receptor antagonist.

III. METHODS OF TREATMENT

In one embodiment, the present invention provides a method for treating a patient having an aneurysm, and especially abdominal aortic aneurysm, the method comprising a step of delivering a medical device of this invention and as described below to a point of treatment within the patient having the aneurysm. The medical device is adapted to release the $AT_2$ receptor antagonist compound at the point of treatment within the body lumen of the patient.

In another aspect, the present invention provides a method for treating a patient having an aortic dissection, the method comprising the step of delivering a medical device and $AT_2$ receptor antagonist compound of this invention and as described below to the patient at a point of treatment within the patient having the aortic dissection. The medical device is adapted to release the $AT_2$ receptor antagonist compound at or near the point of treatment within the body lumen of the patient.

For example, the medical device can release or retain an $AT_2$ receptor antagonist compound at a desired rate within a blood vessel upon placement proximate to an aneurysm or aortic dissection. By providing $AT_2$ receptor antagonist compound with the device, the progression of local endovascular disease or aortic dissection may be mitigated, stopped and/or reversed, preventing further weakening and dilation of the vessel wall or splitting of the layers of aorta.

In another aspect, the present invention provides a method of treating an aneurysm or an aortic dissection comprising radially expanding a medical device and $AT_2$ receptor antagonist compound of this invention and as described below, in a lumen with a balloon catheter, wherein the balloon catheter releases an $AT_2$ receptor antagonist.

In yet another aspect, the present invention is a method of treating an aneurysm or an aortic dissection comprising radially expanding a balloon catheter comprising an $AT_2$ receptor antagonist compound in a lumen, wherein the balloon catheter releases the $AT_2$ receptor antagonist compound within the lumen.

IV. MEDICAL DEVICES COMPRISING $AT_2$ RECEPTOR ANTAGONIST COMPOUNDS

In one embodiment, the invention provides a medical device and one or more $AT_2$ receptor antagonist compounds. The medical device may be an implantable device.

In one embodiment, a therapeutically effective concentration of $AT_2$ receptor antagonist compound can be incorporated in the medical device. The concentration of the $AT_2$ receptor antagonist compound per unit of ablumenal surface area of the medical device can be selected to achieve a desired tissue concentration upon implantation of the medical device. A therapeutically effective amount of $AT_2$ receptor antagonist compound can be selected based on considerations such as the material of the medical device surface, the design of the medical device, the coating configuration and the molecular structure of the $AT_2$ receptor antagonist compound, all of which can determine the rate of elution of the $AT_2$ receptor antagonist compound within a particular body vessel. In one instance, the $AT_2$ receptor antagonist compound is incorporated in the medical device so that from about 0.01 to about 100 μM of the $AT_2$ receptor antagonist compound is delivered to the affected tissue lining the wall of a body vessel proximate to the medical device. In another instance, the $AT_2$ receptor antagonist compound is incorporated in the medical device so that from about 25 to about 100 μM of the $AT_2$ receptor antagonist compound is delivered to the affected tissue lining the wall of a body vessel proximate to the medical device. In yet another instance, other concentrations of $AT_2$ receptor antagonist compound are contemplated (Wiest et al., *J Cardiovasc Pharmacol*, 17:177-184 (1991))

In one embodiment, the $AT_2$ receptor antagonist compound may be coated on the ablumenal surface of the medical device in an amount effective to modulate, decrease or inhibit aortic aneurysm or aortic dissection proximate to the ablumenal surface. In another embodiment, $AT_2$ receptor antagonist compounds may be coated on the ablumenal surface at concentrations sufficient to deliver a desired amount of the $AT_2$ receptor antagonist compound in an adjacent body vessel site to degradation. For instance, an $AT_2$ receptor antagonist compound may be included on the ablumenal surface of a medical device at a concentration effective to deliver from about 0.01 to about 100 μM of the $AT_2$ receptor antagonist compound to adjoining body vessel wall tissue upon placement of the medical device within the body vessel lumen. Alternatively, an $AT_2$ receptor antagonist compound may be included on the ablumenal surface of a medical device at a concentration effective to deliver from about 25 to about 100 μM of $AT_2$ receptor antagonist compound to adjoining body vessel wall tissue upon placement of the medical device within the body vessel lumen. Other concentrations of $AT_2$ receptor antagonist compound are also contemplated for including on the ablumenal surface of a medical device.

The medical device can be adapted to release an $AT_2$ receptor antagonist compound at a predetermined location within body of a patient. The medical device can have any suitable configuration. In one embodiment, the medical device may be an implantable medical device, such as graft, stent, and stent graft. The implantable medical device may be an endolumenal medical device, which may be placed inside a lumen of a patient. For example, a stent graft may be placed inside a body vessel. Alternatively, an implantable device may be a medical device, which may be placed on the outside of a body lumen during an open surgery. For example, a vascular wrap comprising an $AT_2$ receptor antagonist compound may be placed on the outside of the vessel. In yet another embodiment, the medical device may be a delivery device, such as a balloon catheter. Exemplary medical devices are described below. Other configurations are also contemplated.

In one aspect, the medical device may be a stent 10. The stent may have any configuration adapted to maintain the lumen of a body vessel at a desired degree of patency. FIG. 1A shows a side view of a stent 10 configured as a radially-expandable frame 12 formed from a plurality of interconnected struts 16 and bends 14 forming a pair of longitudinally joined hoop members 11. Alternatively, a stent may include one or a plurality of radially-expanding stents such as Z-STENTS®, which are available from Cook, Incorporated (Bloomington, Ind.). The frame 12 defines a tubular lumen 18 and defines a plurality of openings 19 between the lumen 18 and the exterior surface of the frame.

The frame 12 can be formed from any suitable biocompatible material providing properties suited for an intended application, such as desired rigidity or flexibility. Stent 10 is capable of providing circumferential support while, at the same time, being axially flexible. The stent frame 12 may be formed by forming the desired pattern directly out of a tube, e.g. by laser cutting or chemical etching. Alternatively, the desired pattern may be formed out of a flat sheet, e.g. by laser cutting or chemical etching, and then rolling that flat sheet into a tube and joining the edges, e.g. by welding. Any other suitable manufacturing method known in the art may be employed for manufacturing a stent in accordance with the invention. Furthermore, stents may be formed by etching a pattern into a material or mold and depositing stent material in the pattern, such as by chemical vapor deposition or the like. Such stents may be formed of plastic, metal or other materials and may exhibit a multitude of configurations. The metals from which such stents are formed may include stainless steels, titanium, Nitinol, and tantalum among others.

The frame 12 can be configured in any suitable pattern providing desired hoop strength and flexibility within a body vessel. The stent 10 may be moveable from a radially compressed state to the radially expanded state shown in FIG. 1A. In the radially compressed state, the stent 10 may be symmetrically radially compressed about the longitudinal axis within the center of the tubular lumen 18, and loaded into a suitable catheter-based endolumenal delivery system. The stent 10 can be positioned at a point of treatment within a body vessel using the delivery system, and radially expanded by any suitable means to the radially expanded deployed state shown in FIG. 1A. Means for expanding the stent 10 can include inflation of a balloon within the tubular lumen 18 of the stent, or self-expansion of the stent 10 upon removal of a means for radially constraining the stent in the radially compressed state. The frame may be configured and formed from materials that provide balloon-expandable or radially-expanding structures.

The frame 12 may be a frame configured for treatment or prevention of aortic dissections. Specifically, the frame for treatment of aortic dissection may be configured to provide a radially outward force against the surface of an aorta upon implantation, providing a therapeutically effective radial force directed against the intima so as to compress the intimal, medial and/or adventitial layers of the aorta against one another, thereby preventing or mitigating aortic dissection. A self-expanding frame may be selected to have a self-expanded radius greater than the radius of the site of implantation within the aorta. The site of the frame may be selected based on medically appropriate criteria to provide a desired amount of radial force against the intimal wall of the aorta to treat or prevent aortic dissection. The frame may be formed from a self-expanding material, such as the nickel-titanium alloy NITINOL®, and may have any suitable configuration of struts and bends. For example, the frame can configured as a stent 10 as shown in FIG. 1A. Optionally, one or more frames having the configuration of stent 10 can be joined longitudinally to form an elongated prosthesis of a desired length. The stent 10 can form a repeating unit cell of the elongated prosthesis, and multiple stent 10 unit cells may be joined end to end in a manner that imparts a desired amount of lateral and tortional flexibility to the elongated prosthesis. Alternatively, a single elongated prosthesis may be formed as a single unit, for example by laser cutting a cannula of a nickel-titanium alloy to form a self-expanding stent comprising a plurality of unit cells with the configuration of stent 10. Balloon-expandable materials, such as stainless steel or cobalt-chromium alloys, may also be used to form prosthetic stents for treatment of aortic dissection. Inflation of a PTA balloon may be used to place the prosthesis within the aorta, and inflation of the balloon may be regulated to provide a desired radial force against the wall of the aorta.

In one embodiment, the stent 10 or elongated prosthesis comprising a plurality of stent 10 unit cells may be coated with a releasable $AT_2$ receptor antagonist compound in a manner that provides for the therapeutically effective release of the $AT_2$ receptor antagonist compound into the intimal wall of the aorta. An elongated prosthesis may be delivered or implanted at any medically appropriate site within the aorta, including the proximal or distal segment of the aorta. The elongated prosthesis may have any suitable configuration of struts, bends, and openings. One example of an elongated prosthesis is a self-expanding stainless steel stent for percutaneous implantation sold under the tradename ZENITH®, commercially available from Cook, Incorporated (Bloomington, Ind.). Other examples include a Wallstent variety stent, Cook-Z® Stent or Zilver Stent. Some exemplary stents are disclosed in U.S. Pat. Nos. 5,292,331; 6,090,127; 5,133,732; 4,739,762; and 5,421,955.

In one embodiment, the $AT_2$ receptor antagonist compound may be contained within a reservoir incorporated with the medical device.

Figure 4A:
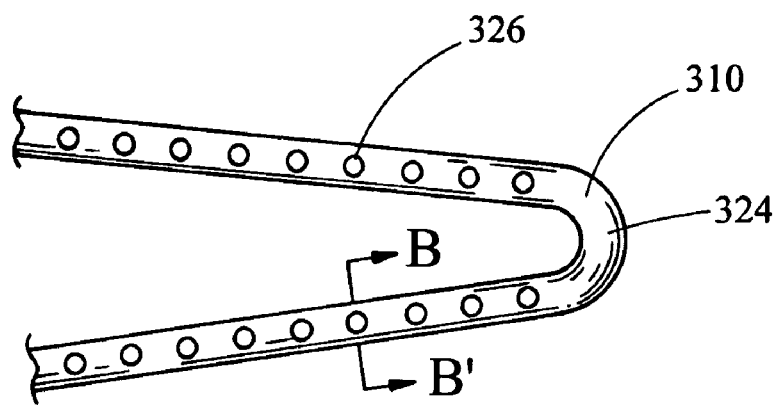
FIG. 4A is a partial, enlarged top view of a portion of a medical device.
Figure 4B:
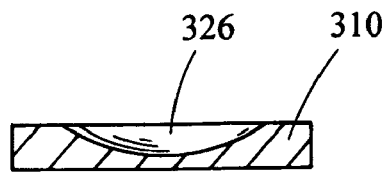
FIGS. 4B-4E are enlarged cross-sectional views along lines B-B' of the medical device of FIG. 4A.
Figure 4C:
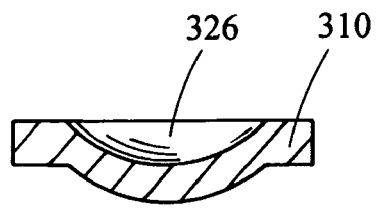
Figure 4D:
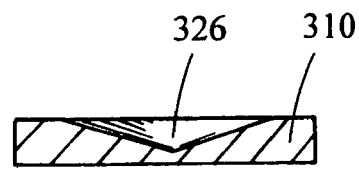
Figure 4E:
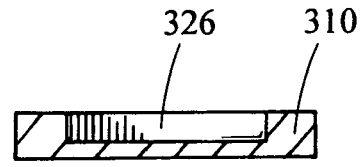

In one embodiment, the medical device may contain apertures, holes, wells, slots and the like occurring within the surface of the device for containing the $AT_2$ receptor antagonist compound and optionally containing other materials, such as a biodegradable polymer, mixed with or positioned in additional layers adjoining the $AT_2$ receptor antagonist compound. For example, the $AT_2$ receptor antagonist compound may be contained within a hole in a strut 16 or bend 14. In an alternative embodiment, the $AT_2$ receptor antagonist compound may be contained within wells formed in the strut 16 and/or a bend 14 portion of the frame 12. The wells may also be configured as slots or grooves in the surface of the frame 12. Placement of the releasable $AT_2$ receptor antagonist compound within a hole or well in the frame may provide the advantage of controlling the total amount of the $AT_2$ receptor antagonist compound released from the medical device 10, as well as the rate of release. Referring to FIG. 4A, the ablumenal surface 324 of an arcuate frame portion 310 of a medical device frame comprises a plurality of wells 326 containing an $AT_2$ receptor antagonist compound. The well 326 may contain a coating comprising the $AT_2$ receptor antagonist compound alone, a mixture of the $AT_2$ receptor antagonist compound with suitable polymers or a coating comprising multiple layers. FIGS. 4B-4E show cross sectional views of various well configurations along line B-B' of frame 310. The holes or wells may have any suitable shape or size, including a concave well formed by removing a portion of the frame 310 (FIG. 4B) or formed by re-shaping a portion of the frame (FIG. 4C), a V-shape well (FIG. 4D) or a square shaped well (FIG. 4E). The holes, wells, slots, grooves and the like, described above, may be formed in the surface of the release system of the medical device 10 by any suitable technique. For example, such techniques include drilling or cutting by utilizing lasers, electron-beam machining and the like or employing photoresist procedures and etching the desired apertures.

In one embodiment, the medical device may include hollow members that are adapted to contain the $AT_2$ receptor antagonist compound. Nearby, in vivo reservoirs may attach to these hollow members to supply the $AT_2$ receptor antagonist compound. Medical devices and methods for delivery of therapeutic agents using hollow members adapted to contain a drug were previously described in U.S. Provisional Pat. Application Ser. No. 60/794,634 filed Apr. 25, 2006, contents of which are incorporated herein in its entirety.

The stent may be balloon expandable or radially-expanding, including elastically self-expanding and thermally self-expanding. The balloon expandable stents are typically made of a ductile material, such as stainless steel tube, which has been machined to form a pattern of openings separated by stent elements. Radial expansion can be achieved by applying a radially outwardly directed force to the lumen of a balloon expandable stent and deforming the stent beyond its elastic limit from a smaller initial diameter to an enlarged final diameter. In this process the slots deform into "diamond shapes." Balloon expandable stents are typically radially and longitudinally rigid and have limited recoil after expansion. These stents have superior hoop strength against compressive forces but should this strength be overcome, the devices will deform and not recover. Balloon-expandable frame 12 structures may be formed from cobalt-chromium alloys or stainless steel materials. Self-expanding stents, on the other hand, may be fabricated from either spring metal or shape memory alloy wire, which has been woven, wound or formed into a stent having interstices separated with wire stent elements. When compared to balloon-expandable stents, these devices have less hoop strength but their inherent resiliency allows them to recover once a compressive force that results in deformation is removed. Other suitable frame materials include thermoformable polymers, such as polyethylene and polyurethane, and bioabsorbable polymer materials.

Several bioabsorbable, biocompatible polymers have been developed for use in medical devices, and have been approved for use by the U.S. Food and Drug Administration (FDA). These FDA-approved materials include polyglycolic acid (PGA), polylactic acid (PLA), Polyglactin 910 (comprising a 9:1 ratio of glycolide per lactide unit, and known also as VICRYL™), polyglyconate (comprising a 9:1 ratio of glycolide per trimethylene carbonate unit, and known also as MAXON™), and polydioxanone (PDS). In general, these materials biodegrade in vivo in a matter of months, although some more crystalline forms can biodegrade more slowly. Biodegradable polymers that can be used to form the support frame of a medical device, or can be coated on a frame, include a wide variety of materials. Examples of such materials include polyesters, polycarbonates, polyanhydrides, poly(amino acids), polyimines, polyphosphazenes and various naturally occurring biomolecular polymers, as well as co-polymers and derivatives thereof. Certain hydrogels, which are cross-linked polymers, can also be made to be biodegradable. These include, but are not necessarily limited to, polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, poly-alpha-hydroxy acids, trimethylene carbonate, poly-beta-hydroxy acids, polyorganophosphazines, polyanhydrides, polyesteramides, polyethylene oxide, polyester-ethers, polyphosphoester, polyphosphoester urethane, cyanoacrylates, poly(trimethylene carbonate), poly(iminocarbonate), polyalkylene oxalates, polyvinylpyrolidone, polyvinyl alcohol, poly-N-(2-hydroxypropyl)-methacrylamide, polyglycols, aliphatic polyesters, poly(orthoesters), poly(ester-amides), polyanhydrides, modified polysaccharides and modified proteins. Some specific examples of bioabsorbable materials include poly(epsilon-caprolactone), poly(dimethyl glycolic acid), poly(hydroxy butyrate), poly(p-dioxanone), polydioxanone, PEO/PLA, poly(lactide-co-glycolide), poly(hydroxybutyrate-co-valerate), poly(glycolic acid-co-trimethylene carbonate), poly(epsilon-caprolactone-co-p-dioxanone), poly-L-glutamic acid or poly-L-lysine, polylactic acid, polylactide, polyglycolic acid, polyglycolide, poly(D,L-lactic acid), L-polylactic acid, poly(glycolic acid), polyhydroxyvalerate, cellulose, chitin, dextran, fibrin, casein, fibrinogen, starch, and hyaluronic acid.

Figure 1B:
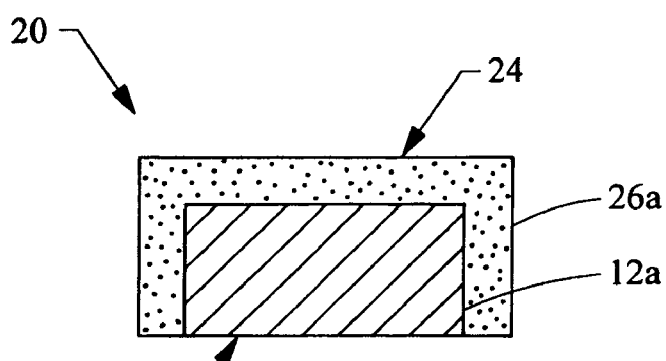
FIG. 1B is a cross section of a strut of an implantable medical device comprising a single-layer coating configuration.

At least a portion of the medical device frame 12 may be coated with one or more $AT_2$ receptor antagonist compounds ("bioactive compound"). The bioactive compound may be releasably associated with the frame 12 in any suitable manner that provides for the release of a therapeutically effective amount of the bioactive compound from the device upon placement of the frame 12 within a body vessel. For example, the bioactive compound may be adhered to a surface of the frame 12. Referring to FIG. 1A, the frame 12 comprises a lumenal surface defining the lumen 18 and an ablumenal surface positioned opposite the lumenal surface. FIG. 1B shows a cross section 20 view of a coated portion of the frame 12 along the line marked A-A' in FIG. 1A. The coating 26a comprises an $AT_2$ receptor antagonist compound and can have any suitable composition or configuration that provides for a therapeutically effective release of the bioactive compound within a body vessel. For example, the coating can optionally comprise a polymer matrix, such as a biodegradable polymer or a porous biostable polymer mixed with the $AT_2$ receptor antagonist compound. The coating 26a in FIG. 1B may be applied to the ablumenal surface 22 of the frame portion 12a, however the coating 26a could be applied to the ablumenal surface 22 in addition to, or instead of, application to the lumenal surface 24.

Figure 1C:
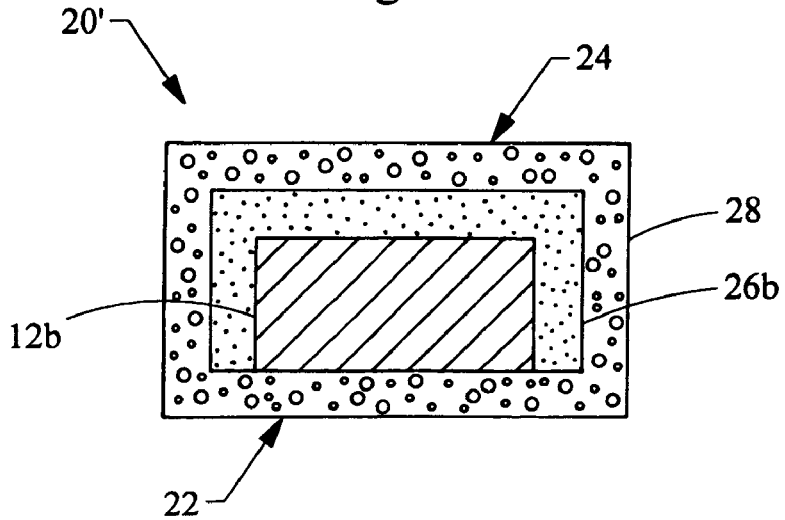
FIG. 1C is a cross section of a strut of an implantable medical device comprising a two-layer coating configuration.
Figure 1D:
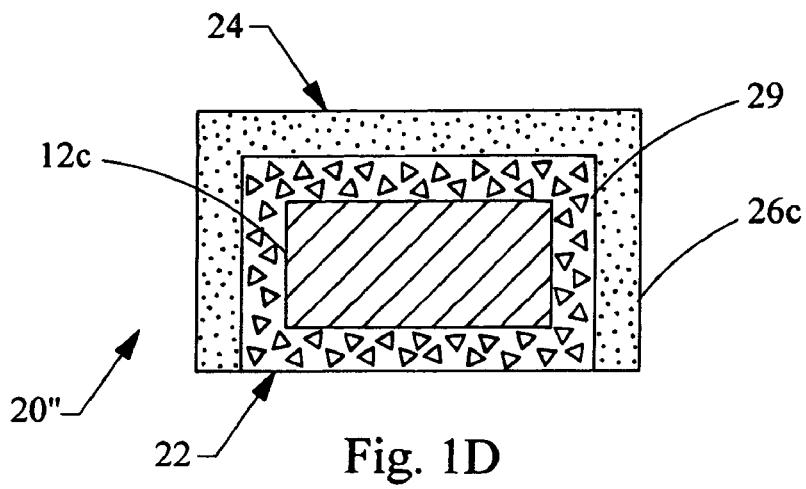
FIG. 1D is a cross section of a strut of an implantable medical device comprising an alternate two-layer coating configuration.

The coating may optionally comprise multiple layers. As such, these multiple layers may include varying amounts of $AT_2$ receptor antagonist compound(s) creating a drug gradient. Two, three, four or more layers including the $AT_2$ receptor antagonist compound(s) are contemplated. For example, FIG. 1C shows an alternative cross section 20' view of a coated portion of frame 12 along the line marked A-A' in FIG. 1A. The coating comprises two layers: a first layer 26b comprising an $AT_2$ receptor antagonist compound positioned on the ablumenal side 24 of frame portion 12b, and a second layer 28 positioned over the lumenal side 22 and the ablumenal side 24 of the first layer 26b. The second layer 28 can provide for a slower rate of release of the $AT_2$ receptor antagonist compound, for example by providing a porous diffusion barrier. The second layer 28 can comprise a biodegradable elastomer, such as poly(lactic acid), or a porous biostable material, such as parylene or a poly(alkyl)methacrylate (e.g., poly(butyl) methacrylate). FIG. 1D shows an alternative cross section 20" view of a coated portion of frame 12 along the line marked A-A' in FIG. 1A. The coating comprises two layers: a first layer 29 positioned over the lumenal side 22 and the ablumenal side 24 of frame portion 12c, and a second layer 26c positioned over the lumenal side 22 of the first layer. The second layer 26c comprises an $AT_2$ receptor antagonist compound, and optionally comprises other materials such as biodegradable or biostable polymer matrix-forming components. The first layer 29 can provide for a slower rate of release of the $AT_2$ receptor antagonist compound from the second layer 26c, for example by exerting an attractive force toward the second layer 26c (e.g., electrostatic or van der Waals forces). The second layer 28 can comprise a biodegradable elastomer, such as poly(lactic acid), or a porous biostable material, such as parylene or a poly(alkyl)methacrylate (e.g., poly(butyl)methacrylate). In other configurations, $AT_2$ receptor antagonist compounds may be linked to the surface of the drug release system without the need for a coating by means of detachable bonds and release with time. In yet other configurations, $AT_2$ receptor antagonist compounds may be included as a separate layer (separate carrier layer that includes $AT_2$ receptor antagonist compound(s)) that may be attached or placed near the frame 12. These bioactive compounds may be removed by active mechanical or chemical processes, or may be in a permanently immobilized form that presents the compounds at the implantation site. Multiple layers of bioactive compounds, or mixtures of carrier material/bioactive compounds, separated by polymer layers may be present to form a multilayer coating on a medical device. As discussed above, these layers may include varying amounts of the $AT_2$ receptor antagonist compound(s). In certain embodiments, different bioactive compounds may be present in the different layers. For example, different $AT_2$ receptor antagonist, may be present in different layers. In another embodiment, bioactive agents different from $AT_2$ receptor antagonists may also be included in addition to the $AT_2$ receptor antagonist in the same layers or different layers. Examples of other suitable bioactive agents are described below.

Figure 1E:
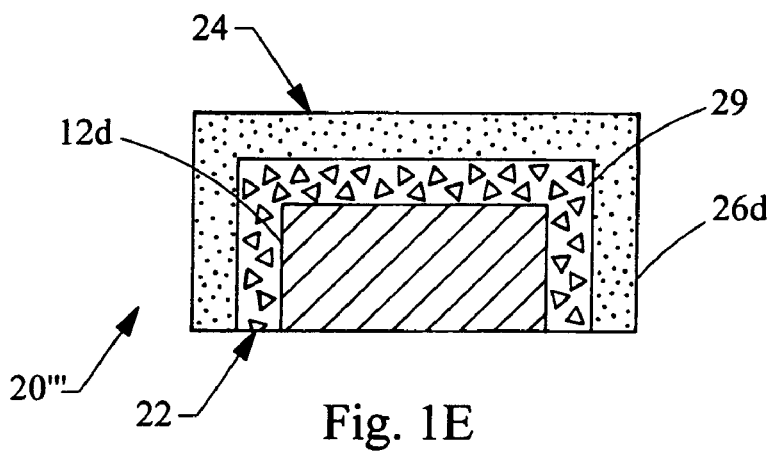
FIG. 1E is a cross section of a strut of an implantable medical device comprising another alternate two-layer coating configuration.

In one embodiment, the coating may also be confined to the ablumenal surface. Referring to FIG. 1E, an alternative cross section 20 view of a coated portion of frame 12 along the line marked A-A in FIG. 1A comprises a two-layer coating: a first layer 29 positioned over the ablumenal side 24 of frame portion 12d, and a second layer 26d positioned over the first layer. The second layer 26d comprises an $AT_2$ receptor antagonist compound, and optionally comprises other materials such as biodegradable or biostable polymer matrix-forming components. The coating does not cover the lumenal side 22 of the frame.

The $AT_2$ receptor antagonist compound(s) may be incorporated into the medical device in any suitable manner. The term "incorporated" means that $AT_2$ receptor antagonists are coated, adsorbed, placed, deposited, attached, impregnated, mixed, or otherwise incorporated into the device and the layers described herein by methods known in the art. Coating layers may be applied in sequential fashion by placing the layers near the medical device and/or spraying a solution comprising a volatile solvent and an $AT_2$ receptor antagonist to the surface of the medical device. A coating layer comprising an $AT_2$ receptor antagonist compound may be adhered to the surface of the device using an ultrasonic nozzle spray coating technique employing ultrasound to atomize a spray solution comprising the $AT_2$ receptor antagonist in suitable solvent, to provide a smooth and uniform coating. Optionally, the spray solution can further comprise a soluble polymer, such as a biodegradable polymer. In general, high frequency nozzles are smaller, create smaller drops, and consequently have smaller maximum flow capacity than nozzles that operate at lower frequencies. The ultrasonic nozzle can be operated at any suitable frequency, including 24 kHz, 35 kHz, 48 kHz, 60 kHz, 120 kHz or higher. A frequency of 60-120 kHz or higher may be used to atomize the solution comprising the $AT_2$ receptor antagonist. The nozzle power can be set at any suitable level, but may be about 0.9-1.2 W or alternatively about 1.0-1.1 W. The maximum flow rate and median drop diameter corresponding to particular nozzle designs can be selected as design parameters by one skilled in the art. In one embodiment, the flow rate may be between about 0.01-2.00 mL/min.

In another embodiment, the medical device may be a stent graft 100, as shown in FIG. 2A. The stent graft 100 may be formed from a graft material 130 and a frame 112. The frame 112 may comprise a plurality of longitudinally aligned hoops 110 attached to the tubular graft material 130 so as to define a cylindrical lumen 118. A distal frame hoop 111*a* may be flared radially outward to secure the stent graft 100 within a body vessel upon implantation. A first group of three frame hoops 111*b* may be positioned on the lumenal side 122 of the graft material 130 between a second group of frame hoops 111*c* positioned on the ablumenal 124 side of the graft material 130. A cross sectional view of a portion of a first frame hoop 111*b* is shown in detail view 102; a cross sectional a cross sectional view of a portion of a second frame hoop 111*c* is shown in detail view 104. The stent graft 100 may be moveable from a radially compressed state to the radially expanded state shown in FIG. 2A, for example by expansion of a balloon within the lumen 118, or by self expansion of the frame 112 within a body vessel. Medical devices may be packable in a compressed state within an endovascular delivery system having an outer diameter of from about 0.06 inches (5 French) to about 0.27 inches (20 French); preferably from about 0.10 inches (8 French) to about 0.22 inches (17 French); and most preferably from about 0.13 inches (10 French) to about 0.19 inches (14 French).

Resiliently compressible, self-expanding frames 112, such as self-expanding stent materials discussed above, are preferred in order to seal with the body lumen. PCT Application WO 98/53761, hereby incorporated by reference in its entirety, discloses a number of details concerning stents, stent grafts, and a method for implanting stent grafts into the human body.

The graft material 130 may be any suitable material for an intended use. The graft material 130 may be a woven or non-woven fabric, such as Dacron®, or may be a polymeric material such as expanded polytetrafluoroethylene (ePTFE), or may be a reconstituted or naturally derived collagenous material, such as small intestine submucosa (SIS). Other materials suitable for use as the graft material are also contemplated.

The graft material 130 may be selected and adapted to retain a therapeutically effective amount of an $AT_2$ receptor antagonist compound. The graft material may be selected from the group consisting of polyester, polyurethane (THORALON (THORATEC, Pleasanton, Calif.)), polyethylene, polypropylene and polytetrafluoroethylene. The graft material may alternatively be made from a reconstituted or naturally-derived collagenous material. Suitable bioremodelable materials may be provided by collagenous extracellular matrix materials (ECMs) possessing biotropic properties, including in certain forms angiogenic collagenous ECMs. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM may include other biological materials such as heparin, heparin sulfate, hyaluronic acid, fibronectin and the like.

Submucosa or other ECM materials may be derived from any suitable organ or other tissue source that usually contains connective tissues. The ECM materials processed for use as the graft material will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used as the graft material may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine,* 7:833-839 (2001). When combined with a fluorescence microangiography technique, this model can provide both quantitative and qualitative measures of angiogenesis into biomaterials. C. Johnson et al., *Circulation Research,* 94(2):262-268 (2004).

Submucosa or other ECM tissue used in the invention is preferably highly purified, for example, as described in U.S. Pat. No. 6,206,931. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used as the graft material in the present invention. Other collagen sources may be used in order to provide a desired amount of various collagen types including type I, III, IV and VI (Murata, et al., *Atherosclerosis*, 60(3):251-62 (June 1986)).

One type of submucosa for use as a graft material in this invention may be derived from the intestines. Another type of submucosa for use as a graft material in this invention may be derived from a small intestine, of a warm blooded vertebrate; i.e., SIS. SIS is commercially available from Cook Biotech, West Lafayette, Ind.

The graft material 130 may be attached to the frame 112 by any suitable method, including suturing, cross linking of the graft material 130 to the frame 112, or the application of adhesive compositions to join the frame 112 to the graft material 130 or by heat or by ultrasonic bonding.

Any portion of the stent graft may be coated with or include the $AT_2$ receptor antagonist compound.

In one embodiment, an $AT_2$ receptor antagonist compound may be coated or positioned within or on the graft material 130. One or more $AT_2$ receptor antagonist bioactive materials may be incorporated in or coated on a graft material 130 by any suitable method. Various methods of coating, impregnating, or lining the graft fabric with the bioactive compounds may be utilized and are known in the art. For example, the bioactive compounds may be deposited onto the graft fabric by spraying, dipping, pouring, pumping, brushing, wiping, vacuum deposition, vapor deposition, plasma deposition, electrostatic deposition, epitaxial growth, or any other method known to those skilled in the art. The type of coating or vehicle utilized to immobilize the bioactive compound to the graft material may vary depending on a number of factors, including the type of the medical device, including the graft material, the type of bioactive compound, and the rate of release thereof. Bioactive compounds may be incorporated into or mixed with the graft material during the formation of the graft material. The bioactive compound may be present in a liquid, a finely divided solid, or any other appropriate physical form when the graft material solidifies from a solution. In another embodiment, bioactive compounds may be incorporated into a solid form of the graft material, for example by spraying or dipping. Optionally, the graft material, or a coating applied thereto, may include one or more additives, for example, auxiliary substances, such as diluents, carriers, excipients, stabilizers, or the like. Optionally, an adhesion-promoting coating layer may be applied to the graft material prior to coating it with the bioactive compound. The adhesion promoting layer can be configured to provide a durable coating of the bioactive adhered to the graft material. Examples of suitable adhesion promoting materials include silane and parylene polymers. The amount of bioactive compound will be dependent upon a particular bioactive employed and medical condition to be treated. In one embodiment, the bioactive compound remains on the graft material during the delivery and implantation of the medical device. Accordingly, various materials may be utilized as surface modifications to prevent the bioactive compound from coming off prematurely. These materials are known and commonly used in the art.

One particular method of coating or impregnating a graft involves impregnating the graft with the bioactive compound by applying pressure to force the compound into the interstices of the graft. Pressure or force can be applied using a number of mechanical means for impregnating a solution of the bioactive compound into the graft material. Once coated, the grafts are allowed to dry and then may be subjected to sterilizing conditions prior to introduction into the body.

In one aspect, a dry, finely subdivided bioactive compound may be blended with a wet or fluid material, such as ePTFE, used to form the graft material before the material solidifies. Alternatively, air pressure or other suitable means may be employed to disperse the bioactive compound substantially evenly within the pores of the solidified graft material 130. In situations where the bioactive compound is insoluble in the wet or fluid graft material, the bioactive compound may be finely subdivided as by grinding with a mortar and pestle or by other means. The bioactive compound may be micronized, e.g., a product wherein some or all particles are the size of about 5 microns or less. The finely subdivided bioactive compound can then be distributed desirably substantially evenly throughout the bulk of the wet or fluid ePTFE layer before cross-linking or cure solidifies the layer. Alternatively, a bioactive compound may be incorporated into the graft material 130 by mixing a crystalline, particulate material (e.g., salt or sugar) that is not soluble in a solvent into an extrudate used to make the graft material to form the extrudate; casting the extrudate solution with particulate material; and then applying a second solvent, such as water, to dissolve and remove the particulate material, thereby leaving a porous graft material 130. The graft material 130 may then be placed into a solution containing a bioactive compound in order to fill the pores. In one embodiment, the stent graft would be exposed to a vacuum during solution impregnation to insure that the bioactive compound applied to it is received into the pores. Alternatively, the bioactive compound may be coated on the outside surface of the graft material. The drug may be applied to the outside surface of the graft material such as by dipping, spraying, or painting.

Optionally, the bioactive compound may be contained within a reservoir, such as encapsulated in microparticles, such as microspheres, microfibers or microfibrils, which can then be incorporated into a graft material. Various methods are known for encapsulating bioactives within microparticles or microfibers (see Patrick B. Deasy, Microencapsulation and Related Drug Processes, Marel Dekker, Inc., New York, 1984). For example, a suitable microsphere for incorporation would have a diameter of about 10 microns or less. The microsphere could be contained within the mesh of fine fibrils connecting the matrix of nodes in the graft material. The microparticles containing the drug may be incorporated within a zone by adhesively positioning them onto the material or by mixing the microparticles with a fluid or gel and flowing them into the graft material. The fluid or gel mixed with the microparticles could, for example, be a carrier agent designed to improve the cellular uptake of the bioactive compound incorporated into the graft material. Moreover, it is well within the contemplation of the present invention that carrier agents, which may include hyaluronic acid, may be incorporated within each of the embodiments of the present invention so as to enhance cellular uptake of the bioactive compound associated with the device. The microparticles embedded in the graft material may have a polymeric wall surrounding the bioactive compound or a matrix containing the bioactive compound and optional carrier agents. Moreover, microfibers or microfibrils, which may be bioactive compound loaded by extrusion, can be adhesively layered or woven into the graft material. Alternatively, the bioactive compound may be coated on the outside surface of the graft material. The bioactive may be applied to the outside surface of the graft material by, for example, dipping, spraying, or painting.

Alternatively, the graft material may further include a coating posited over the graft material. The coating may include, for example, a biocompatible hydrophilic material, such as hydrophilic polymer. Hydrophilic polymers that may be suitable for use as a coating for the graft fabric material are readily and commercially available from, for example, Biosearch Medical Products, Sommerville, N.J.; Hydromer Inc. Branchburg, N.J.; Surmodics, Eden Prairie, Wis.; and STS Biopolymers, Inc., Henrietta, N.Y. For example, hydrophilic polymer may include, but not be limited to, polyethylene oxide, polyvinyl pyrrolidone, polyethylene glycol, carboxylmethyl cellulose, hydroxymethyl cellulose, and other suitable hydrophilic polymers, or a combination thereof.

Figure 2A:
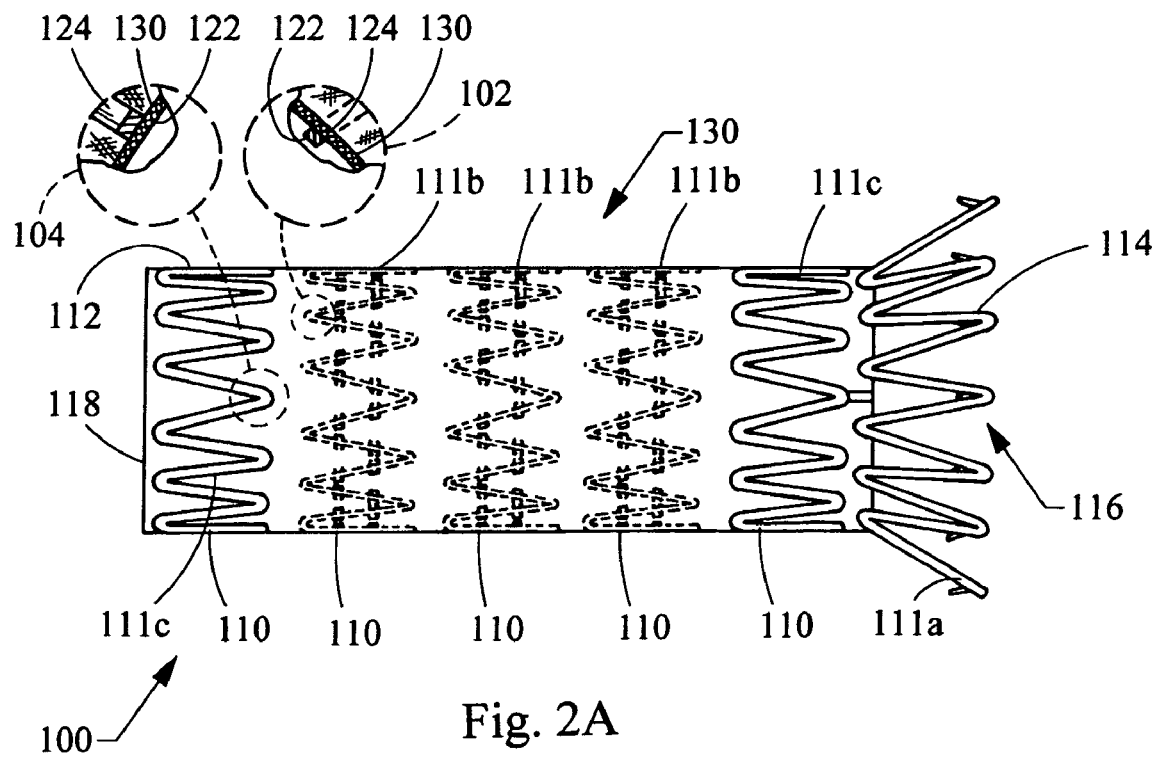
FIG. 2A is a side view of a first stent graft implantable medical device.
Figure 2B:
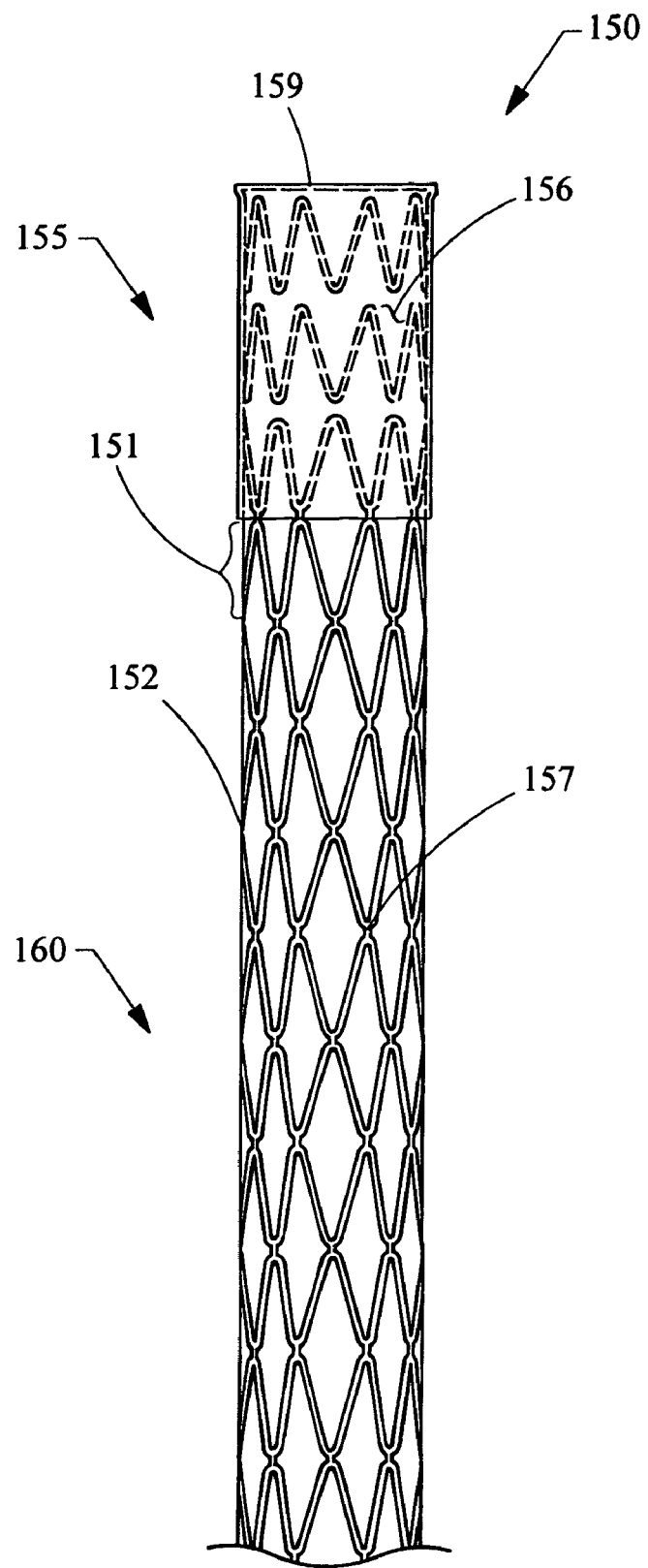
FIG. 2B is a side view of a second stent graft implantable medical device.

The medical device may also be configured as an elongated stent graft for treatment of aortic dissections as described in published U.S. Publication No. 2004/0176832 A1, published on Sep. 9, 2004, which is incorporated by reference in its entirety. For example, FIG. 2B shows an elongated stent graft 150 in a radially expanded configuration. The elongated stent graft 150 comprises an elongated frame 152 and a biocompatible graft material cover 156 around a first end 159 of the elongated stent graft 150 to form a covered portion 155 and an uncovered frame portion 160. The elongated frame 152 is formed from a plurality of longitudinally connected hoop members 151 joined by flexible links 157. Each hoop member 151 is formed from a sinusoidal member comprising an interconnected array of struts and bends. The flexible links 157 enable each hoop member 151 to radially expand separately. The elongated stent graft 150 may have a total length of from 100 to 300 mm and a diameter when expanded of 22 to 45 mm. The covered portion 156 may have a length of from 50 to 150 mm and a diameter when expanded of 22 to 45 mm. The length of the elongated stent graft 150 may be selected based on various factors, including the nature of the aortic aneurysm or dissection, the length of aorta at the site of treatment, and the dimensions of the aneurysm or the rupture in the wall of the aorta. Optionally, the elongated stent graft 150 may include barbs at the first end 159 of the elongated stent graft 150. The elongated frame 152 may be in the form of a mesh and formed from a biocompatible and biodegradable mesh material to permit dissipation of the elongated frame 152 after a desired period of time within a blood vessel.

Figure 3:
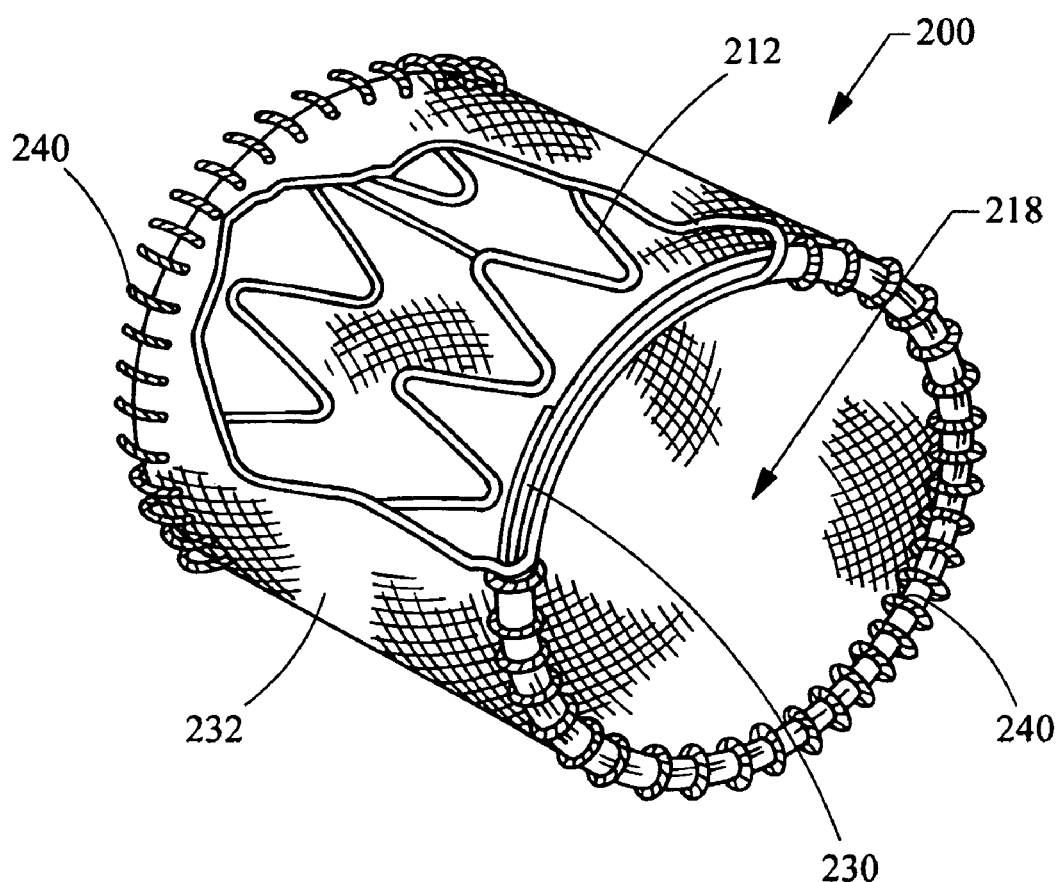
FIG. 3 is a perspective view of a third stent graft implantable medical device comprising a two-layer graft material.

Referring to FIG. 3, a stent graft 200, may comprise a multilayered graft material construct including a frame 212 positioned between an inner tubular graft material 230 defining the lumen 218 and an outer tubular graft material 232 defining the outer surface of the stent graft 200. The frame 212 and the nested tubular graft materials 230, 232 can be joined by a plurality of sutures 240 at each end of the stent graft 200. One or more bioactive compounds can be incorporated in each of the tubular graft materials 230, 232. For example, an $AT_2$ receptor antagonist agent may be included within the outer tubular graft material 232, and a second bioactive compound may be included within the inner tubular graft material 230. The second bioactive compound can be selected for retention or release into fluid flowing through the lumen 218.

A medical device may be compressible into a radially compressed delivery configuration being configured for implantation from a suitably small delivery system. In one embodiment, the delivery system has sufficient pushability, trackability and lateral flexibility. The device may be delivered to the treatment site by endovascular insertion. Preferably, the endovascular delivery system is sufficiently rigid to enable the health practitioner performing the implantation procedure to push the delivery system deep into the vascular tree of a patient, but not so rigid as to cause vascular damage during the implantation procedure. Furthermore, the delivery system would have enough lateral flexibility to allow tracking of the path of any one of the blood vessels leading to the implantation site. A delivery system, or introducer, typically comprises a cannula or a catheter, having a variety of shapes according to the intended clinical application and implantation site. The medical device may be radially collapsed and inserted into the catheter or cannula using conventional methods. In addition to the cannula or catheter, various other components may need to be provided in order to obtain a delivery system that is optimally suited for its intended purpose. These include and are not limited to various outer sheaths, pushers, stoppers, wire guides, sensors, etc. Once the device is deployed within a vessel, it expands and it can remain in place indefinitely, acting as a substitute vessel for the flow of blood or other fluids. Alternatively, if the device may be intended for temporary treatment, it can be removed after a desired period of time (hours, days, months, or years) from within the patient by conventional means.

In yet another embodiment, a medical device may be configured as a medical device delivery system comprising an $AT_2$ receptor antagonist compound. The delivery system may include a structure, such as a balloon catheter, configured to deliver the medical device to a predetermined location within a body lumen of a patient and release an $AT_2$ receptor antagonist compound before, during or after deployment of the medical device. Examples of balloons used for drug delivery were described in U.S. Publication No. 2004/0073190 A1, published on Apr. 15, 2004, and U.S. Publication No. 2005/0278021 A1, published on Dec. 15, 2005, the disclosures of which are incorporated by reference in their entirety.

Figure 5:
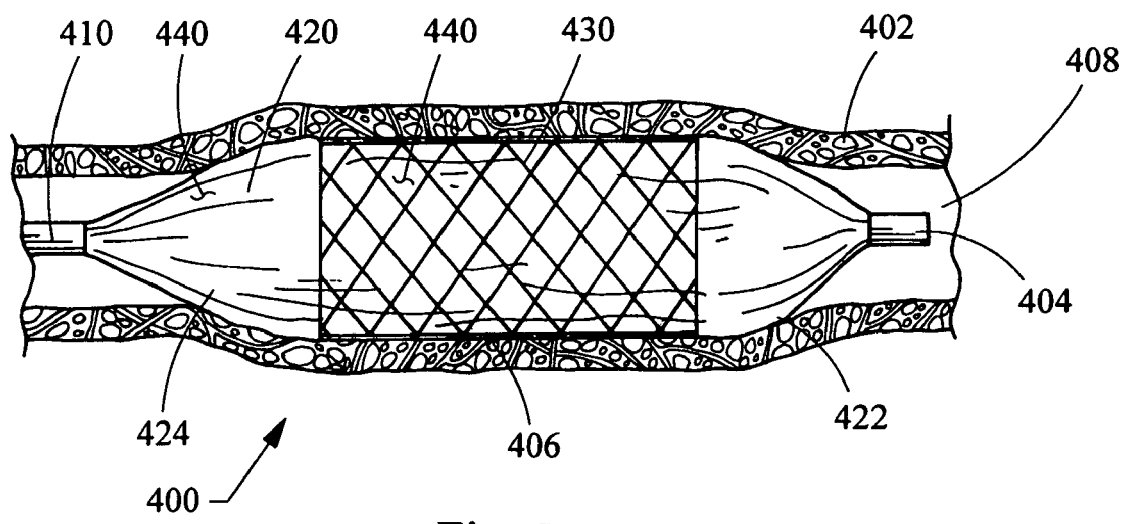
FIG. 5 is a medical device configured as a coated balloon.

FIG. 5 shows a portion of a distal portion of a catheter device 400 coated with the $AT_2$ receptor antagonist compound. The catheter 410 may include an inflatable balloon 420 proximate to the distal end 404 of the catheter 410. Inflation of the coated balloon 420 within a body vessel 402 may place the $AT_2$ receptor antagonist compound in contact with the wall 406 of the body vessel 402. The balloon 420 may be inflated to a controlled pressure (e.g., up to 1 to 20 atm) to fill the cross-section of the body lumen 408 and press the coated balloon surface 440 against the wall 406 of the body vessel lumen 408. The coated balloon surface 440 is configured to release the $AT_2$ receptor antagonist compound from the surface of the balloon 420 during compression of the inflated balloon against the wall 406 of the body vessel lumen 408.

Optionally, at least a portion of the coating 440 of the expandable balloon may include the $AT_2$ receptor antagonist compound mixed with, or layered with, a swellable hydrogel polymer. In one instance, the coating 440 may have a thickness in the range of about 10 to 50 microns in the swelled state. The hydrogel polymer may be selected from the group consisting of polycarboxylic acids, cellulosic polymers, gelatin, polyvinylpyrrolidone, maleic anhydride polymers, polyamides, polyvinyl alcohols, and polyethylene oxides. In general, when dry, the hydrogel coating may be on the order of about 1 to 10 microns thick. Typically, the hydrogel coating thickness may swell by about a factor of 6 to 10 or more when the hydrogel coating is hydrated. For example, a 1 to 3 microns thick hydrogel coating, when dry, may swell to about 10-30 microns thickness when hydrated. For example, a hydrogel coating on an angioplasty balloon may be coated on the surface of a balloon catheter (e.g., polyethylene) by applying a solution of 4,4' diphenylmethane diisocyanate (MDI) in methylethylketone to the surface of the balloon. After drying in an air oven at 85 C for 30 minutes, the balloon may be dipped in a solution of poly(acrylic acid) in dimethylformamide (DMF) and tertiarybutyl alcohol. The balloon may be oven dried to remove solvent from the coating. The surface of the balloon becomes instantly lubricous upon exposure to water. The formation of the hydrogel is further described in U.S. Pat. No. 5,091,205. The $AT_2$ receptor antagonist compound may be incorporated within the hydrogel polymer coating by, for example, dipping a hydrogel coated balloon in an aqueous solution of the $AT_2$ receptor antagonist agent.

The medical device may be a balloon catheter configured to deliver the $AT_2$ receptor antagonist compound and to deploy a second medical device, such as a radially-expandable stent crimped around the balloon portion of the catheter. For example, referring again to FIG. 5, a second medical device, such as a stent 430, can be crimped over a balloon coated with the $AT_2$ receptor antagonist agent. Expansion of the coated balloon portion 440 of the catheter 410 can function to radially expand and deploy a stent 430, while simultaneously releasing the $AT_2$ receptor antagonist compound onto the lumenal surface of the stent 430 and/or the wall 406 of the body vessel 402. The $AT_2$ receptor antagonist compound can be coated on at least a portion of the inflatable balloon 420, for instance at the proximal region 424 and distal region 422 that extend longitudinally beyond a crimped stent 430. Inflation of the balloon 420 typically leads to inflation of the distal region 422 and proximal region 424 of the balloon 420 (also referred to as the "dogbone" inflation pattern). In one embodiment, the $AT_2$ receptor antagonist compound may be coated on the distal region 422 and the proximal region 424 of the balloon 420 that are not enclosed by the stent 430. During delivery of a stent 430 by balloon inflation, the proximal region 424 and distal region 422 may radially expand before the portion of the balloon 420 enclosed by the stent 430, thereby delivering the $AT_2$ receptor antagonist compound to the wall of the body vessel before the stent is fully expanded.

The medical device may be an infusion catheter comprising one or more drug delivery channels from the central lumen of the catheter to the outer surface of the catheter. For example, an $AT_2$ receptor antagonist compound may be locally delivered in liquid form from the catheter near a point of treatment within an aorta. Optionally, the infusion catheter medical device may include one or more balloons. In one aspect, the infusion catheter includes a pair of balloons spaced longitudinally along the catheter, and one or more channels in communication with the outside surface of the catheter between the balloons. The balloons may be inflated prior to or during delivery of the $AT_2$ receptor antagonist compound, localizing the $AT_2$ receptor antagonist compound within an isolated segment of the body vessel between the two balloons.

The infusion catheter may also include a balloon segment with one or more pores permitting delivery of the $AT_2$ receptor antagonist compound across the balloon membrane. The balloon may be inflated with air or with a solution of the $AT_2$ receptor antagonist compound that is released through the balloon pores at a desired rate. The size of the pores, the viscosity and concentration of the solution comprising the $AT_2$ receptor antagonist agent, as well as the inflation pressure of the balloon, may be selected to provide a desired rate of delivery of the $AT_2$ receptor antagonist compound to a vessel wall upon inflation of the balloon.

A catheter may also be utilized to deliver a plurality of delivery capsules, including an $AT_2$ receptor antagonist compound, which may be initially disposed over an exterior surface of an inflatable balloon. By inflating the balloon, the $AT_2$ receptor antagonist compound capsules may become implanted into the interior wall of the aneurysm. Catheter may then be removed, leaving the capsules in place. The capsules may be any of a variety of conventional controlled drug delivery structures intended to release the desired drug into the aneurysmal wall or dissected aortic wall over time at a controlled rate. Optionally, the capsules may comprise hooks or other similar anchors for holding the capsules in the wall.

The $AT_2$ receptor antagonist compound may also be placed on the balloon in a form of microencapsulated spheres, which may be disposed on the exterior of or extruded within the wall of a balloon associated with a balloon catheter. The balloon catheter and balloon are conventional and well known in the art. The microcapsules may be fabricated in accordance with any of the known methods for preparing microcapsules. See U.S. Pat. Nos. 4,897,268; 4,675,189; 4,542,025; 4,530,840; 4,389,330; 4,622,244; 4,464,317; and 4,943,449, the disclosures of which are incorporated herein by reference. The microcapsulated spheres may be configured to release the $AT_2$ receptor antagonist compound when the balloon is inflated. As the balloon inflates, microcapsulated spheres containing the $AT_2$ receptor antagonist compound can detach from the expanding balloon coating. For example, a typical dilatation catheter balloon may expand in circumference by 500% which stresses the attachment points to the microcapsulated spheres. Other examples of suitable balloons using microencapsulated spheres were previously described in U.S. Pat. No. 6,129,705, disclosure of which is incorporated by reference herein in its entirety.

In one embodiment, a photodynamic therapy (PDT) balloon catheter may be used when an $AT_2$ receptor antagonist compound is formulated to be taken up at the treatment site (e.g., bond with the elastin or other constituents of the wall), then infrared, UV or visible light (of wavelength of 200 nm up to 1200 nm) may be used to activate the drug. PDT balloon catheters were previously described in U.S. Pat. Nos. 5,797,868; 5,709,653; and 5,728,068, disclosures of which are incorporated by reference herein in their entirety. Two methods for photodynamic therapy (PDT) treatment of blood vessels including use of a balloon are disclosed in the Narciso, Jr. U.S. Pat. Nos. 5,169,395 and 5,298,018, which are also incorporated by reference herein in their entirety. The elastin-based biomaterials that may be used to for photodynamic therapy were described in U.S. Pat. No. 6,372,228, which is incorporated herein by reference in its entirety.

Figure 6:
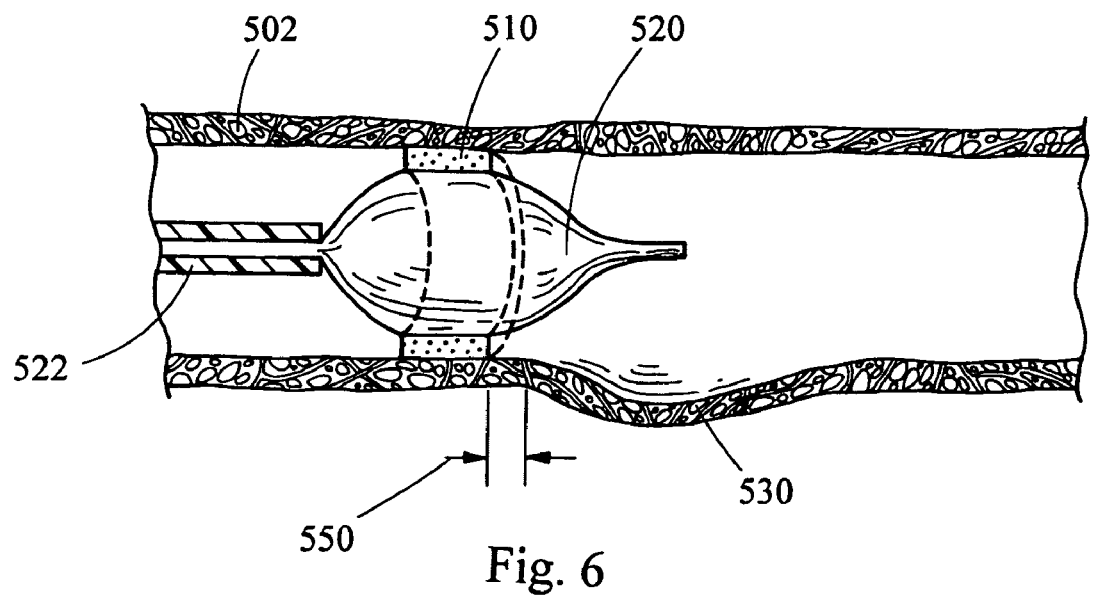
FIG. 6 is a medical device configured as a flexible material in an annular configuration.

In yet another embodiment, the medical device may be configured as a flexible graft material comprising an $AT_2$ receptor antagonist compound. The flexible graft material may have any suitable configuration, including a patch, sheet, tube, etc. Some specific examples include a tubular vascular graft, a flow-modifying device or an occluding device adapted for implantation within a body vessel or aneurysmal sac. The flexible graft material may be formed from any suitable material, including those described above with reference to the graft material for use with a stent graft. Exemplary materials include polyester, polyurethane, polyethylene, polypropylene, polytetrafluoroethylene (including ePTFE), reconstituted or naturally-derived collagenous material (e.g., ECM materials possessing biotropic properties, including in certain forms angiogenic collagenous ECMs). The $AT_2$ receptor antagonist compound may be coated on or impregnated into a graft material in any suitable manner, including the methods for attaching the $AT_2$ receptor antagonist compound to a graft material. FIG. 6 shows a flexible graft material 510 configured as a ring of an ECM material impregnated with a therapeutically-effective amount of an $AT_2$ receptor antagonist compound. The flexible graft material 510 may be placed around a balloon 520 portion of a delivery catheter 522 within a body vessel 502 comprising an aneurysm 530. The flexible graft material 510 may be delivered via delivery catheter 522 placing the flexible graft material 510 around the balloon 520, placing the balloon 520 at a desired implantation site within a body vessel lumen, and expanding the balloon 520 within the body vessel to bring the flexible graft material 510 into contact with the wall of the body vessel 502 in a manner that permits adhesion of the flexible graft material 510 to the body vessel 502. Optionally, the balloon 520 may be coated with an $AT_2$ receptor antagonist compound in addition to, or instead of, providing a flexible graft material 510 comprising an $AT_2$ receptor antagonist compound. The site of implantation may be positioned at a therapeutically effective distance 550 from an aneurysm 530. The ablumenal surface of the flexible material 510 can be configured to permit adhesive contact with the internal wall of a body vessel. For example, the ablumenal surface of the flexible graft material 510 may have a corrugated or porous morphology or may include an adhesive substance. In one embodiment, the ablumenal surface of the flexible graft material 510 includes a desired amount of $AT_2$ receptor antagonist compound releasably attached to the surface.

In one embodiment, an $AT_2$ receptor antagonist compound-loaded film may be pre-mounted upon a deflated balloon catheter. The balloon catheter may be maneuvered into the desired arterial or venous location using standard techniques. The balloon may then be inflated, compressing the stent (film material) against the vessel wall and then the balloon may be deflated and removed leaving the $AT_2$ receptor antagonist compound-loaded film in place. A protective sleeve (e.g., of plastic) may be used to protect the stent during its passage to the vessel and then withdrawn once the film is in the desired location.

In one embodiment, methods are provided for treating endovascular disease, such as aneurysm, and more specifically, an abdominal aortic aneurysm. The methods comprise delivering a medical device and an $AT_2$ receptor antagonist compound to a point of treatment in a patient having an aneurysm. The $AT_2$ receptor antagonist compound may be releasably incorporated into the medical device.

In another embodiment, the methods are provided for preventing or treating an aortic dissection. The methods comprise delivering a medical device and an $AT_2$ receptor antagonist compound to a point of treatment in a patient having the aortic dissection, or presenting symptoms thereof. The $AT_2$ receptor antagonist compound may be releasably incorporated into the medical device.

Figure 7:
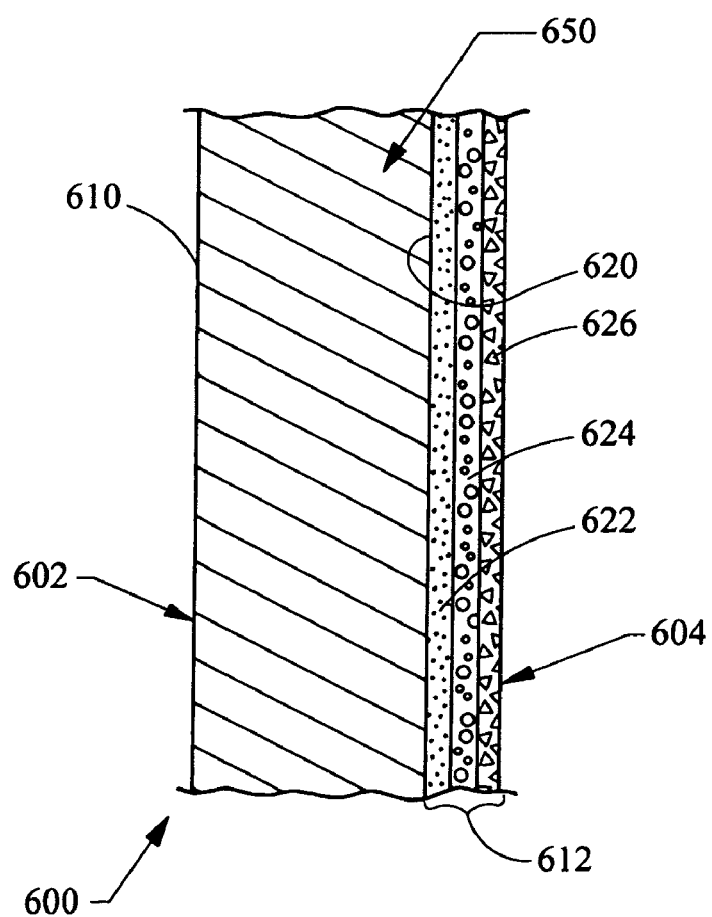
FIG. 7 is a radial cross section of an exemplary medical device.

In some embodiments, the $AT_2$ receptor antagonist compound may be releasably coated on one or more surfaces of the medical device. For example, FIG. 7 is a radial cross section 600 of a medical device formed from a medical device material 610 having a lumenal surface 610 facing the lumenal side 602 of the medical device and an ablumenal surface 620 facing toward the ablumenal side 604 of the medical device. The medical device material 610 represents a portion of any implantable medical device, including a stent frame, a graft material, a balloon portion or a catheter portion.

The medical device may include one or more coating or other layers that include $AT_2$ receptor antagonist compounds. For example, the medical device shown in FIG. 7 includes a three-layer coating positioned on the ablumenal surface 620, a first coating layer 622, a second coating layer 624, and a third coating layer 626. However, coatings may have any suitable number of layers, including 1, 2, 3, 4, 5, and 6-layer coatings applied to the lumenal surface 610 and/or the ablumenal surface 620. At least one or more separate sheet layers that include $AT_2$ receptor antagonist compounds embedded or otherwise included in the carrier material, which may be placed near the medical device or between the elements of the device, are also contemplated.

In one aspect, the coating 612 may form a concentration gradient of an $AT_2$ receptor antagonist compound. For example, in FIG. 7, the coating 612 comprises a first coating layer 622 having a first concentration of the $AT_2$ receptor antagonist compound in a carrier material, a second coating layer 624 having a second concentration of the $AT_2$ receptor antagonist compound in a carrier material and a third coating layer 626 having a third concentration of the $AT_2$ receptor antagonist compound in a carrier material. The carrier material may include, for example, a bioabsorbable polymer and/or a porous biostable polymer. Alternatively, the one or more coating layers may be positioned on the lumenal surface 610 instead, or in addition to, positioning coating layers on the ablumenal surface 620. The layers may optionally include the $AT_2$ receptor antagonist agent in combination with other bioactive agents, and/or carrier compositions.

In another aspect, the coating 612 may include one or more layers having different compositions. For example, the first coating layer 622 may be an adhesion-promoting layer comprising a material such as parylene or silane that promotes the adhesion of the second coating layer 624 to the coated medical device surface (e.g., the lumenal surface 610 or the ablumenal surface 620). The second coating layer 624 may include the $AT_2$ receptor antagonist compound and optionally comprise a carrier material such as a bioabsorbable polymer. The third coating layer 626 may include a porous material through which the $AT_2$ receptor antagonist compound in the second coating layer 624 may diffuse. Optionally, the third coating layer 626 may include a soluble material impregnated within an insoluble porous material, such that dissolution of the soluble material upon implantation of the medical device results in the formation of pores in the third coating layer 626. This or other layers may also contain adhesive material(s) that cause the layer(s) to adhere to the aorta wall.

Illustrative embodiments of the present invention have been described in considerable detail for the purpose of disclosing a practical, operative structure whereby the invention may be practiced advantageously. The designs described herein are intended to be exemplary only. The invention encompasses embodiments both comprising and consisting of the elements described herein with reference to the illustrative embodiments.

V. COMBINATION THERAPY

In one embodiment, the invention provides a medical device comprising one or more $AT_2$ receptor antagonist compounds and one or more other bioactive agents. In one embodiment, therapeutically effective amounts of the $AT_2$ receptor antagonist compound and bioactive agents are provided. Examples of suitable $AT_2$ receptor antagonist compounds were described above.

Other bioactive agents may be incorporated with the medical device using the methods which were described above in connection with incorporating the $AT_2$ receptor antagonist compounds with the medical device of this invention.

Other bioactive agents that may be incorporated with the medical device of this invention include MMPs inhibitors, including endogenous inhibitors, such as tissue inhibitors of MMPs (TIMPs) and α-macroglobulins, and synthetic inhibitors, such as chelating agents (e.g., EDTA and 1,10-phenanthroline), peptides, antibodies, and the like. Agents that would enhance function of TIMPs may also be used.

Any suitable tetracycline, including tetracycline per se, or tetracycline-derivative compounds, such as for example, doxycycline hydrate, doxycycline aureomycin and chloromycin may be included. Preferred tetracycline compounds include CMTs (CMT that lack the dimethylamino group at position 4 of the ring structure of tetracycline, including 4-dedimethylaminotetracycline (CMT-1), 4-dedimethylamino-5-oxytetracycline, 4-dedimethylamino-7-chlorotetracycline (CMT-4), 4-hydroxy-4-dedimethylaminotetracycline (CMT-6), 5a,6-anhydro-4-hydroxy-4-dedimethylaminotetracycline, 6-demethyl-6-deoxy-4-dedimethylaminotetracycline (CMT-3; COL-3), 4-dedimethylamino-12a-deoxytetracycline (CMT-7), and 6-α-deoxy-5-hydroxy-4-dedimethylaminotetracycline (CMT-8); tetracyclines modified at the 2 carbon position to produce a nitrile, e.g., tetracyclinonitrile; 6-α-benzylthiomethylenetetracycline, the mono-N-alkylated amide of tetracycline, 6-fluoro-6-demethyltetracycline, and 11α-chlorotetracycline).

In another embodiment beta blockers may be included. Beta blockers include acebutolol, atenolol, betaxolol, bisoprolol, carteolol, carvedilol, esmolol, labetolol, metoprolol, nadolol, penbutolol, pindolol, propranolol, and timolol.

Other bioactive agents useful in embodiments of this invention include cyclooxygenase-2 (COX-2) inhibitors; angiotensin-converting enzyme (ACE) inhibitors; glucocorticoids; nitric acid synthase (NOS) inhibitors; other anti-inflammatories; anti-oxidants; and cellular adhesion molecules (CAMs).

COX-2 inhibitors include Celecoxib, Rofecoxib, Valdecoxib, Etoricoxib, Parecoxib, all of which are available in pharmacological preparations. Additionally, COX-2 inhibition has been demonstrated from herbs, such as green tea, ginger, turmeric, chamomile, Chinese gold-thread, barberry, baikal skullcap, Japanese knotweed, rosemary, hops, feverfew, and oregano; and other agents, such as piroxican, mefenamic acid, meloxican, nimesulide, diclofenac, MF-tricyclide, raldecoxide, nambumetone, naproxen, herbimycin-A, and diaryl hydroxyfuranones.

NSAIDs that may be used in embodiments according to the present invention include ketorolac tromethamine (Toradol), indomethacin, ketorolac, ibuprofen and aspirin among others. Additionally, steroidal based anti-inflammatories, such as methylprednisolone, dexamethasone or sulfasalazine may be provided. Other suitable anti-inflammatory agents include cyclosporine A and azathioprine.

Another type of suitable bioactive agents are anti-oxidants, such as curcumin, vitamins, and vitamin constituents, such as α-tocopherol and β-carotene.

Yet other bioactive agents include ACE inhibitors, such as captopril, enalapril, losartan and lisinopril and the active forms of several ACE inhibitor prodrugs on the market.

Another group of bioactive agents that may be used include cathepsin inhibitors. Cathepsin inhibitors may be cysteine proteinase inhibitors, aspartic proteinase inhibitors, or serine proteinase inhibitors. For a comprehensive review of cathepsin inhibitors see Kim W. and Kang K, "Recent developments of cathepsin inhibitors and their selectivity," Expert Opin. Ther. Patents (2002) 12(3), pp 419-432. The medical devices comprising cathepsin inhibitors were previously described in U.S. Provisional Application No. 60/755,961, filed Jan. 3, 2006, which is incorporated herein by reference in its entirety.

Yet another group of bioactive agents include elastin-stabilizing compounds, such as tannic acid. Exemplary elastin-stabilizing compounds as well as medical devices including elastin-stabilizing compounds were previously described in U.S. Provisional Pat. Application Ser. No. 60/799,608, filed May 10, 2006, which is incorporated herein by reference in its entirety.

Other bioactive agents, such as the NOS inhibitors, including aminoguanidine are also useful in combination with the $AT_2$ receptor antagonist compounds of the present invention.

The invention also provides medical device coatings comprising the $AT_2$ receptor antagonist compounds in combination with one or more bioactive agents described in U.S. Pat. No. 5,834,449; U.S. Publication Nos. 2005/0266043 A1, published on Dec. 1, 2005, and 2006/0004441 A1, published on Jan. 5, 2006, which are incorporated herein by reference.

In addition to the embodiments described above, the invention includes combinations of the preferred embodiments discussed above, and variations of all embodiments.

We claim:

1. A medical device and an angiotensin II type 2 ($AT_2$) receptor antagonist compounds, the medical device comprising first and second polymer layers disposed on at least a portion of the medical device, and the medical device being adapted to release the $AT_2$ receptor antagonist compounds within a body lumen of a patient
wherein the first and the second polymer layers comprise $AT_2$ receptor antagonist compounds and
wherein $AT_2$ receptor antagonist compound of the second polymer layer is different from the $AT_2$ receptor antagonist compound of the first polymer layer.

2. The device of claim 1, wherein the medical device is a stent, the $AT_2$ receptor antagonist compounds releasably associated with the stent.

3. The device of claim 2, wherein the stent comprises a plurality on interconnected struts and bends and the $AT_2$ receptor antagonist compounds are releasably associated with the struts, bends, or a combination thereof.

4. The device of claim 2, wherein the stent comprises a plurality of Z-stents.

5. The device of claim 2, further comprising a coating comprising the $AT_2$ receptor antagonist compounds.

6. The device of claim 1, wherein the medical device is a stent graft comprising a support frame attached to a flexible tubular covering, the $AT_2$ receptor antagonist compounds releasably associated with at least a portion of the stent graft.

7. The device of claim 1, wherein the medical device comprises at least one surface adapted for contact with a body vessel wall and the $AT_2$ receptor antagonist compounds coated on at least a portion of the at least one surface.

8. The device of claim 6, wherein the flexible tubular covering comprises a covering selected from the group consisting of polyester, polyurethane, polyethylene, polyethylene terephthalate, polypropylene, polytetrafluoroethylene, reconstituted or naturally-derived collagenous material, and small intestine submucosa.

9. The medical device of claim 1, comprising an elongated member having an ablumenal surface and a lumenal surface defining a cylindrical lumen extending longitudinally along the length of the elongated member, wherein the $AT_2$ receptor antagonist compounds are releasably associated with at least one surface of the elongated member.

10. The device of claim 9, wherein the medical device is a stent graft having an elongated member configured as a flexible tubular covering forming at least a portion of the ablumenal surface, and further comprising a radially expandable support frame comprising a plurality of hoops attached to the elongated member, the cylindrical lumen forming a fluid conduit defined by the lumenal surface, wherein the $AT_2$ receptor antagonist compounds are releasably associated with the ablumenal surface of the elongated member.

11. The device of claim 10, wherein the flexible tubular covering comprises ePTFE or PTFE and the support frame comprises a plurality of radially-expandable members each comprising a plurality of interconnecting struts and bends.

12. The device of claim 11, wherein the flexible tubular covering comprises a covering selected from the group consisting of polyester, polyurethane, polyethylene, polyethylene terephthalate, polypropylene, polytetrafluoroethylene, reconstituted or naturally-derived collagenous material, and small intestine submucosa.

13. The device of claim 1, wherein the $AT_2$ receptor antagonist compounds are contained within a reservoir.

14. The device of claim 1, wherein the $AT_2$ receptor antagonist compounds are contained within a well or a groove.

15. The device of claim 1, wherein the $AT_2$ receptor antagonist compounds are in or disposed on at least one separate carrier layer.

16. The device of claim 1, further comprising a bioactive agent selected from the group consisting of matrix metalloproteinase's (MMPs) inhibitors, tetracycline, tetracycline-derivative compounds, beta blockers, cyclooxygenase-2 (COX-2) inhibitors, angiogenesis-converting enzyme (ACE) inhibitors, glucocorticoids, nitric acid synthase (NOS) inhibitors, anti-inflammatories, anti-oxidants, cellular adhesion molecules (CAMs), cathepsin inhibitors, elastin-stabilizing compounds, derivatives, and mixtures thereof.

17. The device of claim 16, wherein the bioactive agent is coated over the medical device and the $AT_2$ receptor antagonist compounds.

18. A kit comprising:
a medical device and an angiotensin II type 2 ($AT_2$) receptor antagonist compounds of claim 1; and
a balloon catheter comprising an $AT_2$ receptor antagonist compound.

* * * * *

SEQUENCE LISTING

```
<160> NUMBER OF SEQ ID NOS: 24

<210> SEQ ID NO 1
<211> LENGTH: 8
<212> TYPE: PRT
<213> ORGANISM: Artificial
<220> FEATURE:
<223> OTHER INFORMATION: AT II receptor antagonist

<400> SEQUENCE: 1

Asn Arg Val Tyr Val His Pro Ala
1               5

<210> SEQ ID NO 2
<211> LENGTH: 8
<212> TYPE: PRT
<213> ORGANISM: Artificial
<220> FEATURE:
<223> OTHER INFORMATION: AT II receptor antagonist

<400> SEQUENCE: 2

Asn Arg Val Tyr Val His Pro Leu
1               5
```

```
<210> SEQ ID NO 3
<211> LENGTH: 7
<212> TYPE: PRT
<213> ORGANISM: Artificial
<220> FEATURE:
<223> OTHER INFORMATION: AT II receptor antagonist
<220> FEATURE:
<221> NAME/KEY: MISC_FEATURE
<222> LOCATION: (0)..(1)
<223> OTHER INFORMATION: Succinyl

<400> SEQUENCE: 3

Arg Val Tyr Val His Pro Ala
1               5

<210> SEQ ID NO 4
<211> LENGTH: 8
<212> TYPE: PRT
<213> ORGANISM: Artificial
<220> FEATURE:
<223> OTHER INFORMATION: AT II receptor antagonist

<400> SEQUENCE: 4

Asp Arg Val Tyr Val His Pro Ala
1               5

<210> SEQ ID NO 5
<211> LENGTH: 7
<212> TYPE: PRT
<213> ORGANISM: Artificial
<220> FEATURE:
<223> OTHER INFORMATION: AT II receptor antagonist

<400> SEQUENCE: 5

Arg Val Tyr Val His Pro Ala
1               5

<210> SEQ ID NO 6
<211> LENGTH: 7
<212> TYPE: PRT
<213> ORGANISM: Artificial
<220> FEATURE:
<223> OTHER INFORMATION: AT II receptor antagonist
<220> FEATURE:
<221> NAME/KEY: MOD_RES
<222> LOCATION: (1)..(1)
<223> OTHER INFORMATION: MeGly

<400> SEQUENCE: 6

Gly Arg Val Tyr His Pro Ala
1               5

<210> SEQ ID NO 7
<211> LENGTH: 7
<212> TYPE: PRT
<213> ORGANISM: Artificial
<220> FEATURE:
<223> OTHER INFORMATION: AT II receptor antagonist
<220> FEATURE:
<221> NAME/KEY: MISC_FEATURE
<222> LOCATION: (0)..(1)
<223> OTHER INFORMATION: Succinamyl

<400> SEQUENCE: 7

Ser Arg Val Tyr His Pro Ala
1               5
```

```
<210> SEQ ID NO 8
<211> LENGTH: 7
<212> TYPE: PRT
<213> ORGANISM: Artificial
<220> FEATURE:
<223> OTHER INFORMATION: AT II receptor antagonist

<400> SEQUENCE: 8

Arg Val Tyr Val His Pro Ala
1               5

<210> SEQ ID NO 9
<211> LENGTH: 8
<212> TYPE: PRT
<213> ORGANISM: Artificial
<220> FEATURE:
<223> OTHER INFORMATION: AT II receptor antagonist

<400> SEQUENCE: 9

Asn Arg Val Tyr Val His Pro Gly
1               5

<210> SEQ ID NO 10
<211> LENGTH: 8
<212> TYPE: PRT
<213> ORGANISM: Artificial
<220> FEATURE:
<223> OTHER INFORMATION: AT II receptor antagonist

<400> SEQUENCE: 10

Asn Arg Val Tyr Val His Pro Ile
1               5

<210> SEQ ID NO 11
<211> LENGTH: 8
<212> TYPE: PRT
<213> ORGANISM: Artificial
<220> FEATURE:
<223> OTHER INFORMATION: AT II receptor antagonist
<220> FEATURE:
<221> NAME/KEY: MOD_RES
<222> LOCATION: (1)..(1)
<223> OTHER INFORMATION: MeGly

<400> SEQUENCE: 11

Gly Arg Val Tyr Val His Pro Gly
1               5

<210> SEQ ID NO 12
<211> LENGTH: 8
<212> TYPE: PRT
<213> ORGANISM: Artificial
<220> FEATURE:
<223> OTHER INFORMATION: AT II receptor antagonist

<400> SEQUENCE: 12

Pro Arg Val Tyr Val His Pro Gly
1               5

<210> SEQ ID NO 13
<211> LENGTH: 8
<212> TYPE: PRT
<213> ORGANISM: Artificial
<220> FEATURE:
<223> OTHER INFORMATION: AT II receptor antagonist
```

```
<400> SEQUENCE: 13

Asn Arg Val Tyr Val His Pro Gly
1               5

<210> SEQ ID NO 14
<211> LENGTH: 8
<212> TYPE: PRT
<213> ORGANISM: Artificial
<220> FEATURE:
<223> OTHER INFORMATION: AT II receptor antagonist
<220> FEATURE:
<221> NAME/KEY: MOD_RES
<222> LOCATION: (1)..(1)
<223> OTHER INFORMATION: MeGly
<220> FEATURE:
<221> NAME/KEY: MOD_RES
<222> LOCATION: (8)..(8)
<223> OTHER INFORMATION: bAla

<400> SEQUENCE: 14

Gly Arg Val Tyr Val His Pro Ala
1               5

<210> SEQ ID NO 15
<211> LENGTH: 8
<212> TYPE: PRT
<213> ORGANISM: Artificial
<220> FEATURE:
<223> OTHER INFORMATION: AT II receptor antagonist
<220> FEATURE:
<221> NAME/KEY: MOD_RES
<222> LOCATION: (8)..(8)
<223> OTHER INFORMATION: bAla

<400> SEQUENCE: 15

Asn Arg Val Tyr Val His Pro Ala
1               5

<210> SEQ ID NO 16
<211> LENGTH: 8
<212> TYPE: PRT
<213> ORGANISM: Artificial
<220> FEATURE:
<223> OTHER INFORMATION: AT II receptor antagonist

<400> SEQUENCE: 16

Gly Arg Val Tyr Val His Pro Ala
1               5

<210> SEQ ID NO 17
<211> LENGTH: 8
<212> TYPE: PRT
<213> ORGANISM: Artificial
<220> FEATURE:
<223> OTHER INFORMATION: AT II receptor antagonist
<220> FEATURE:
<221> NAME/KEY: MOD_RES
<222> LOCATION: (1)..(1)
<223> OTHER INFORMATION: MeGly

<400> SEQUENCE: 17

Gly Arg Val Tyr Ile His Pro Leu
1               5

<210> SEQ ID NO 18
<211> LENGTH: 8
<212> TYPE: PRT
<213> ORGANISM: Artificial
```

```
<220> FEATURE:
<223> OTHER INFORMATION: AT II receptor antagonist

<400> SEQUENCE: 18

Asn Arg Val Tyr Val His Pro Leu
1               5

<210> SEQ ID NO 19
<211> LENGTH: 8
<212> TYPE: PRT
<213> ORGANISM: Artificial
<220> FEATURE:
<223> OTHER INFORMATION: AT II receptor antagonist
<220> FEATURE:
<221> NAME/KEY: MOD_RES
<222> LOCATION: (1)..(1)
<223> OTHER INFORMATION: MeGly

<400> SEQUENCE: 19

Gly Arg Val Tyr Ile His Pro Ala
1               5

<210> SEQ ID NO 20
<211> LENGTH: 8
<212> TYPE: PRT
<213> ORGANISM: Artificial
<220> FEATURE:
<223> OTHER INFORMATION: AT II receptor antagonist

<400> SEQUENCE: 20

Asn Arg Val Tyr Ile His Pro Ala
1               5

<210> SEQ ID NO 21
<211> LENGTH: 8
<212> TYPE: PRT
<213> ORGANISM: Artificial
<220> FEATURE:
<223> OTHER INFORMATION: AT II receptor antagonist

<400> SEQUENCE: 21

Asn Arg Val Tyr Ala His Pro Ala
1               5

<210> SEQ ID NO 22
<211> LENGTH: 8
<212> TYPE: PRT
<213> ORGANISM: Artificial
<220> FEATURE:
<223> OTHER INFORMATION: AT II receptor antagonist

<400> SEQUENCE: 22

Asp Arg Val Phe Ile His Pro Tyr
1               5

<210> SEQ ID NO 23
<211> LENGTH: 8
<212> TYPE: PRT
<213> ORGANISM: Artificial
<220> FEATURE:
<223> OTHER INFORMATION: AT II receptor antagonist
<220> FEATURE:
<221> NAME/KEY: MISC_FEATURE
<222> LOCATION: (6)..(6)
<223> OTHER INFORMATION: p-NH2-Phe
```

-continued

```
<400> SEQUENCE: 23

Asp Arg Val Tyr Ile Phe Pro Phe
1               5

<210> SEQ ID NO 24
<211> LENGTH: 6
<212> TYPE: PRT
<213> ORGANISM: Artificial
<220> FEATURE:
<223> OTHER INFORMATION: AT II receptor antagonist
<220> FEATURE:
<221> NAME/KEY: MISC_FEATURE
<222> LOCATION: (1)..(1)
<223> OTHER INFORMATION: nicotinic acid
<220> FEATURE:
<221> NAME/KEY: MISC_FEATURE
<222> LOCATION: (2)..(2)
<223> OTHER INFORMATION: N-benzoylcarbonyl Arg

<400> SEQUENCE: 24

Tyr Arg Lys His Pro Ile
1               5
```